United States Patent
Kitao et al.

(10) Patent No.: US 11,013,728 B2
(45) Date of Patent: May 25, 2021

(54) CYCLIN-DEPENDENT KINASE 8 AND/OR 19 INHIBITOR

(71) Applicant: Kyoto Pharmaceutical Industries, Ltd., Kyoto (JP)

(72) Inventors: Tatsuya Kitao, Kyoto (JP); Shigemitsu Takeda, Kyoto (JP); Yoshimichi Shoji, Kyoto (JP); Hiroaki Shirahase, Kyoto (JP)

(73) Assignee: Kyoto Pharmaceutical Industries, Ltd., Kyoto (JP)

( * ) Notice: Subject to any disclaimer, the term of this patent is extended or adjusted under 35 U.S.C. 154(b) by 70 days.

(21) Appl. No.: 16/500,395

(22) PCT Filed: Apr. 2, 2018

(86) PCT No.: PCT/JP2018/014163
§ 371 (c)(1),
(2) Date: Oct. 2, 2019

(87) PCT Pub. No.: WO2018/186366
PCT Pub. Date: Oct. 11, 2018

(65) Prior Publication Data
US 2021/0100783 A1    Apr. 8, 2021

(30) Foreign Application Priority Data
Apr. 3, 2017    (JP) .............................. JP2017-073969

(51) Int. Cl.
| | |
|---|---|
| *A61K 31/4427* | (2006.01) |
| *A61K 31/4433* | (2006.01) |
| *A61K 45/06* | (2006.01) |
| *A61K 31/397* | (2006.01) |
| *A61K 31/4545* | (2006.01) |
| *A61K 31/5377* | (2006.01) |
| *A61K 31/496* | (2006.01) |
| *A61K 31/495* | (2006.01) |
| *A61K 31/443* | (2006.01) |
| *A61K 31/351* | (2006.01) |
| *A61K 31/166* | (2006.01) |
| *A61K 31/382* | (2006.01) |
| *A61K 31/341* | (2006.01) |
| *A61K 31/196* | (2006.01) |
| *A61K 31/5375* | (2006.01) |
| *A61K 31/451* | (2006.01) |
| *A61K 31/357* | (2006.01) |
| *A61P 35/02* | (2006.01) |

(52) U.S. Cl.
CPC ........ *A61K 31/4427* (2013.01); *A61K 31/166* (2013.01); *A61K 31/196* (2013.01); *A61K 31/341* (2013.01); *A61K 31/351* (2013.01); *A61K 31/357* (2013.01); *A61K 31/382* (2013.01); *A61K 31/397* (2013.01); *A61K 31/443* (2013.01); *A61K 31/4433* (2013.01); *A61K 31/451* (2013.01); *A61K 31/4545* (2013.01); *A61K 31/495* (2013.01); *A61K 31/496* (2013.01); *A61K 31/5375* (2013.01); *A61K 31/5377* (2013.01); *A61K 45/06* (2013.01); *A61P 35/02* (2018.01)

(58) Field of Classification Search
CPC .................................................. A61K 31/4427
USPC ...................................................... 514/210.2
See application file for complete search history.

(56) References Cited

U.S. PATENT DOCUMENTS

| | | | |
|---|---|---|---|
| 9,321,737 B2 | 4/2016 | Roninson et al. | |
| 9,745,299 B2 | 8/2017 | Rzymski et al. | |
| 9,745,325 B2 | 8/2017 | Okaniwa et al. | |
| 9,957,251 B2 | 5/2018 | Hirayama et al. | |
| 10,059,663 B2 | 8/2018 | Shirahase et al. | |

(Continued)

FOREIGN PATENT DOCUMENTS

| | | |
|---|---|---|
| JP | 2015-506376 A1 | 3/2015 |
| JP | 2016-503408 A1 | 2/2016 |

(Continued)

OTHER PUBLICATIONS

European Patent Office, Extended European Search Report in European Patent Application No. 18780484.4 (dated Oct. 20, 2020).

(Continued)

*Primary Examiner* — Taofiq A Solola
(74) *Attorney, Agent, or Firm* — Leydig, Voit & Mayer, Ltd.

(57) ABSTRACT

The present invention aims to provide a novel cyclin-dependent kinase 8 and/or 19 inhibitor useful as an anti-cancer agent. The present invention relates to a cyclin-dependent kinase 8 and/or 19 inhibitor containing a compound represented by the formula (I):

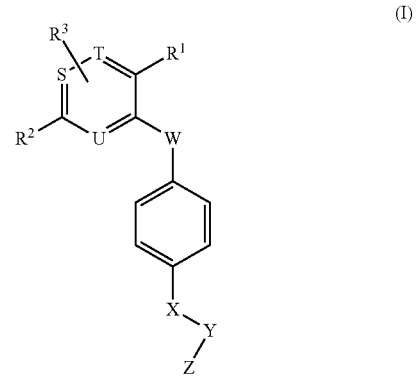

(I)

[wherein each symbol is as defined in the DESCRIPTION] or a pharmaceutically acceptable salt thereof as an active ingredient, and use thereof as an agent for preventing and/or treating cancer.

13 Claims, No Drawings

(56) References Cited

U.S. PATENT DOCUMENTS

| | | |
|---|---|---|
| 2008/0200531 A1 | 8/2008 | Chang et al. |
| 2012/0071477 A1 | 3/2012 | Porter et al. |
| 2014/0038958 A1 | 2/2014 | Ronnison et al. |
| 2015/0274726 A1 | 10/2015 | Rzymski et al. |
| 2016/0000787 A1 | 1/2016 | Broude et al. |
| 2016/0207883 A1 | 7/2016 | Shirahase et al. |
| 2017/0037057 A1 | 2/2017 | Okaniwa et al. |
| 2017/0044132 A1 | 2/2017 | Hirayama et al. |
| 2017/0071942 A1 | 3/2017 | Roninson et al. |

FOREIGN PATENT DOCUMENTS

| | | |
|---|---|---|
| WO | WO 2007/133772 A1 | 11/2007 |
| WO | WO 2014/154723 A1 | 10/2014 |
| WO | WO 2015/030189 A1 | 3/2015 |
| WO | WO 2015/159937 A1 | 10/2015 |
| WO | WO 2015/159938 A1 | 10/2015 |

OTHER PUBLICATIONS

Clark et al., "Mediator kinase module and human tumorigenesis," *Crit. Rev. Biochem. Mol. Biol.*, 50(5): 393-426 (2015).

Firestein et al., "CDK8 is a colorectal cancer oncogene that regulates β-catenin activity," *Nature*, 455(7212): 547-551 (2008).

Pelish et al., "Mediator Kinase Inhibition Further Activates Super-Enhancer Associated Genes in AML," *Nature*, 526(7572): 273-276 and Extended Data (2015).

Rzymski et al., "CDK8 kinase—An emerging target in targeted cancer therapy," *Biochimica et Biophysica Acta*, 1854(10): 1617-1629 (2015).

Japanese Patent Office, International Search Report in International Patent Application No. PCT/JP2018/014163 (dated Jun. 5, 2018).

CYCLIN-DEPENDENT KINASE 8 AND/OR 19 INHIBITOR

CROSS-REFERENCE TO RELATED APPLICATIONS

This patent application is the U.S. national phase of International Patent Application No. PCT/JP2018/014163, filed Apr. 2, 2018, which claims the benefit of Japanese Patent Application No. 2017-073969, filed on Apr. 3, 2017, which are incorporated by reference in their entireties herein.

TECHNICAL FIELD

The present invention relates to a compound having a cyclin-dependent kinase (CDK) 8 and/or CDK19 inhibitory activity, or a pharmaceutically acceptable salt thereof. Furthermore, the present invention relates to a compound useful for the preventing and/or treating diseases associated with CDK8 and/or CDK19, including cell proliferative diseases such as cancer and the like, or a pharmaceutically acceptable salt thereof.

BACKGROUND ART

CDK is a phosphoenzyme that is activated by forming a complex with a cyclin protein, and is known as a factor involved in cell cycle and transcriptional regulation. In particular, it is known that CDK2, CDK4 and CDK6 are mainly involved in the cell cycle, and CDK7, CDK8 and CDK9 are mainly involved in transcription. Among them, CDK8 forms a complex with cyclin C, MED12 and MED13, and acts as a kinase that mainly controls transcription by controlling phosphorylation of the C-terminal domain and the like of RNA polymerase II (non-patent document 1).

It has been reported that CDK8 is an oncogene in a part of colorectal cancer cells, and CDK8 expression is promoted in colorectal cancer patients, which activates F3-catenin signal and positively controls cell proliferation (non-patent document 2). Furthermore, CDK8 is known to be also involved in the maintenance of undifferentiated state of cancer cells and epithelial mesenchymal transition.

In addition, it has been reported that CDK8 inhibitor Cortistatin A suppresses proliferation of various cancer cells and particularly shows remarkable effects on leukemia cells (non-patent document 3).

Non-patent document 4 discloses that a compound that inhibits CDK8 is useful for the treatment or prophylaxis of cancer, and patent documents 1-6 disclose CDK inhibitors having an anti-cancer action.

Patent document 7 discloses a novel aromatic compound having an osteogenesis promoting action. However, the action of these compounds on CDK8 and/or CDK19 is not known.

DOCUMENT LIST

Patent Documents

Patent document 1: US-A-2012/0071477
Patent document 2: WO 2007/133772
Patent document 3: WO 2013/116786
Patent document 4: WO 2014/072435
Patent document 5: WO 2015/159937
Patent document 6: WO 2015/159938
Patent document 7: WO 2015/030189

Non-Patent Documents

Non-patent document 1: A. D. Clark et al., Crit Rev Biochem Mol Biol., 50(5), 393-426 (2015)

Non-patent document 2: R. Firestein et al., Nature 455, 547-551 (2008)

Non-patent document 3: H. E. Pelish et al., Nature 526, 273-276 (2015)

Non-patent document 4: T. Rzymski et al., Biochim. Biophys. Acta, Volume 1845, 1617-1629 (2015)

SUMMARY OF THE INVENTION

Problems to be Solved by the Invention

The problem of the present invention is to provide a compound and a pharmaceutically acceptable salt which have a CDK8 and/or CDK19 inhibitory action, have high safety and can be administered orally. A further problem is to provide an agent for preventing and/or treating diseases associated with CDK8 and/or CDK19, including cell proliferative diseases such as cancer and the like.

Means of Solving the Problems

Under the circumstances, the present inventors have conducted intensive studies and found the superior compound of the present invention showing a strong inhibitory action on CDK8 and/or CDK19, that can be an agent for preventing and/or treating diseases associated with CDK8 and/or CDK19, including cell proliferative diseases such as cancer and the like, which resulted in the completion of the present invention.

That is, the present invention provides the following.

[1] A cyclin-dependent kinase 8 and/or 19 inhibitor comprising, as an active ingredient, a compound represented by the formula (I):

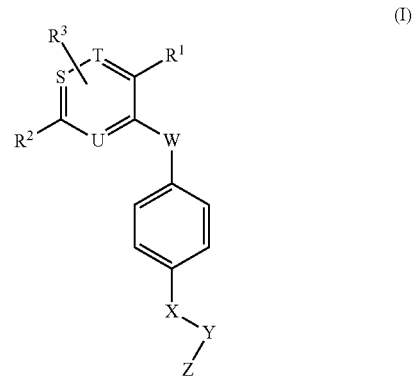

(I)

[wherein each substituent is as defined below:

$R^1$:
a cyano group, a C1-6 alkylcarbonyl group, a C1-6 alkylcarbonylamino group, a nitro group, a halogeno C1-6 alkyl group, a C2-6 alkenyl group, a halogeno C2-6 alkenyl group, a carbamoyl group or a hydroxy C1-6 alkyl group $R^2$:
a C1-6 alkoxy group, a carbamoyl group, a C1-6 alkylaminocarbonyl group or a C1-6 alkylcarbonyl group $R^3$:
a hydrogen atom or a halogen atom S, T and U:
when any one of S, T and U is =N—, others are =CH— (=C— when $R^3$ is substituted); or
all of S, T and U are =CH— (=C— when $R^3$ is substituted)

W:
—NH—, —O— or —S—

X:
a single bond, -saturated heterocyclyl-, —CH$_2$—(CH$_2$)$_n$—, —O—(CH$_2$)$_n$—, —(CH$_2$)$_n$—O— or —CH=CH—(CH$_2$)$_n$— n:
any one integer selected from 1-4

Y:
a single bond, —O— or —CO—

Z:
a hydrogen atom, a saturated heterocyclic group optionally substituted by any group selected from substituent group α or a C1-6 alkyl group optionally substituted by any group selected from substituent group α substituent group α:
a saturated heterocyclic group, a hydroxy C1-6 alkyl group, an aminosulfonylamino group, a carboxy group, a hydroxy group, a C1-6 alkoxy group, a C1-6 alkyl group],
or a pharmaceutically acceptable salt thereof (hereinafter sometimes to be abbreviated as compound (I)).

[2] The agent of the above-mentioned [1] wherein R$^1$ is a cyano group, an acetyl group, an acetylamino group, a nitro group, a trifluoromethyl group, a 1,1-difluoroethyl group, a 1-fluoroethyl group, a difluoromethyl group, a carbamoyl group or a 1-hydroxyethyl group.

[3] The agent of the above-mentioned [1] or [2] wherein R$^2$ is a methoxy group, a carbamoyl group, a methylaminocarbonyl group or an acetyl group.

[4] The agent of any of the above-mentioned [1] to [3] wherein all of S, T and U are =CH—.

[5] The agent of any of the above-mentioned [1] to [4] wherein X is -saturated heterocyclyl- or —O—(CH$_2$)$_n$— and n is 2.

[6] The agent of any of the above-mentioned [1] to [5] wherein Y is a single bond or —O—.

[7] The agent of any of the above-mentioned [1] to [6] wherein Z is a C1-6 alkyl group substituted by a hydroxy group, a tetrahydrofuranyl group, a tetrahydropyranyl group, a piperazinyl group or a morpholinyl group.

[8] The agent of the above-mentioned [1] wherein the compound represented by the formula (I) is at least one compound selected from the group consisting of (1) 3-{4-[3-(2-hydroxyethoxy)azetidin-1-yl]phenylamino}-N-methyl-4-nitrobenzamide,

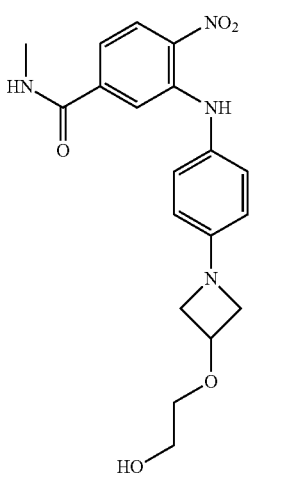 [SMILES: CNC(=O)c1ccc([N+](=O)[O-])c(Nc2ccc(N3CC(OCCO)C3)cc2)c1]

(2) 3-{4-[3-(2-hydroxyethoxy)azetidin-1-yl]phenylamino}-4-nitrobenzamide,

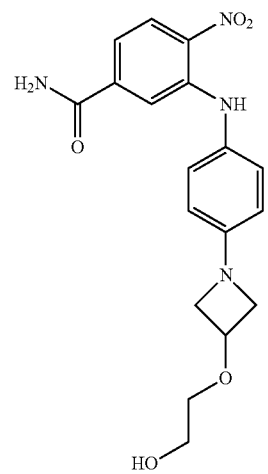

(3) 4-acetyl-3-{4-[2-(tetrahydropyran-4-yloxy)ethoxy]phenoxy}benzamide,

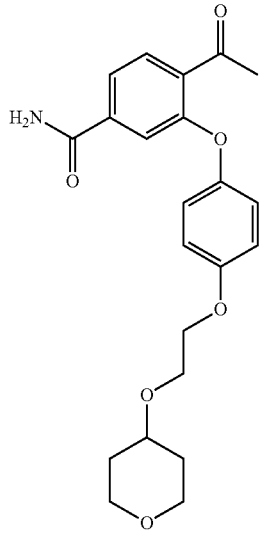

(4) 4-acetyl-3-{4-[2-(2-isopropoxyethoxy)ethoxy]phenoxy}benzamide,
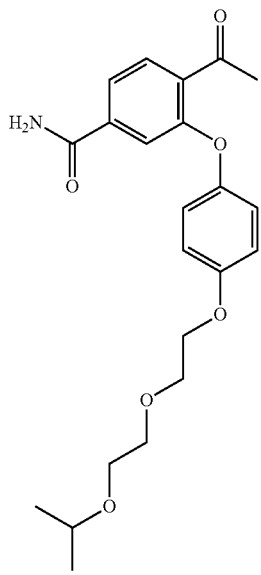 [SMILES: CC(=O)c1ccc(C(N)=O)cc1Oc1ccc(OCCOCCOC(C)C)cc1]
(5) 4-nitro-3-{4-[2-(tetrahydropyran-4-yloxy)ethoxy]phenylamino}benzamide,
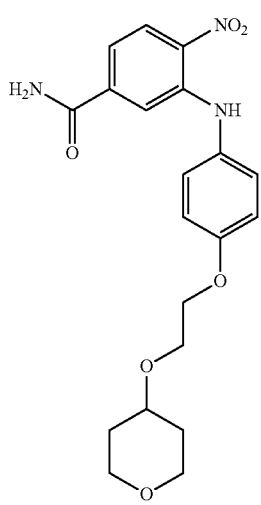 [SMILES: NC(=O)c1ccc([N+](=O)[O-])c(Nc2ccc(OCCOC3CCOCC3)cc2)c1]
(6) 4-acetyl-3-{4-[2-(tetrahydrofuran-3-yloxy)ethoxy]phenoxy}benzamide,
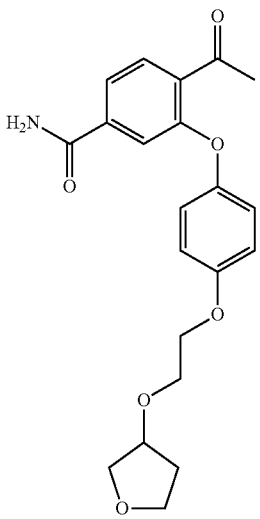
(7) 4-acetyl-3-{4-[3-(2-hydroxyethoxy)azetidin-1-yl]phenoxy}benzamide,
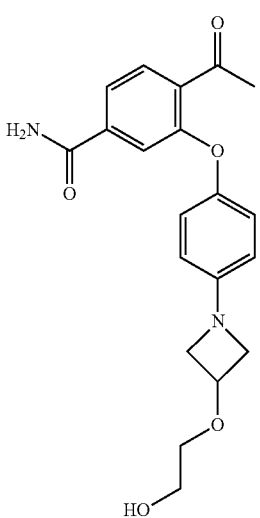 [SMILES: CC(=O)c1ccc(C(N)=O)cc1Oc1ccc(N2CC(OCCO)C2)cc1]

(8) 3-{4-[2-(tetrahydropyran-4-yloxy)ethoxy]phenoxy}-4-trifluoromethylbenzamide, and

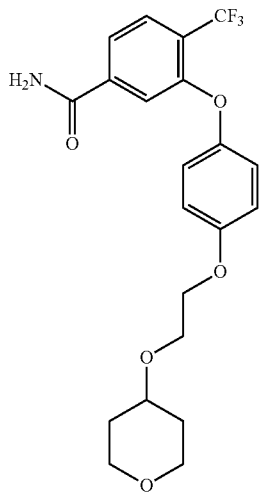 [SMILES: NC(=O)c1ccc(C(F)(F)F)c(Oc2ccc(OCCOC3CCOCC3)cc2)c1]

(9) 4-(1-fluorovinyl)-3-{4-[2-(tetrahydropyran-4-yloxy)ethoxy]phenoxy}benzamide

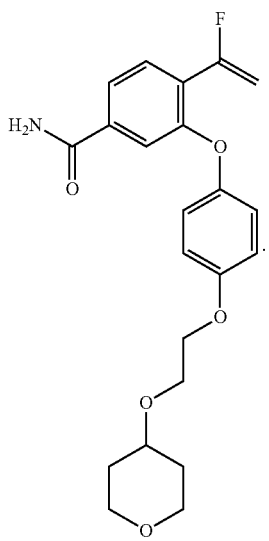 [SMILES: C=C(F)c1ccc(C(N)=O)cc1Oc1ccc(OCCOC2CCOCC2)cc1]

[9] The agent of any of the above-mentioned [1] to [8] that is an agent for preventing or treating cancer.
[10] The agent of the above-mentioned [9] wherein the aforementioned cancer is at least one kind selected from the group consisting of breast cancer, pancreatic cancer, bladder cancer, prostate cancer, esophageal cancer, stomach cancer, uterine cancer, ovarian cancer, brain tumor, colorectal cancer, hematologic cancer, liver cancer, skin cancer, lung cancer and thyroid cancer.
[11] An agent for preventing or treating cancer comprising the agent of any of the above-mentioned [1] to [10], and at least one kind selected from the group consisting of a chemotherapeutic agent, a hormonal therapeutic agent, a molecular targeting agent, an anti-inflammatory agent, an immunosuppressant and an immunotherapeutic agent.
[12] A method for preventing and/or treating cancer comprising administering an effective amount of a compound represented by the formula (I):

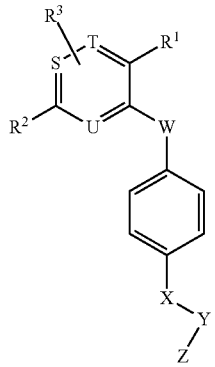

[wherein each substituent is as defined below:

$R^1$:

a cyano group, a C1-6 alkylcarbonyl group, a C1-6 alkylcarbonylamino group, a nitro group, a halogeno C1-6 alkyl group, a C2-6 alkenyl group, a halogeno C2-6 alkenyl group, a carbamoyl group or a hydroxy C1-6 alkyl group $R^2$:

a C1-6 alkoxy group, a carbamoyl group, a C1-6 alkylaminocarbonyl group or a C1-6 alkylcarbonyl group $R^3$:

a hydrogen atom or a halogen atom

S, T and U:

when any one of S, T and U is =N—, others are =CH— (=C— when $R^3$ is substituted); or all of S, T and U are =CH— (=C— when $R^3$ is substituted)

W:

—NH—, —O— or —S—

X:

a single bond, -saturated heterocyclyl-, —CH$_2$—(CH$_2$)$_n$—, —O—(CH$_2$)$_n$—, —(CH$_2$)$_n$—O— or —CH=CH—(CH$_2$)$_n$— n:

any one integer selected from 1-4

Y:

a single bond, —O— or —CO—

Z:

a hydrogen atom, a saturated heterocyclic group optionally substituted by any group selected from substituent group α or a C1-6 alkyl group optionally substituted by any group selected from substituent group α substituent group α:

a saturated heterocyclic group, a hydroxy C1-6 alkyl group, an aminosulfonylamino group, a carboxy group, a hydroxy group, a C1-6 alkoxy group, a C1-6 alkyl group], or a pharmaceutically acceptable salt thereof, to a patient in need thereof.

[13] The method of the above-mentioned [12] wherein the compound represented by the formula (I) is at least one compound selected from the group consisting of (1) 3-{4-[3-(2-hydroxyethoxy)azetidin-1-yl]phenylamino}-N-methyl-4-nitrobenzamide,
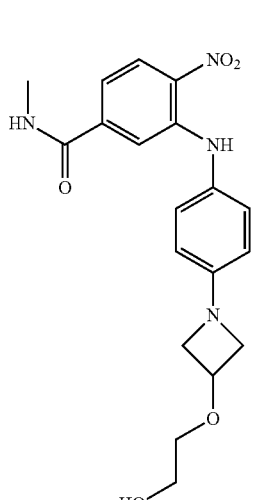
(2) 3-{4-[3-(2-hydroxyethoxy)azetidin-1-yl]phenylamino}-4-nitrobenzamide,
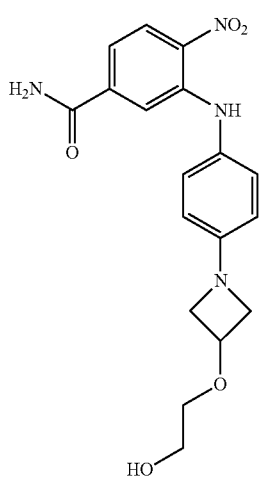
(3) 4-acetyl-3-{4-[2-(tetrahydropyran-4-yloxy)ethoxy]phenoxy}benzamide,
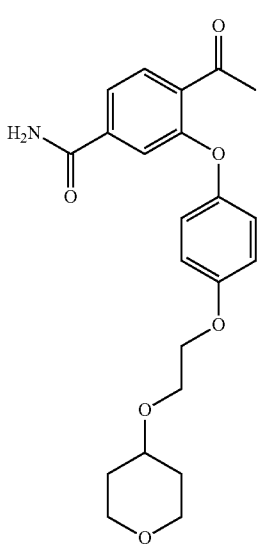
(4) 4-acetyl-3-{4-[2-(2-isopropoxyethoxy)ethoxy]phenoxy}benzamide,
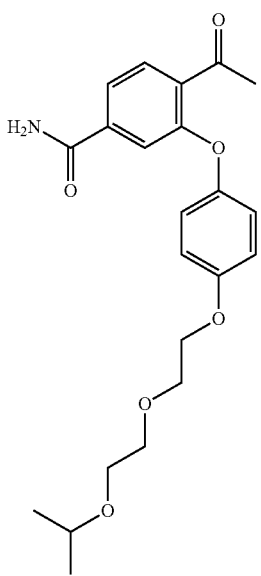 [SMILES: CC(=O)c1ccc(C(N)=O)cc1Oc1ccc(OCCOCCOC(C)C)cc1]

(5) 4-nitro-3-{4-[2-(tetrahydropyran-4-yloxy)ethoxy]phenylamino}benzamide,
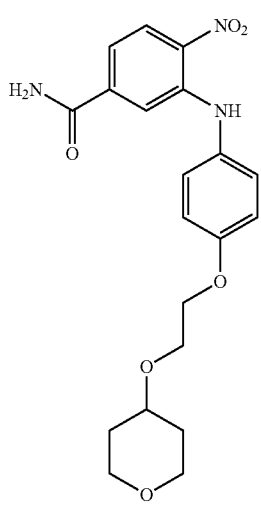 [SMILES: NC(=O)c1ccc([N+](=O)[O-])c(Nc2ccc(OCCOC3CCOCC3)cc2)c1]
(6) 4-acetyl-3-{4-[2-(tetrahydrofuran-3-yloxy)ethoxy]phenoxy}benzamide,
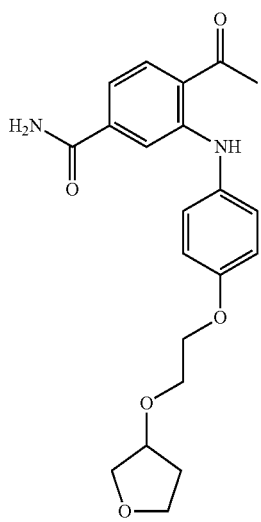
(7) 4-acetyl-3-{4-[3-(2-hydroxyethoxy)azetidin-1-yl]phenoxy}benzamide,
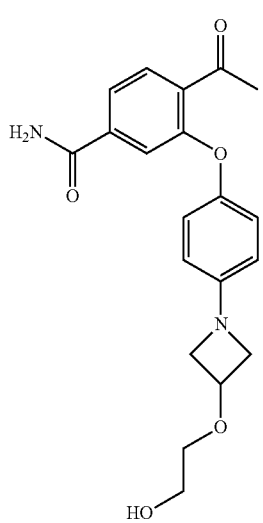 [SMILES: CC(=O)c1ccc(C(N)=O)cc1Oc1ccc(N2CC(OCCO)C2)cc1]
(8) 3-{4-[2-(tetrahydropyran-4-yloxy)ethoxy]phenoxy}-4-trifluoromethylbenzamide, and
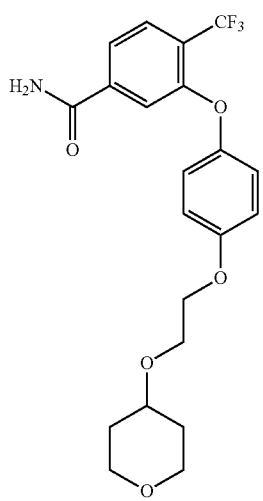 [SMILES: NC(=O)c1ccc(C(F)(F)F)c(Oc2ccc(OCCOC3CCOCC3)cc2)c1]

(9) 4-(1-fluorovinyl)-3-{4-[2-(tetrahydropyran-4-yloxy)ethoxy]phenoxy}benzamide

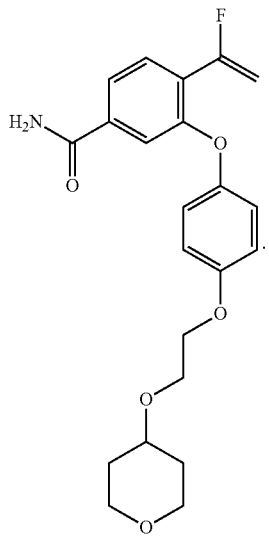 [SMILES: C=C(F)c1ccc(C(N)=O)cc1Oc1ccc(OCCOC2CCOCC2)cc1]

The method of the above-mentioned [12] or [13] wherein the aforementioned cancer is at least one kind selected from the group consisting of breast cancer, pancreatic cancer, bladder cancer, prostate cancer, esophageal cancer, stomach cancer, uterine cancer, ovarian cancer, brain tumor, colorectal cancer, hematologic cancer, liver cancer, skin cancer, lung cancer and thyroid cancer.

A compound represented by the formula (I):

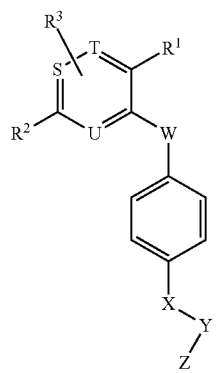

(I)

[wherein each substituent is as defined below:

$R^1$:

a cyano group, a C1-6 alkylcarbonyl group, a C1-6 alkylcarbonylamino group, a nitro group, a halogeno C1-6 alkyl group, a C2-6 alkenyl group, a halogeno C2-6 alkenyl group, a carbamoyl group or a hydroxy C1-6 alkyl group $R^2$:

a C1-6 alkoxy group, a carbamoyl group, a C1-6 alkylaminocarbonyl group or a C1-6 alkylcarbonyl group $R^3$:

a hydrogen atom or a halogen atom

S, T and U:

when any one of S, T and U is =N—, others are =CH— (=C— when $R^3$ is substituted); or all of S, T and U are =CH— (=C— when $R^3$ is substituted)

W:

—NH—, —O— or —S—

X:

a single bond, -saturated heterocyclyl-, —CH$_2$—(CH$_2$)$_n$—, —O—(CH$_2$)$_n$—, —(CH$_2$)$_n$—O— or —CH=CH—(CH$_2$)$_n$— n:

any one integer selected from 1-4

Y:

a single bond, —O— or —CO—

Z:

a hydrogen atom, a saturated heterocyclic group optionally substituted by any group selected from substituent group α or a C1-6 alkyl group optionally substituted by any group selected from substituent group α substituent group α:

a saturated heterocyclic group, a hydroxy C1-6 alkyl group, an aminosulfonylamino group, a carboxy group, a hydroxy group, a C1-6 alkoxy group, a C1-6 alkyl group], or a pharmaceutically acceptable salt thereof, for preventing and/or treating cancer.

The compound or a pharmaceutically acceptable salt thereof of the above-mentioned [15] wherein the compound represented by the formula (I) is at least one compound selected from the group consisting of (1) 3-{4-[3-(2-hydroxyethoxy)azetidin-1-yl]phenylamino}-N-methyl-4-nitrobenzamide,

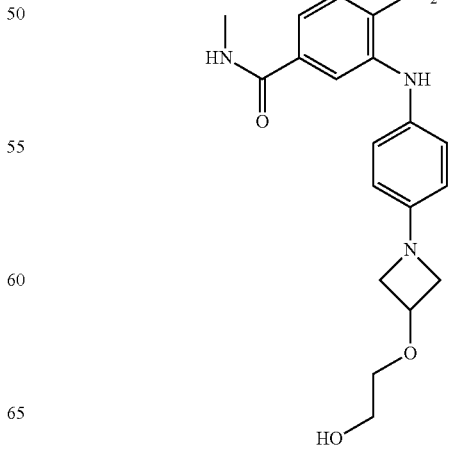

(2) 3-{4-[3-(2-hydroxyethoxy)azetidin-1-yl]phenylamino}-4-nitrobenzamide,
(4) 4-acetyl-3-{4-[2-(2-isopropoxyethoxy)ethoxy]phenoxy}benzamide,
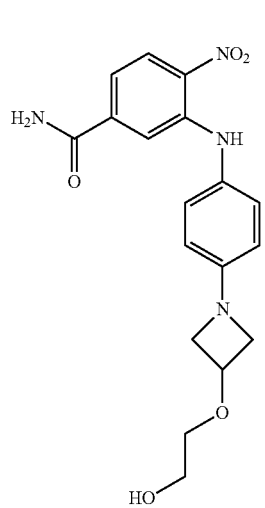
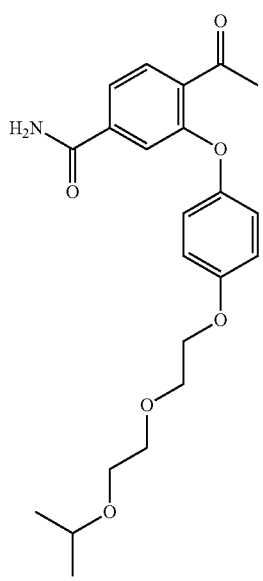
(3) 4-acetyl-3-{4-[2-(tetrahydropyran-4-yloxy)ethoxy]phenoxy}benzamide,
(5) 4-nitro-3-{4-[2-(tetrahydropyran-4-yloxy)ethoxy]phenylamino}benzamide,
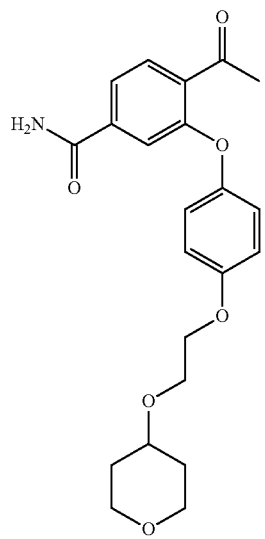
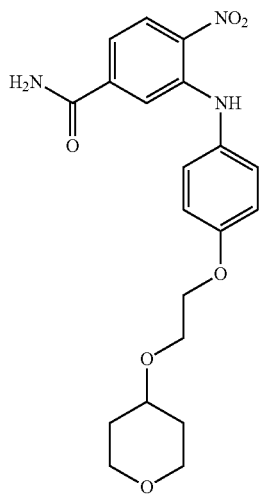

(6) 4-acetyl-3-{4-[2-(tetrahydrofuran-3-yloxy)ethoxy]phenoxy}benzamide,

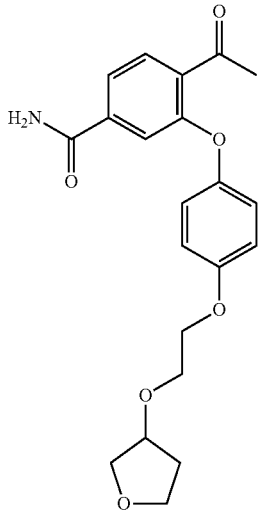

(7) 4-acetyl-3-{4-[3-(2-hydroxyethoxy)azetidin-1-yl]phenoxy}benzamide,

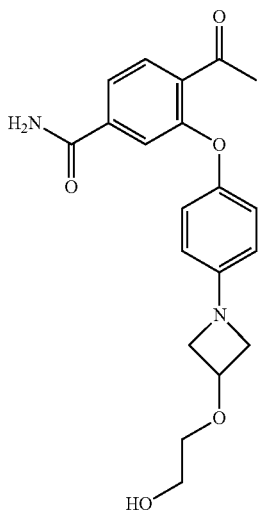 [SMILES: CC(=O)c1ccc(C(N)=O)cc1Oc1ccc(N2CC(OCCO)C2)cc1]

(8) 3-{4-[2-(tetrahydropyran-4-yloxy)ethoxy]phenoxy}-4-trifluoromethylbenzamide, and

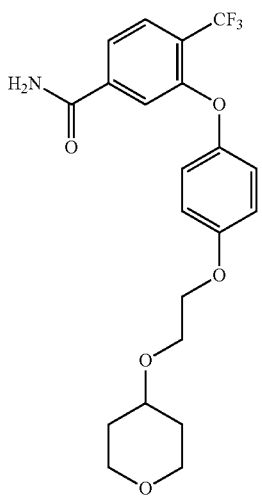 [SMILES: NC(=O)c1ccc(C(F)(F)F)c(Oc2ccc(OCCOC3CCOCC3)cc2)c1]

(9) 4-(1-fluorovinyl)-3-{4-[2-(tetrahydropyran-4-yloxy)ethoxy]phenoxy}benzamide

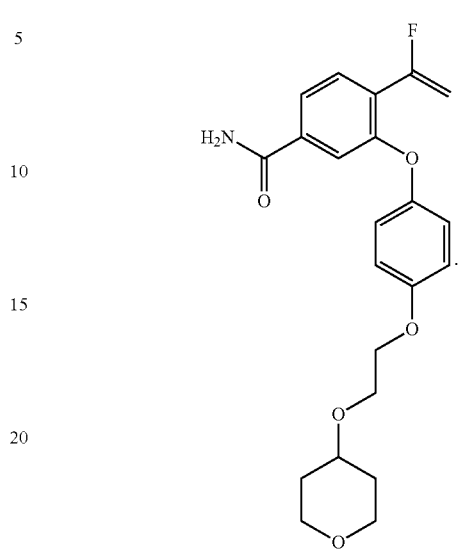

The compound of the above-mentioned [15] or [16] or a pharmaceutically acceptable salt thereof wherein the aforementioned cancer is at least one kind selected from the group consisting of breast cancer, pancreatic cancer, bladder cancer, prostate cancer, esophageal cancer, stomach cancer, uterine cancer, ovarian cancer, brain tumor, colorectal cancer, hematologic cancer, liver cancer, skin cancer, lung cancer and thyroid cancer.

Effect of the Invention

The compound (I) of the present invention has a superior inhibitory activity against CDK8 and/or CDK19. Therefore, a medicament containing the compound (I) of the present invention as an active ingredient can be used as a CDK8 and/or CDK19 inhibitor and is useful as a prophylaxis agent and/or a therapeutic agent for various diseases associated with CDK8 and/or CDK19, particularly, cell proliferative diseases such as cancer and the like.

DESCRIPTION OF EMBODIMENTS

The present invention is explained in detail in the following.

The meanings of the terms used for the indication of the compound such as substituent and the like in the present specification are as described below.
Halogen Atom:
fluorine atom, chlorine atom, bromine atom or iodine atom
C1-C6 Alkyl Group:
linear or branched chain alkyl group having 1 to 6 carbon atoms, preferably methyl group, ethyl group, propyl group, isopropyl group, isobutyl group or tert-butyl group
C1-C6 Alkylcarbonyl Group:
group wherein the above-mentioned C1-C6 alkyl group is bonded to carbonyl group, preferably acetyl group, ethylcarbonyl group, propylcarbonyl group, isopropylcarbonyl group or butylcarbonyl group
C1-C6 Alkoxy Group:
group wherein the above-mentioned C1-C6 alkyl group is bonded to oxygen atom, preferably methoxy group, ethoxy group, propoxy group, isopropoxy group or t-butoxy group C1-C6 Alkylcarbonylamino Group:
group wherein the above-mentioned C1-C6 alkyl group is bonded to carbonylamino group, preferably acetylamino group, ethylcarbonylamino group, propylcarbonylamino group, isopropylcarbonylamino group or butylcarbonylamino group Halogeno C1-C6 Alkyl Group:
group wherein the above-mentioned C1-C6 alkyl group is substituted by 1-9 (preferably 1-6, more preferably 1-3) halogen atoms, for example, fluoromethyl group, difluoromethyl group, trifluoromethyl group, fluoroethyl group, difluoroethyl group, trifluoroethyl group, fluoropropyl group, difluoropropyl group, trifluoropropyl group, fluorobutyl group, difluorobutyl group, trifluorobutyl group, fluoropentyl group, difluoropentyl group, trifluoropentyl group, fluorohexyl group, difluorohexyl group, trifluorohexyl group, pentafluoroethyl group, hexafluoropropyl group, nonafluorobutyl group, chloromethyl group, dichloromethyl group, trichloromethyl group, chloroethyl group, dichloroethyl group, trichloroethyl group, chloropropyl group, dichloropropyl group or trichloropropyl group Hydroxy C1-C6 Alkyl Group:
group wherein one hydroxy group is bonded to the above-mentioned C1-C6 alkyl group, preferably 1-hydroxymethyl group, 1-hydroxyethyl group, 1-hydroxypropyl group, 2-hydroxyethyl group or 3-hydroxypropyl group C1-C6 Alkylaminocarbonyl Group:
group wherein the above-mentioned C1-C6 alkyl group is bonded to aminocarbonyl group, preferably methylaminocarbonyl group or ethylaminocarbonyl group C2-6 Alkenyl Group:
linear or branched chain alkenyl group having 2 to 6 carbon atoms, for example, vinyl group, 1-propenyl (allyl) group, 2-propenyl group, isopropenyl group, 2-methyl-1-propenyl group, 1-butenyl group, 2-butenyl group, 3-butenyl group, 2-buten-2-yl group, 3-methyl-2-butenyl group, 3-methyl-2-buten-2-yl group, 1-pentenyl group, 2-pentenyl group, 3-pentenyl group, 4-pentenyl group, 5-pentenyl group, 2-penten-2-yl group, 2-penten-3-yl group, 4-methyl-1-pentenyl group, 1-hexenyl group, 2-hexenyl group, 3-hexenyl group Halogeno C2-C6 Alkenyl Group:
group wherein linear or branched chain alkenyl group having 2 to 6 carbon atoms is substituted by 1-5 (preferably 1-3, more preferably 1 or 2) halogen atoms, for example, 1-fluorovinyl group, 1-chlorovinyl group, 1-bromovinyl group, trifluorovinyl group, trichlorovinyl group or tribromovinyl group Saturated Heterocyclic Group:
saturated 5-7 membered heterocyclic group containing 1 to 3 sulfur atoms, oxygen atoms and/or nitrogen atoms, for example, tetrahydropyranyl group, tetrahydrofuranyl group, oxotetrahydrofuranyl group, morpholinyl group, thiomorpholinyl group, 1-oxothiomorpholinyl group, 1,1-dioxothiomorpholinyl group, pyrrolidinyl group, pyrrolinyl group, imidazolidinyl group, pyrazolidinyl group, piperidinyl group, piperazinyl group, oxazolidinyl group, isoxazolidinyl group, thiazolidinyl group, 1,4-dioxanyl group or 1,1-dioxohexahydrothiopyranyl group.

The "-saturated heterocyclyl-" shows a divalent group derived from a saturated heterocycle, and examples of the saturated heterocycle include azetidine ring, tetrahydropyran ring, tetrahydrofuran ring, morpholine ring, thiomorpholine ring, 1-oxothiomorpholine ring, 1,1-dioxothiomorpholine ring, pyrrolidine ring, pyrroline ring, imidazolidine ring, pyrazolidine ring, piperidine ring, piperazine ring, oxazolidine ring, isoxazolidine ring, and thiazolidine ring.

The "optionally substituted" means unsubstituted or any of 1 to 3 substitutions. When di- or tri-substituted, the respective substituents may be the same or different.

The definition of each symbol in the formula (I) is described in detail below.

$R^1$ is cyano group, C1-6 alkylcarbonyl group, C1-6 alkylcarbonylamino group, nitro group, halogeno C1-6 alkyl group, C2-6 alkenyl group, halogeno C2-6 alkenyl group, carbamoyl group or hydroxy C1-6 alkyl group.

In another embodiment of the present invention, R is cyano group, C1-6 alkylcarbonyl group, C1-6 alkylcarbonylamino group, nitro group, halogeno C1-6 alkyl group, halogeno C2-6 alkenyl group, carbamoyl group or hydroxy C1-6 alkyl group.

As "C1-6 alkylcarbonyl group" for R, methylcarbonyl group (acetyl group) is preferable.

As "C1-6 alkylcarbonylamino group" for $R^1$, methylcarbonylamino group (acetylamino group), ethylcarbonylamino group or propylcarbonylamino group is preferable.

As "halogeno C1-6 alkyl group" for $R^1$, fluoromethyl group, difluoromethyl group, trifluoromethyl group, 1-fluoroethyl group or 1,1-difluoroethyl group is preferable.

As "C2-6 alkenyl group" for $R^1$, vinyl group is preferable.

As "halogeno C2-6 alkenyl group" for $R^1$, 1-fluorovinyl group is preferable.

As "hydroxy C1-6 alkyl group" for $R^1$, hydroxymethyl group or 1-hydroxyethyl group is preferable.

$R^1$ is preferably cyano group, acetyl group, acetylamino group, ethylcarbonylamino group, propylcarbonylamino group, nitro group, fluoromethyl group, trifluoromethyl group, 1,1-difluoroethyl group, 1-fluoroethyl group, difluoromethyl group, vinyl group, 1-fluorovinyl group, carbamoyl group, hydroxymethyl group or 1-hydroxyethyl group, more preferably, cyano group, acetyl group, acetylamino group, nitro group, trifluoromethyl group, 1,1-difluoroethyl group, 1-fluoroethyl group, difluoromethyl group, carbamoyl group or 1-hydroxyethyl group.

In another embodiment of the present invention, $R^1$ is preferably cyano group, acetyl group, acetylamino group, ethylcarbonylamino group, propylcarbonylamino group, nitro group, fluoromethyl group, trifluoromethyl group, 1,1-difluoroethyl group, 1-fluoroethyl group, difluoromethyl group, 1-fluorovinyl group, carbamoyl group, hydroxymethyl group or 1-hydroxyethyl group, more preferably, cyano group, acetyl group, acetylamino group, nitro group, trifluoromethyl group, 1,1-difluoroethyl group, 1-fluoroethyl group, difluoromethyl group, carbamoyl group or 1-hydroxyethyl group.

$R^2$ is C1-6 alkoxy group, carbamoyl group, C1-6 alkylaminocarbonyl group or C1-6 alkylcarbonyl group.

As "C1-6 alkoxy group" for $R^2$, methoxy group is preferable.

As "C1-6 alkylaminocarbonyl group" for $R^2$, methylaminocarbonyl group, ethylaminocarbonyl group is preferable.

As "C1-6 alkylcarbonyl group" for $R^2$, methylcarbonyl group (acetyl group) is preferable.

$R^2$ is preferably methoxy group, carbamoyl group, methylaminocarbonyl group, ethylaminocarbonyl group or methylcarbonyl group (acetyl group), more preferably, methoxy group, carbamoyl group, methylaminocarbonyl group or acetyl group.

$R^3$ is a hydrogen atom or a halogen atom.

As "halogen atom" for $R^3$, fluorine atom is preferable.

$R^3$ is preferably a hydrogen atom or a fluorine atom.

As for S, T and U, when any one of S, T and U is =N—, the others are =CH— (=C— when R³ is substituted); or all of S, T and U are =CH— (=C— when R³ is substituted).

As for S, T and U, S is preferably =N—, and T and U are =CH— or all of S, T and U are =CH—, more preferably all of S, T and U are =CH—.

W is —NH—, —O— or —S—.

W is preferably —NH— or —O—.

X is a single bond, -saturated heterocyclyl-, —CH₂—(CH₂)ₙ—, —O—(CH₂)ₙ—, —(CH₂)ₙ—O— or —CH=CH—(CH₂)ₙ— [n is any one integer selected from 1-4].

In another embodiment of the present invention, X is -saturated heterocyclyl-, —CH₂—(CH₂)ₙ—, —O—(CH₂)ₙ—, —(CH₂)ₙ—O— or —CH=CH—(CH₂)ₙ— [n is any one integer selected from 1-4].

As "-saturated heterocyclyl-" for X, azetidinediyl, piperidinediyl or piperazinediyl is preferable.

When X is —CH₂—(CH₂)ₙ—, n is preferably 1 or 2, i.e., X is preferably —CH₂—CH₂— or —CH₂—CH₂—CH₂—.

When X is —O—(CH₂)ₙ—, n is preferably 1 or 2, i.e., X is preferably —O—CH₂— or —O—CH₂—CH₂—.

When X is —(CH₂)ₙ—O—, n is preferably 1, i.e., X is preferably —CH₂—O—.

When X is —CH=CH—(CH₂)ₙ—, n is preferably 1, i.e., X is preferably —CH=CH—CH₂—.

X is preferably a single bond, -saturated heterocyclyl- (e.g., azetidinediyl, piperidinediyl, piperazinediyl), —CH₂—CH₂—, —CH₂—CH₂—CH₂—, —O—CH₂—, —O—CH₂—CH₂—, —CH₂—O— or —CH=CH—CH₂—, more preferably, -saturated heterocyclyl- (e.g., azetidinediyl, piperidinediyl, piperazinediyl) or —O—CH₂—CH₂— [—O—(CH₂)ₙ—, n is 2].

In another embodiment of the present invention, X is preferably -saturated heterocyclyl- (e.g., azetidinediyl, piperidinediyl, piperazinediyl), —CH₂—CH₂—, —CH₂—CH₂—CH₂—, —O—CH₂—, —O—CH₂—CH₂—, —CH₂—O— or —CH=CH—CH₂—, more preferably -saturated heterocyclyl- (e.g., azetidinediyl, piperidinediyl, piperazinediyl) or —O—CH₂—CH₂— [—O—(CH₂)ₙ—, n is 2].

Y is a single bond, —O— or —CO—.

Y is preferably a single bond or —O—.

Z is a hydrogen atom, saturated heterocyclic group optionally substituted by any group selected from substituent group α or C1-6 alkyl group optionally substituted by any group selected from substituent group α, and the substituent group α includes saturated heterocyclic group, hydroxy C1-6 alkyl group, aminosulfonylamino group, carboxy group, hydroxy group, C1-s alkoxy group, and C1-6 alkyl group.

In another embodiment of the present invention, Z is a hydrogen atom, saturated heterocyclic group optionally substituted by any group selected from substituent group α or C1-6 alkyl group optionally substituted by any group selected from substituent group α, the substituent group α includes hydroxy C1-6 alkyl group, aminosulfonylamino group, carboxy group, hydroxy group, C1-6 alkoxy group, and C1-6 alkyl group.

As the "saturated heterocyclic group" of the "saturated heterocyclic group optionally substituted by any group selected from substituent group α" for Z, tetrahydrofuranyl group, oxotetrahydrofuranyl group, tetrahydropyranyl group, morpholinyl group, piperidinyl group, piperazinyl group, 1,4-dioxanyl group or 1,1-dioxohexahydrothiopyranyl group is preferable.

As the group selected from the substituent group α, hydroxy C1-6 alkyl group (e.g., hydroxymethyl group) or C1-6 alkyl group (e.g., methyl group) is preferable.

As the "C1-6 alkyl group" of the "C1-6 alkyl group optionally substituted by any group selected from substituent group α" for Z, methyl group, ethyl group, propyl group, isopropyl group or isobutyl group is preferable.

As the group selected from the substituent group α, saturated heterocyclic group (e.g., tetrahydrofuranyl group, morpholinyl group), aminosulfonylamino group, carboxy group, hydroxy group or C1-6 alkoxy group (e.g., isopropoxy group) is preferable.

In another embodiment of the present invention, as the group selected from the substituent group α, aminosulfonylamino group, carboxy group, hydroxy group or C1-6 alkoxy group (e.g., isopropoxy group) is preferable.

Z is preferably saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from hydrogen atom, hydroxy C1-6 alkyl group (e.g., hydroxymethyl group), and C1-6 alkyl group (e.g., methyl group) or C1-6 alkyl group (e.g., methyl group, ethyl group, propyl group, isopropyl group, isobutyl group) optionally substituted by any group selected from saturated heterocyclic group (e.g., tetrahydrofuranyl group, morpholinyl group), aminosulfonylamino group, carboxy group, hydroxy group, and C1-6 alkoxy group (e.g., isopropoxy group), more preferably C1-6 alkyl group substituted by hydroxy group (e.g., methyl group, ethyl group, propyl group, isopropyl group, isobutyl group), tetrahydrofuranyl group, tetrahydropyranyl group, piperazinyl group or morpholinyl group.

In another embodiment of the present invention, Z is preferably saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from hydrogen atom, hydroxy C1-6 alkyl group (e.g., hydroxymethyl group), and C1-6 alkyl group (e.g., methyl group) or C1-6 alkyl group (e.g., methyl group, ethyl group, propyl group, isopropyl group, isobutyl group) optionally substituted by any group selected from aminosulfonylamino group, carboxy group, hydroxy group, and C1-6 alkoxy group (e.g., so isopropoxy group), more preferably, C1-6 alkyl group substituted by hydroxy group (e.g., methyl group, ethyl group, propyl group, isopropyl group, isobutyl group), tetrahydrofuranyl group, tetrahydropyranyl group, piperazinyl group or morpholinyl group.

As preferable compound (I), the following compounds can be mentioned.

[Compound I-1-1]

Compound (I) wherein

R¹ is cyano group, acetyl group, acetylamino group, ethylcarbonylamino group, propylcarbonylamino group, nitro group, fluoromethyl group, trifluoromethyl group, 1,1-difluoroethyl group, 1-fluoroethyl group, difluoromethyl group, vinyl group, 1-fluorovinyl group, carbamoyl group, hydroxymethyl group or 1-hydroxyethyl group;

R² is methoxy group, carbamoyl group, methylaminocarbonyl group, ethylaminocarbonyl group or methylcarbonyl group (acetyl group);

R³ is a hydrogen atom or a fluorine atom;

S is =N—, and T and U are =CH— or all of S, T and U are =CH—;

W is —NH—, —O— or —S—;

X is a single bond, -saturated heterocyclyl- (e.g., azetidinediyl, piperidinediyl, piperazinediyl), —CH$_2$—CH$_2$—, —CH$_2$—CH$_2$—CH$_2$—, —O—CH$_2$—, —O—CH$_2$—CH$_2$—, —CH$_2$—O— or —CH=CH—CH$_2$—;

Y is a single bond, —O— or —CO—; and

Z is saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from hydrogen atom, hydroxy C1-6 alkyl group (e.g., hydroxymethyl group), and C1-6 alkyl group (e.g., methyl group) or C1-6 alkyl group (e.g., methyl group, ethyl group, propyl group, isopropyl group, isobutyl group) optionally substituted by any group selected from saturated heterocyclic group (e.g., tetrahydrofuranyl group, morpholinyl group), aminosulfonylamino group, carboxy group, hydroxy group, and C1-6 alkoxy group (e.g., isopropoxy group).

[Compound I-1-2]

Compound (I) wherein

R$^1$ is cyano group, acetyl group, acetylamino group, ethylcarbonylamino group, propylcarbonylamino group, nitro group, fluoromethyl group, trifluoromethyl group, 1,1-difluoroethyl group, 1-fluoroethyl group, difluoromethyl group, 1-fluorovinyl group, carbamoyl group, hydroxymethyl group or 1-hydroxyethyl group;

R$^2$ is methoxy group, carbamoyl group, methylaminocarbonyl group, ethylaminocarbonyl group or methylcarbonyl group (acetyl group);

R$^3$ is a hydrogen atom or a fluorine atom;

S is =N—, and T and U are =CH— or all of S, T and U are =CH—;

W is —NH—, —O— or —S—;

X is -saturated heterocyclyl- (e.g., azetidinediyl, piperidinediyl, piperazinediyl), —CH$_2$—CH$_2$—, —CH$_2$—CH$_2$—CH$_2$—, —O—CH$_2$—, —O—CH$_2$—CH$_2$—, —CH$_2$—O— or —CH=CH—CH$_2$—;

Y is a single bond, —O— or —CO—; and

Z is saturated heterocyclic group (e.g., tetrahydrofuranyl group, oxotetrahydrofuranyl group, tetrahydropyranyl group, morpholinyl group, piperidinyl group, piperazinyl group, 1,4-dioxanyl group, 1,1-dioxohexahydrothiopyranyl group) optionally substituted by any group selected from hydrogen atom, hydroxy C1-6 alkyl group (e.g., hydroxymethyl group), and C1-6 alkyl group (e.g., methyl group) or C1-6 alkyl group (e.g., methyl group, ethyl group, propyl group, isopropyl group, isobutyl group) optionally substituted by any group selected from aminosulfonylamino group, carboxy group, hydroxy group, and C1-6 alkoxy group (e.g., isopropoxy group).

[Compound I-2]

Compound (I) wherein

R$^1$ is cyano group, acetyl group, acetylamino group, nitro group, trifluoromethyl group, 1,1-difluoroethyl group, 1-fluoroethyl group, difluoromethyl group, carbamoyl group or 1-hydroxyethyl group;

R$^2$ is methoxy group, carbamoyl group, methylaminocarbonyl group or acetyl group;

R$^3$ is a hydrogen atom or a fluorine atom;

all of S, T and U are =CH—;

W is —NH— or —O—;

X is -saturated heterocyclyl- (e.g., azetidinediyl, piperidinediyl, piperazinediyl) or —O—CH$_2$—CH$_2$—;

Y is a single bond or —O—; and

Z is C1-6 alkyl group (e.g., methyl group, ethyl group, propyl group, isopropyl group, isobutyl group) substituted by hydroxy group, tetrahydrofuranyl group, tetrahydropyranyl group, piperazinyl group or morpholinyl group.

[Compound I-3]

Compound (I) wherein

R$^1$ is acetyl group, acetylamino group, nitro group, trifluoromethyl group, difluoromethyl group, carbamoyl group or 1-hydroxyethyl group;

R$^2$ is methoxy group, carbamoyl group or acetyl group;

R$^3$ is a hydrogen atom or a fluorine atom;

S is =N—, and T and U are =CH— or all of S, T and U are =CH—;

W is —NH— or —O—;

X is -saturated heterocyclyl- (e.g., azetidinediyl, piperidinediyl, piperazinediyl) or —O—CH$_2$—CH$_2$—;

Y is a single bond or —O—; and

Z is C1-6 alkyl group (e.g., ethyl group, isobutyl group) substituted by any group selected from carboxy group, hydroxy group, and C1-6 alkoxy group (e.g., isopropoxy group), tetrahydrofuranyl group, tetrahydropyranyl group or 1,1-dioxohexahydrothiopyranyl group.

Specific preferable examples of compound (I) include the compounds of Examples 1-99 described in the following Table 1-1 to Table 1-25 (hereinafter to be also referred to as compounds 1-99). Among them, (1) 3-{4-[3-(2-hydroxyethoxy)azetidin-1-yl]phenylamino}-N-methyl-4-nitrobenzamide (compound 48), (2) 3-{4-[3-(2-hydroxyethoxy)azetidin-1-yl]phenylamino}-4-nitrobenzamide (compound 5), (3) 4-acetyl-3-{4-[2-(tetrahydropyran-4-yloxy)ethoxy]phenoxy}benzamide (compound 32), (4) 4-acetyl-3-{4-[2-(2-isopropoxyethoxy)ethoxy]phenoxy}benzamide (compound 33), (5) 4-nitro-3-{4-[2-(tetrahydropyran-4-yloxy)ethoxy]phenylamino}benzamide (compound 50), (6) 4-acetyl-3-{4-[2-(tetrahydrofuran-3-yloxy)ethoxy]phenoxy}benzamide (compound 67), (7) 4-acetyl-3-{4-[3-(2-hydroxyethoxy)azetidin-1-yl]phenoxy}benzamide (compound 28), (8) 3-{4-[2-(tetrahydropyran-4-yloxy)ethoxy]phenoxy}-4-trifluoromethylbenzamide (compound 64), and (9) 4-(1-fluorovinyl)-3-{4-[2-(tetrahydropyran-4-yloxy)ethoxy]phenoxy}benzamide (compound 84) are preferable.

To "prevent" means, for example, administering a medicament containing compound (I) of the present invention to a patient who is considered to have a high risk of developing a disease or symptom because of some factor related to the disease or symptom but has not developed the disease or symptom or a patient who has developed the disease or symptom but does not have a subjective symptom, or administering a medicament containing compound (I) of the present invention to a patient who underwent a treatment of the disease or symptom and is feared to have recurrence of the disease or symptom.

To "treat" means curing a disease or symptom.

A "pharmaceutically acceptable salt thereof" shows a salt that can be used as a medicament. When compound (I) of the present invention has acidic group or basic group, since it can be converted to a basic salt or acidic salt by reacting with a base or acid, the salt thereof is used.

A pharmaceutically acceptable "basic salt" of compound (I) of the present invention is preferably an alkali metal salt such as sodium salt, potassium salt, and lithium salt; alkaline earth metal salt such as magnesium salt, and calcium salt; a salt with organic base such as N-methylmorpholine salt, triethylamine salt, tributylamine salt, diisopropylethylamine salt, dicyclohexylamine salt, N-methylpiperidine salt, pyridine salt, 4-pyrrolidinopyridine salt, and picoline salt or an amino acid salt such as glycine salt, lysine salt, arginine salt, ornithine salt, glutamic acid salt, and aspartic acid salt, preferably an alkali metal salt.

A pharmaceutically acceptable "acidic salt" of compound (I) of the present invention is preferably inorganic acid salt such as hydrohalide (e.g., hydrofluoride, hydrochloride, hydrobromide, hydroiodide), nitrate, perchlorate, sulfate, phosphate and the like; organic acid salt such as lower alkanesulfonate (e.g., methanesulfonate, trifluoromethanesulfonate, ethanesulfonate), arylsulfonate (e.g., benzenesulfonate, p-toluenesulfonate), acetate, malate, fumarate, succinate, citrate, ascorbate, tartrate, oxalate, maleate and the like; or amino acid salt such as glycine salt, lysine salt, arginine salt, ornithine salt, glutamic acid salt, aspartic acid salt, most preferably hydrohalide (particularly, hydrochloride).

The compound (I) of the present invention or a pharmacologically acceptable salt thereof sometimes absorbs moisture, is attached with adsorbed water or becomes hydrate by being left in the air or recrystallized, and the present invention also encompasses such various hydrates, solvates and compounds with crystal polymorphism.

The compound (I) of the present invention, a pharmacologically acceptable salt thereof or a solvate thereof may contain, depending on the kind and combination of substituents, various isomers such as geometrical isomer (e.g., cis form, trans form and the like), tautomer, optical isomer (e.g., d form, l form and the like), and the like. Unless particularly limited, the compound (I) of the present invention also encompasses all those isomers, stereoisomers and mixtures of these isomers and stereoisomers at any ratio. The mixtures of these isomers and stereoisomers can be isolated by a known separation means. The above-mentioned isomer can also be produced by asymmetric synthesis.

The compound (I) of the present invention also includes labeled compounds, that is, the compound of the present invention wherein one or more atoms are substituted by an isotope (e.g., $^2H$, $^3H$, $^{13}C$, $^{14}C$, $^{35}S$ etc.).

The present invention also encompasses a pharmaceutically acceptable prodrug of compound (I) of the present invention. The pharmaceutically acceptable prodrug is a compound having a group convertible to amino group, a hydroxy group, a carboxy group and the like of the compound of the present invention by hydrolysis or under physiological conditions. A group that forms such prodrug includes, for example, the groups described in Prog. Med., vol. 5, pages 2157-2161, 1985, and "Development of Pharmaceutical Product" (Hirokawa-Shoten Ltd., 1990) vol. 7, molecule design, pages 163-198. More specific examples of the prodrug include, when compound (I) of the present invention has an amino group, the compound wherein the amino group thereof is acylated, alkylated, phosphorylated (e.g., compounds wherein the amino group thereof is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated) and the like, when compound (I) of the present invention has a hydroxy group, the compound wherein a hydroxy group thereof is acylated, alkylated, phosphorylated or borated (e.g., compounds wherein the hydroxy group thereof is acetylated, palmitoylated, propanoylated, pivaloylated, succinylated, fumarylated, alanylated or dimethylaminomethylcarbonylated, etc.), and the like. When compound (I) of the present invention contains a carboxy group, the compound wherein a carboxy group thereof is esterified or amidated (e.g., compounds wherein the carboxy group thereof is ethyl esterified, phenyl esterified, carboxymethyl esterified, dimethylaminomethyl esterified, pivaloyloxymethyl esterified, 1-ethoxycarbonyloxyethyl esterified, 1-cyclohexyloxycarbonyloxyethyl esterified, amidated or methylamidated etc.) and the like can be mentioned.

The compound (I) of the present invention can be used for preventing or treating diseases associated with CDK8 in mammals (e.g., mouse, rat, hamster, rabbit, cat, dog, bovine, sheep, monkey, human).

The "disease associated with cyclin-dependent kinase (CDK) 8" means a disease or condition involving cell proliferation due to promoted function of CDK8. Examples of such disease or condition involving cell proliferation include cancer, autoimmune disease, inflammatory disease and the like. Among these, cancer caused by rapid tumor proliferation due to CDK8 is a representative disease.

Examples of the cancer for which compound (I) of the present invention is applied include colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophageal cancer, stomach cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testicular cancer, prostate cancer (e.g., hormone-dependent prostate cancer, hormone non-dependent prostate cancer, castration therapy resistant prostate cancer), liver cancer (e.g., hepatoma, primary liver cancer, extrahepatic bile duct cancer), thyroid cancer (e.g., medullary thyroid carcinoma), kidney cancer (e.g., renal cell carcinoma, transitional cell carcinoma of renal pelvis and ureter), uterine cancer (e.g., endometrial carcinoma, cervix cancer, uterine body cancer, uterine sarcoma), gestational choriocarcinoma, brain tumor (e.g., medulloblastoma, glioma, pineal astrocytoma, pilocytic astrocytoma, diffuse astrocytoma, anaplastic astrocytoma, pituitary adenoma), retina blastoma, skin cancer (e.g., basal cell tumor, malignant melanoma), sarcoma (e.g., rhabdomyosarcoma, leiomyosarcoma, soft tissue sarcoma, spindle cell sarcoma), malignant bone tumor, bladder cancer, hematologic cancer (e.g., multiple myeloma, leukemia (e.g., acute myeloid leukemia), malignant lymphoma, Hodgkin's disease, chronic myeloproliferative disorder), cancer of unknown primary and the like.

Among these, compound (I) of the present invention is effective for at least one kind of cancer selected from the group consisting of breast cancer, pancreatic cancer, bladder cancer, prostate cancer, esophageal cancer, stomach cancer, uterine cancer, ovarian cancer, brain tumor, colorectal cancer (e.g., colorectal cancer, rectal cancer), hematologic cancer (e.g., acute myeloid leukemia, multiple myeloma), liver cancer (e.g., hepatoma), skin cancer, lung cancer and thyroid cancer.

The compound (I) of the present invention can be produced by reference to a known method described in WO 2015/030189 (patent document 7).

The cyclin-dependent kinase 8/19 inhibitor of the present invention contains compound (I) as an active ingredient and can be used as a medicament for preventing and/or treating a disease associated with CDK8 and/or CDK19 (that is, a prophylaxis agent and/or a therapeutic agent for a disease associated with CDK8 and/or CDK19). In this case, compound (I) of the present invention can be orally or parenterally administered to mammals (preferably, human) as it is or as a medicament containing a pharmacologically acceptable carrier.

The administration route is not particularly limited and can be appropriately selected according to the object of treatment. Examples of the dosage form of the medicament of the present invention (that is, cyclin-dependent kinase 8 inhibitor) include oral preparations such as tablet (including sugar-coated tablet, film-coated tablet, sublingual tablet, buccal tablet, orally quick disintegrating tablet), pill, granule, powder, capsule (including soft capsule, microcapsule), syrup, emulsion, suspension, film (e.g., orally disintegrable film, mouth cavity mucosa patch film) and the like. Examples of the dosage form of the medicament of the present invention also include parenteral agents such as injection, drip transfusion, transdermal preparation, suppository, ointment, nasal preparation, pulmonary preparation, eye drop and the like. In addition, the medicament of the present invention may be a controlled-release preparation such as immediate-release preparation, sustained-release preparation and the like.

The medicament of the present invention can be produced by a known production method (e.g., the method described in the Japanese Pharmacopoeia) generally used in the technical field of pharmaceutical formulation. In addition, the medicament of the present invention can appropriately contain, where necessary, a proper amount of additives generally used in the pharmaceutical field such as excipient, binder, disintegrant, lubricant, sweetening agent, surfactant, suspending agent, emulsifier, colorant, preservative, aromatic, corrigent, stabilizer, thickener and the like.

As the aforementioned pharmacologically acceptable carrier, these additives can be mentioned.

For example, tablets can be produced using excipient, binder, disintegrant, lubricant and the like, and pills and granules can be produced using excipient, binder and disintegrant. In addition, powders and capsules can be produced using excipient and the like, syrup can be produced using sweetening agent and the like, and emulsions and suspensions can be produced using suspending agent, surfactant, emulsifier and the like.

Examples of the excipient include lactose, sucrose, glucose, starch, saccharose, crystalline cellulose, *Glycyrrhiza uralensis*, mannitol, sodium hydrogen carbonate, calcium phosphate and calcium sulfate.

Examples of the binder include 5 to 10 wt % starch glue liquid, 10 to 20 wt % gum arabic solution or gelatin solution, 1 to 5 wt % tragacanth solution, carboxymethylcellulose solution, sodium alginate solution and glycerol.

Examples of the disintegrant include starch and calcium carbonate.

Examples of the lubricant include magnesium stearate, stearic acid, calcium stearate and purified talc.

Examples of the sweetening agent include glucose, fructose, invert sugar, sorbitol, xylitol, glycerol and simple syrup.

Examples of the surfactant include sodium lauryl sulfate, polysorbate 80, sorbitan mono fatty acid ester and polyoxyl stearate 40.

Examples of the suspending agent include gum arabic, sodium alginate, sodium carboxymethylcellulose, methylcellulose and bentonite.

Examples of the emulsifier include gum arabic, tragacanth, gelatin and polysorbate 80.

For example, when the medicament of the present invention is a tablet, the tablet can be produced according to a method known per se by adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol 6000) to the compound of the present invention, compression molding the mixture and coating the tablet where necessary by a method known per se for the purpose of masking of taste, enteric coating or sustainability. As a coating agent to be used for the coating, for example, hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) and dye (e.g., red iron oxide, titanium dioxide) are used.

The aforementioned injection includes intravenous injection, subcutaneous injection, intradermal injection, muscular injection, intraperitoneal injection, drip injection and the like.

Such injection can be prepared by a method known per se, that is, by dissolving, suspending or emulsifying the compound (I) of the present invention in an aseptic aqueous solution or oily solution. Examples of the aqueous solution include saline, isotonic solution containing glucose and other auxiliary agents (e.g., D-sorbitol, D-mannitol, sodium chloride), and the like. The aqueous solution may contain suitable solubilizing agents, for example, alcohol (e.g., ethanol), polyalcohol (e.g., propylene glycol, polyethylene glycol) and non-ionic surfactant (e.g., polysorbate 80, HCO-50). Examples of the oily solution include sesame oil, soybean oil and the like. The oily solution may contain suitable solubilizing agents. Examples of the solubilizing agent include benzyl benzoate, benzyl alcohol and the like. The injection may be blended with buffering agents (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and the like. The prepared injection is generally filled in an ampoule.

In addition to the above, a preferable preparation can be appropriately formed by utilizing a conventional method.

The content of the additive in the medicament of the present invention varies depending on the form of the preparation and is generally about 1 to about 99.9 wt %, preferably about 10 to about 90 wt %, relative to the whole preparation.

The daily dose of compound (I) of the present invention varies depending on the patient's condition and body weight, the kind of compound (I), administration route and the like. For example, for oral administration to patients for the treatment of cancer, the daily dose of the compound of the present invention is about 1 to about 1000 mg, preferably about 3 to about 300 mg, further preferably about 10 to about 200 mg, for an adult (body weight about 60 kg), and this dose can be administered at once or in several portions.

When compound (I) of the present invention is parenterally administered, it is generally administered in the form of a liquid (e.g., injection). The single dose of the compound of the present invention varies depending on the subject of administration, target organ, symptom, administration method and the like. Generally, for example, about 0.01 to about 100 mg, preferably about 0.01 to about 50 mg, more preferably about 0.01 to about 20 mg per 1 kg body weight, of the compound of the present invention is preferably administered by intravenous injection.

The compound (I) of the present invention can be used in combination with other drugs. Specifically, compound (I) of the present invention can be used in combination with drugs such as chemotherapeutic agent, hormonal therapeutic agent, molecular targeting agent, anti-inflammatory agent, immunosuppressant, immunotherapeutic agent and the like. In the following, drugs that can be used in combination with the compound of the present invention are recited as concomitant drugs.

Examples of the "chemotherapeutic agent" include alkylating agent (e.g., nitrogen mustard, nitrogen mustard-N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin etc.), antimetabolite (e.g., mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofour, gallocitabine, emitefur, capecitabine), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine etc.), antitumor antibiotics (e.g., actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride etc.), plant-derived antitumor drug (e.g., etoposide, etoposide phosphate, vinblastine sulfate, vincristine sulfate, vindesine sulfate, teniposide, paclitaxel, docetaxel, vinorelbine etc.) and the like.

As the "hormonal therapeutic agent", fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testrolactone, aminoglutethimide, LH-RH agonist (e.g., goserelin acetate, buserelin, leuprorelin), droloxifene, epitiostanol, ethinylestradiol sulfonate, aromatase inhibitor (e.g., fadrozole hydrochloride, anastrozole, letrozole, exemestane, vorozole, formestane), anti-androgen (e.g., flutamide, bicalutamide, nilutamide), 5α-reductase inhibitor (e.g., finasteride, epristeride), adrenocorticotropic hormone drug (e.g., dexamethasone, prednisolone, betamethasone, triamcinolone), androgen synthesis inhibitor (e.g., abiraterone), retinoid and drugs that retard retinoid metabolism (e.g., liarozole) and the like are used.

As the "molecular targeting agent", tositumomab, ibritumomab, alemtuzumab, axitinib, bevacizumab, afatinib, bortezomib, bosutinib, carfilzomib, cetuximab, dasatinib, denosumab, edrecolomab, erlotinib, everolimus, vismodegib, gefitinib, gemtuzumab ozogamicin, imatinib, ipirimumab, lapatinib, lenalidomide, nilotinib, nimotuzumab, olaparib, panitumumab, pazopanib, pertuzumab, rituximab, siltuximab, sorafenib, sunitinib, tamibarotene, temsirolimus, thalidomide, trastuzumab, tretinoin, vandetanib, vorinostat, cabozantinib, trametinib, dabrafenib, alectinib, ceritinib, ibrutinib, palbociclib, regorafenib and the like are used.

Examples of the "anti-inflammatory agent" include nonsteroidal antiinflammatory agents (e.g., acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, oxaprozin, flurbiprofen, fenbufen, pranoprofen, floctafenine, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, ketoprofen, naproxen, oxymorphone, meloxicam, celecoxib, rofecoxib or a salt thereof etc.), steroidal antiinflammatory agents (e.g., dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclomethasone dipropionate, estriol etc.) and the like.

Examples of the "immunosuppressant" include glucocorticoid, cyclosporine, tacrolimus, sirolimus, temsirolimus, everolimus, infliximab, adalimumab, anti-CD52 monoclonal antibody, anti-CD3 monoclonal antibody (e.g., OKT3) and the like.

As the "immunotherapeutic agent", biological response modifier (e.g., picibanil, krestin, schizophyllan, lentinan, ubenimex, interferon, interleukin, macrophage colony stimulating factor, granulocyte colony stimulating factor, erythropoietin, lymphotoxin, BCG vaccine, *Corynebacterium parvum*, levamisole, polysaccharide K, procodazole, anti-CTLA4 antibody) and the like are used.

The administration period of compound (I) of the present invention and a concomitant drug is not limited, and compound (I) of the present invention and the concomitant drug can be administered to an administration subject simultaneously, or may be administered at different times. In addition, a single preparation obtained by simultaneously formulating compound (I) of the present invention and the concomitant drug may be administered, or two kinds of preparations obtained by separately formulating compound (I) of the present invention and the concomitant drug may be administered simultaneously or at different times by the same administration route or separate administration routes.

As the data in the Example shows, compound (I) of the present invention has a cyclin-dependent kinase 8/19 inhibitory action. Such pharmacological action means that compound (I) of the present invention is useful as an agent for preventing and/or treating diseases associated with cyclin-dependent kinase 8 and/or 19, particularly, an agent for preventing and/or treating cancer, a cancer proliferation inhibitor, a cancer metastasis inhibitor or the like.

EXAMPLE

The present invention is explained in detail in the following by referring to Examples, Experimental Examples and Formulation Examples. However, the present invention is not limited by the following Examples. Unless particularly limited, the reagents and materials to be used are commercially available.

In the following Experimental Examples 1 and 2, the test compound (i.e., compound (I)) used was selected from compounds 1-99 (compounds of Examples 1-99 described in WO 2015/030189 (patent document 7)).

The chemical structures and instrumental analysis data of the compounds of Examples 1-99 (hereinafter to be also referred to as compounds 1-99) produced by the method described in the Example of patent document 7 are shown in the following Table 1-1 to Table 1-25.

TABLE 1-1

| Ex. No. | structure | data |
|---|---|---|
| Example 1 | 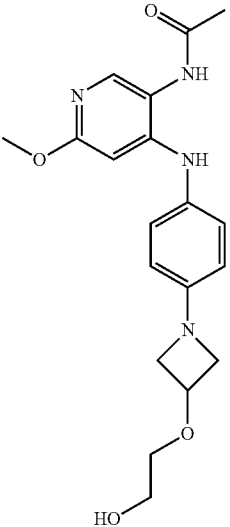 [SMILES: COc1cc(Nc2ccc(N3CC(OCCO)C3)cc2)c(NC(C)=O)cn1] | $^1$H-NMR (CDCl$_3$, 400 MHz) δ : 1.96 (1H, s), 2.24 (2H, s), 3.52-3.62 (2H, m), 3.70-3.90 (7H, m), 4.09-4.18 (2H, m), 4.42-4.53 (1H, m), 6.09-6.14 (1H, m), 6.40-6,54 (3H, m), 6.97-7.10 (3H, m), 7.78-7.79 (1H, s).<br>MS (ESI) m/z : 373 (M + H)$^+$. |
| Example 2 | 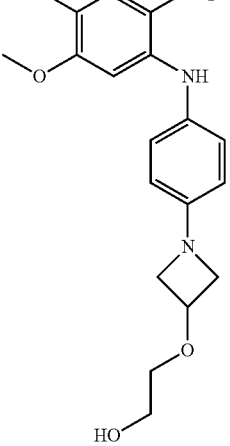 | $^1$H-NMR (CDCl$_3$, 400 MHz) δ : 1.85-2.00 (1H, br), 3.55-3,64 (2H, m), 3,73 (3H, s), 3.77-3.88 (4H, m), 4.14-4.28 (2H, m), 4.47-4.58 (1H, m), 6.35 (1H, d, J 6,50-6.52 (2H, m), 7.10-7.12 (2H, m), 7.92 (1H, d, J 9.60-9.70 (1H, br).<br>MS (ESI) m/z: 373(M + H)$^+$. |

TABLE 1-1-continued
| Ex. No. | structure | data |
| --- | --- | --- |
| Example 3 | 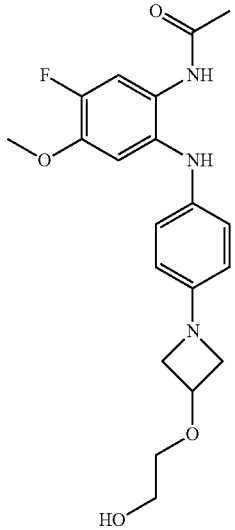 [SMILES: COc1cc(Nc2ccc(N3CC(OCCO)C3)cc2)c(NC(C)=O)cc1F] | $^1$H-NMR (CD$_3$CN, 400 MHz) δ : 2.07 (3H, m), 2.75-2.85 (2H, m), 3.49-3.55 (2H, m), 3.60-3.68 (4H, m), 3.72 (3H, s), 4.35-4,55 (1H, m), 7.30-7.63 (5H, m), 8,50-8.80 (1H, m). MS (ESI) m/z : 390 (M + H)$^+$. |
| Example 4 | 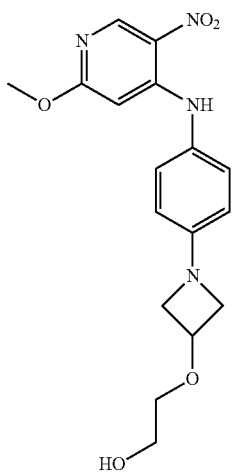 [SMILES: COc1cc(Nc2ccc(N3CC(OCCO)C3)cc2)c([N+](=O)[O-])cn1] | $^1$H-NMR (DMSO-d$_6$, 400 MHz) δ : 1.93 (1H, t, J = 6.1 Hz), 3.54-3.62 (2H, m), 3.72-3.84 (4H, m), 3.90 (3H, s), 4.12-4.20 (2H, m), 4.45-4.58 (1H, m), 6.02 (1H, s), 6.48-6.50 (2H, m), 7.07-7.09 (2H, m), 9.02 (1H, s), 9.26 (1H, br). MS (ESI) m/z : 361 (M + H)$^+$. |

TABLE 1-2
| Ex. No. | structure | data |
| --- | --- | --- |
| Example 5 | 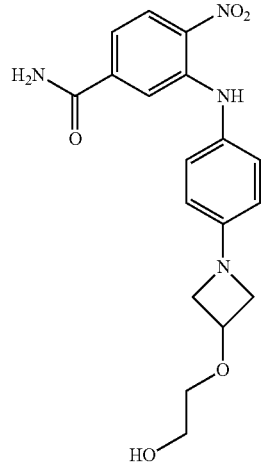 [SMILES: NC(=O)c1ccc([N+](=O)[O-])c(Nc2ccc(N3CC(OCCO)C3)cc2)c1] | $^1$H-NMR (DMSO-d$_6$, 400 MHz) δ : 3.42-3.45 (2H, m), 3.48-3.53 (2H, m), 3.60-3.66 (2H, m), 4.07-4.12 (2H, m), 4.42-4.46 (1H, m), 4.68 (1H, t, J = 5.3 Hz), 6.50-6.53 (2H, m), 7.11-7.15 (3H, m), 7.40 (1H, d, J 7.52-7.57 (1H, br), 8.03-8.10 (1H, br), 8.12 (1H, d, J = 8.8 Hz), 9.36<br>MS (ESI) m/z : 373 (M + H)$^+$. |
| Example 6 | 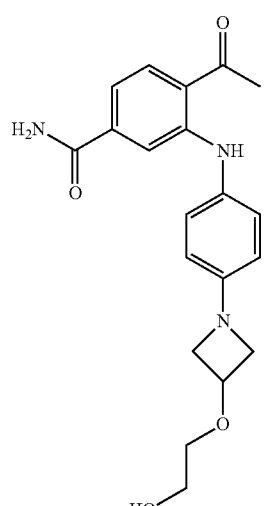 | $^1$H-NMR (CDCl$_3$, 400 MHz) δ : 1.96-2.07 (1H, br), 2.65 (3H, s), 3.57 (2H, t, J = 4.4 Hz), 3.72-3.82 (4H, m), 4.11-4.17 (2H, m), 4.45-4.52 (1H, m), 5.45-5.75 (1H, br), 5.75-6.10 (1H, br), 6.45-6.51 (2H, m), 6.97 (1H, dd, J = 8.3, 1.4 Hz), 7.05-7.12 (2H, m), 7.30 (1H, d, J = 1.4 Hz), 7.82 (1H, d, J = 8.3 Hz), 10.33 (1H, s).<br>Ms (ESI) m/z : 370 (M + H)$^+$. |
| Example 7 | 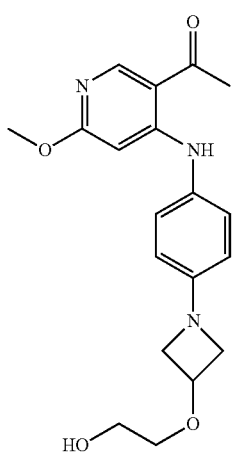 [SMILES: COc1cc(Nc2ccc(N3CC(OCCO)C3)cc2)c(C(C)=O)cn1] | $^1$H-NMR (CDCl$_3$, 400 MHz) δ : 1.90-2.00 (1H, m), 2.60 (3H, s), 3.54-3.60 (2H, m), 3.72-3.82 (4H, m), 3.88 (3H, s), 4.10-4.19 (2H, m), 4.45-4.54 (1H, m), 6.02 (1H, s), 6.44-6.50 (2H, m), 7.02-7.08 (2H, m), 8.62 (1H, s), 10.25-10.35 (1H, br).<br>MS (ESI) m/z : 358 (M + H)$^+$. |

TABLE 1-2-continued
| Ex. No. | structure | data |
|---|---|---|
| Example 8 | 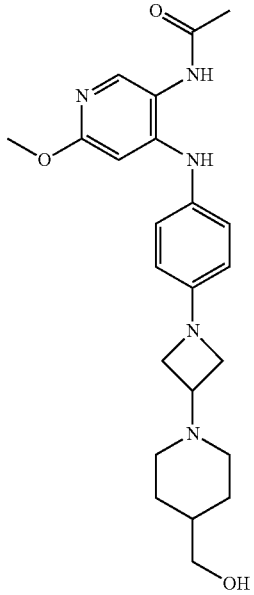 [SMILES: COc1cc(Nc2ccc(N3CC(N4CCC(CO)CC4)C3)cc2)c(NC(C)=O)cn1] | ¹H-NMR (CDCl₃, 400 MHz) δ : 1.24-1.37 (2H, m), 1.50-1.70 (2H, m), 1.75-1.84 (2H, m), 1.86-1.96 (2H, m), 1.96 (1H, s), 2.24 (2H, s), 2.87-2.66 (2H, m), 3.26-3.35 (1H, m), 3.51 (2H, d, J = 6.3 Hz), 3.64-3.74 (2H, m), 3.82 (2H, s), 3.84 (1H, s), 3.94-4.03 (2H, m), 6.07 (0.35H, s), 6.08 (0.35H, s), 6,12 (0.65H, s), 6.26 (0.65H, s), 6.40-6.47 (2H, m), 6.50 (0.35H, s), 6.96 (0.65H, s), 6.98-7.04 (2H, m), 7.77 (0.65H, s), 7.79 (0.35H, s).<br>MS (ESI) m/z : 426 (M + H)⁺. |
TABLE 1-3
| Ex. No. | structure | data |
|---|---|---|
| Example 9 | 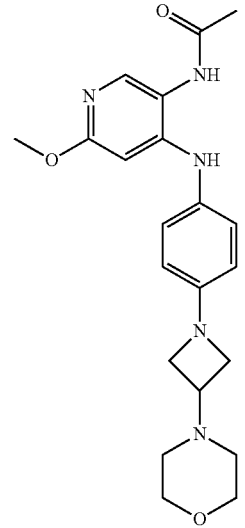 [SMILES: COc1cc(Nc2ccc(N3CC(N4CCOCC4)C3)cc2)c(NC(C)=O)cn1] | ¹H-NMR (CDCl₃, 400 MHz) δ : 1.96 (1H, s), 2,24 (21-1, s), 2.40-2.51 (4H, m), 3.29-3.39 (1H, m), 3.67-3.78 (6H, m), 3.82 (1.8H, s), 3.85 (1.2H, s), 3.94-4,03 (2H, m), 6.07 (0.4H, s), 6,12 (0.6H, s), 6.29-6,35 (0.6H, m), 6.40-6.50 (2.4H, m), 6.96-7.06 (3H, m), 7.78 (0.6H, 0, 7.79 (0.4H, s).<br>MS (ESI) m/z: 398 (M + H)⁺. |

TABLE 1-3-continued

| Ex. No. | structure | data |
| --- | --- | --- |
| Example 10 | 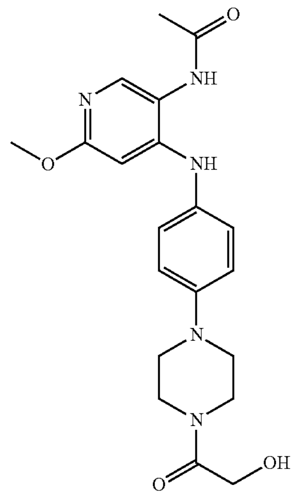 [SMILES: COc1cc(Nc2ccc(N3CCN(C(=O)CO)CC3)cc2)c(NC(C)=O)cn1] | $^1$H-NMR (DMSO-d$_6$, 400 MHz) δ : 2.04 (3H, s), 3.05-3,15 (4H, m), 3.42-3.55 (2H, m), 3.56-3.65 (2H, m), 3.71 (3H, s), 6.02 (1H, s), 6.97-6 .99 (2H, m), 7.05-7.08 (2H, m), 7.71 (1H, s), 9.10-9.30 (1H, s).<br>MS (ESI) m/z : 400 (M + H)$^+$. |
| Example 11 | 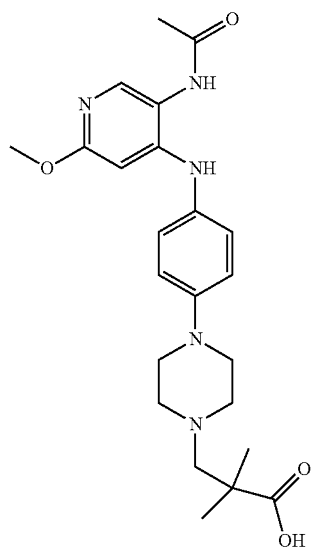 [SMILES: COc1cc(Nc2ccc(N3CCN(CC(C)(C)C(=O)O)CC3)cc2)c(NC(C)=O)cn1] | $^1$H-NMR (DMSO-d$_6$, 400 MHz) δ : 1.11 (6H, s), 2.03 (3H, s), 2.53-2.58 (2H, br), 2.63-2.74 (4H, m), 3,05-3.15 (41-1, m), 3.70 (3H, s), 5.99 (1H, s), 6.92-6.95 (2H, m), 7.02-7.04 (2H, m), 9.14 (1H, s).<br>MS (ESI) m/z : 442(M + H)$^+$. |
| Example 12 | 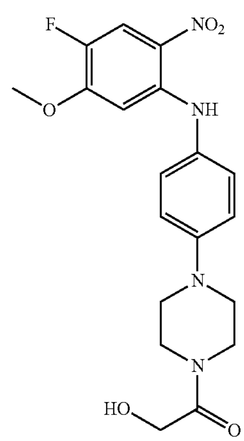 [SMILES: COc1cc(Nc2ccc(N3CCN(C(=O)CO)CC3)cc2)c([N+](=O)[O-])cc1F] | $^1$H-NMR (DMSO-d$_6$, 400 MHz) δ : 3.12-3.24 (4H, m), 3.46-3.54 (2H, m), 3.59-3.66 (2H, m), 3.74 (3H, s), 4.10-4.14 (2H, m), 4.58-4.68 (1H, br), 6.55 (1H, d, J = 7.6 Hz), 7.02-7.04 (2H, m), 7.26-7.28 (2H, m), 7.95 (1H, d, J = 12.0 Hz), 9.66 (1H, s).<br>MS (ESI) m/z : 405 (M + H)$^+$. |

TABLE 1-4
| Ex. No. | structure | data |
| --- | --- | --- |
| Example 13 | 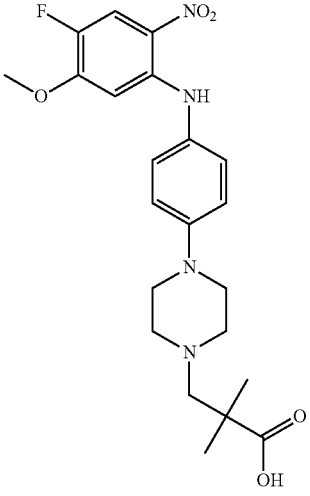 [SMILES: COc1cc(Nc2ccc(N3CCN(CC(C)(C)C(=O)O)CC3)cc2)c([N+](=O)[O-])cc1F] | ¹H-NMR (DMSO-d₆, 400 MHz) δ : 1.10 (6H, s), 2.45-2.55 (2H, m), 2.59-2,64 (4H, m), 3.07-3.18 (4H, m), 3.73 (3H, s), 6.52 (1H, d, J = 7.6 Hz), 6.97-6,99 (2H, m), 7.22-7.25 (2H, m), 7.94 (1H, d, J = 12.0 Hz), 9.66 (1H, s). MS (ESI) m/z : 447 (M + H)⁺. |
| Example 14 | 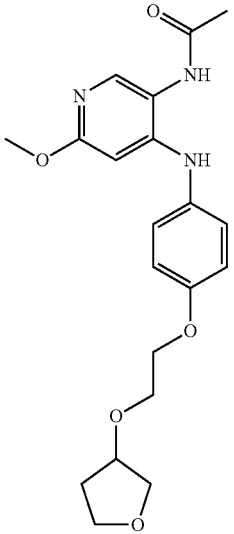 [SMILES: COc1cc(Nc2ccc(OCCOC3CCOC3)cc2)c(NC(C)=O)cn1] | ¹H-NMR (CDCl₃, 400 MHz) δ : 1.96 (1H, s), 1.97-2.09 (2H, m), 2.25 (2H, s), 3.74-3.96 (6H, M), 3.82 (3H, s), 4.08-4.14 (2H, m), 4.20-4.27 (1H, m), 6.15 (0.3H, s), 6.20 (1H, s), 6.56 (0.3H, s), 6.67 (0.7H, s), 6.85-6.96 (2H, m), 7.05-7,14 (2H, m), 7.35 (0.7H, s), 7.82 (1H, s). MS (ESI) m/z: 388 (M + H)⁺. |
| Example | 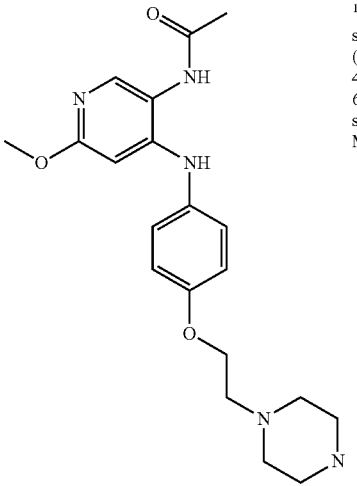 | ¹H-NMR (DMSO-d₆, 400 MHz) δ : 2.04 (3H, s), 2.14 (3H, s), 2.26-2.39 (4H, m), 2.47-2.54 (4H, m), 2.66-2.69 (2H, m), 3.71 (3H, s), 4.04-4,07 (2H, m), 6.00 (1H, s), 6.94-6,97 (2H, m), 6.94-6,97 (2H, m), 7.08-7.10 (1H, s), 7.71 (1H, s), 9.10 (1H, s). MS (ESI) m/z : 400 (M + H)⁺. |

TABLE 1-4-continued
| Ex. No. | structure | data |
| --- | --- | --- |
| Example 16 | 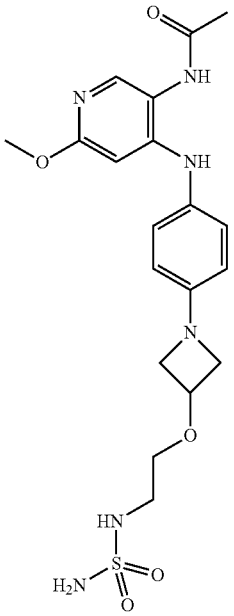 [SMILES: COc1cc(Nc2ccc(N3CC(OCCNS(N)(=O)=O)C3)cc2)c(NC(C)=O)cn1] | $^1$H-NMR (DMSO-d$_6$, 400 MHz) δ : 2.03 (3H, s), 3.04 (2H, q, j t, J = 6.1 Hz), 3.49 (2H, t, J = 6.1 Hz), 3,57-3.64 (2H, m), 3.69 (3H, s), 4.01-4.10 (2H, m), 4.38-4.46 (1H, m), 5.89 (1H, s), 6.43-6.50 (2H, m), 6.51-6.60 (3H, m), 6.95-7.05 (2H, m), 7.54 (1H, s), 7.67 (1H, s), 9.05 (1H, s).<br>MS (ESI) m/z : 451 (M + H)$^+$. |
TABLE 1-5
| Ex. No. | structure | data |
| --- | --- | --- |
| Example 17 | 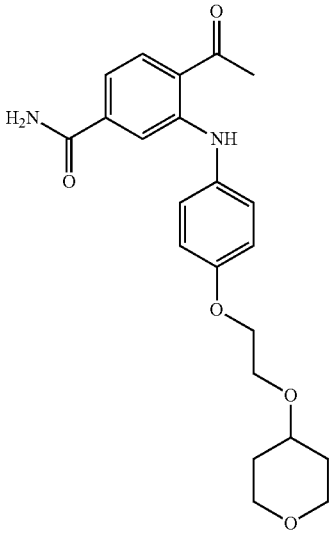 [SMILES: CC(=O)c1ccc(C(N)=O)cc1Nc1ccc(OCCOC2CCOCC2)cc1] | $^1$H-NMR (DMSO-d$_6$, 400 MHz) δ : 1.60-1.70 (2H, m), 1.90-1.98 (2H, m), 2.66 (3H, s), 3.42-3.52 (2H, m), 3,57-3.66 (1H, m), 3.82-3,88 (2H, m), 3.92-4.02 (2H, m), 4.10-4.16 (2H, m), 5.40-5.60 (1H, br), 5.80-6.00 (1H, br), 6.93-6.95 (2H, m), 7.00 (1H? dd, J = 8.3, 1.7 Hz), 7.15-7.17 (2H, m), 7.36 (1H, d, J = 1.7 Hz), 7.84 (1H, d, J = 8.3 Hz), 10.39 (1H, s).<br>MS (ESI) m/z: 399 (M + H)$^+$. |

TABLE 1-5-continued
| Ex. No. | structure | data |
|---|---|---|
| Example 18 | 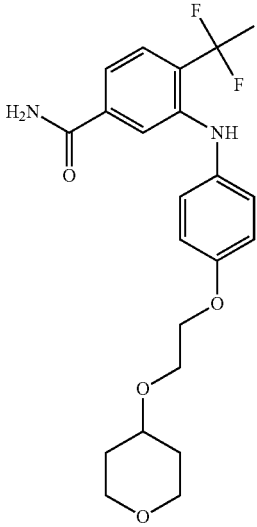 [SMILES: CC(F)(F)c1ccc(C(N)=O)cc1Nc1ccc(OCCOC2CCOCC2)cc1] | ¹H-NMR (CDCl₃, 400 MHz) δ : 1.59-1.70 (2H, m), 1.90-2.00 (2H, m), 2.04 (3H, t, J = 18.6 Hz), 3.41-3.52 (2H, m), 3.57-3.66 (1H, m), 3.80-3.88 (2H, m), 3.94-4.01 (2H, m), 4.10-4.16 (2H, m), 5.40-6.05 (1H, m), 6.14-6.22 (1H, m), 6.89-6.96 (2H, m), 7.03-7.10 (2H, m), 7.17-7.22 (1H, m), 7.43-7.48 (2H, m). MS (ESI) m/z : 421 (M + H)⁺. |
| Example 19 | 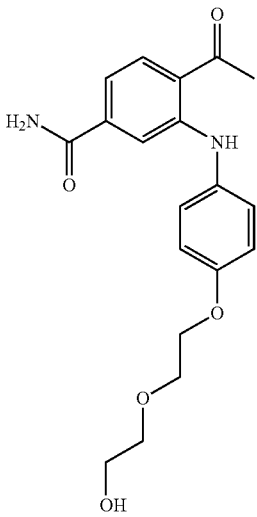 [SMILES: CC(=O)c1ccc(C(N)=O)cc1Nc1ccc(OCCOCCO)cc1] | ¹H-NMR (CDCl₃, 400 MHz) δ : 2.06-2.30 (1H, br), 2.66 (3H, s), 3.64-3.71 (2H, m), 3.72-3.78 (2H, m), 3.85-3.94 (2H, m), 4.16-4.24 (2H, m), 5.60-5.80 (1H, br), 6.04-6.28 (1H, br), 6.92-7.00 (2H, m), 7.03 (1H, dd, J+328.3, 1.4 Hz), 7.12-7.21 (2H, m), 7.33 (1H, d, J = 1.4 Hz), 7.84 (1H, d, J = 8.3 Hz), 10.37 (1H, s). MS (ESI) m/z : 357 (M + H)⁺. |
| Example 20 | 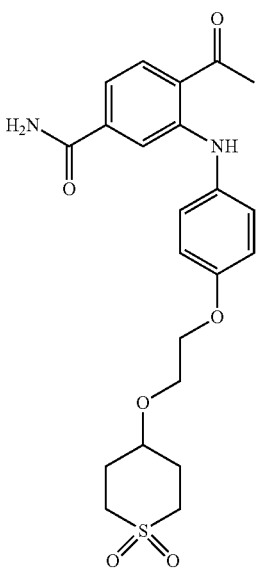 [SMILES: CC(=O)c1ccc(C(N)=O)cc1Nc1ccc(OCCOC2CCS(=O)(=O)CC2)cc1] | ¹H-NMR (CDCl₃, 400 MHz) δ : 2.15-2.27 (2H, m), 2.31-2.41 (2H, m), 2.66 (3H, s), 2.80-2.90 (2H, m), 3.24-3.37 (2H, m), 3.72-3.79 (1H, m), 3.80-3.86 (2H, m), 4.14-4.20 (2H, m), 5.55-5.75 (1H, br), 6.05-6.20 (1H, br), 6.89-6.95 (2H, m), 7.02 (1H, dd, J = 8.3, 1.7 Hz), 7.14-7.20 (2H, m), 7.40 (1H, d, J = 1.7 Hz), 7.84 (1H, d, J = 8.3 Hz), 10.40 (1H, s). MS (ESI) m/z ; 447 (M + H)⁺. |

TABLE 1-6

| Ex. No. | structure | data |
| --- | --- | --- |
| Example 21 | 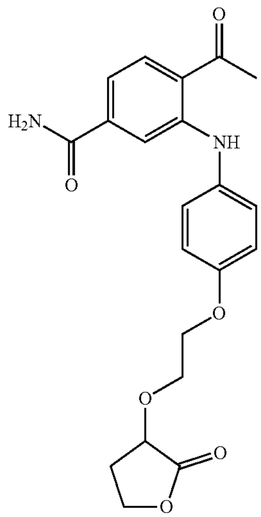 [SMILES: CC(=O)c1ccc(C(N)=O)cc1Nc1ccc(OCCOC2CCOC2=O)cc1] | ¹H-NMR (CDCl₃, 400 MHz) δ : 2,30-2.40 (1H, m), 2.53-2.62 (1H, m), 2.66 (3H, s), 3.98-4.06 (1H, m), 4.10-4.33 (5H, m), 4.40-4,46 (1H, m), 5.45-5.70 (1H, br), 5.80-6.10 (1H, br), 6.91-6,97 (2H, m), 7.01 (1H, dd, J = 8.0, 1.7 Hz), 7.13-7.19 (2H, m), 7.36 (1H, d, J = 1.7 Hz), 7.84 (1H, d, J = 8.0 Hz), 10.38 (1H, s). MS (ESI) m/z : 397 (M + H)⁺. |
| Example 22 | 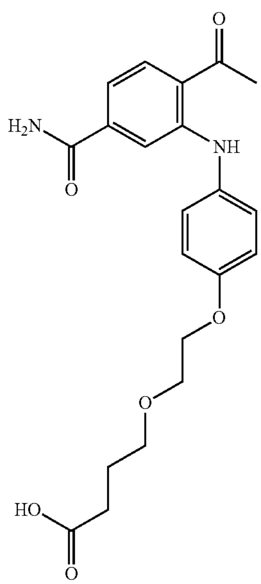 [SMILES: CC(=O)c1ccc(C(N)=O)cc1Nc1ccc(OCCOCCCC(=O)O)cc1] | ¹H-NMR (CDCl₃, 400 MHz) δ : 1.87-2.00 (2H, m), 2.46 (2H, t, J = 7.1 Hz), 2.65 (3H, s) , 3.60 (2H, t, J = 6.1 Hz), 3.76-3.87 (2H, m), 4.10-4.20 (2H, m), 6.06-6.22 (1H, br), 6.40-6.56 (1H, br), 6.92-7.02 (3H, m), 7.10-7.18 (2H, m), 7.31-7.37 (1H, m), 7.82 (1H, d, J = 8.0 Hz), 10.35 (1H,s). MS (ESI) m/z : 399 (M + H)⁺. |
| Example 23 | 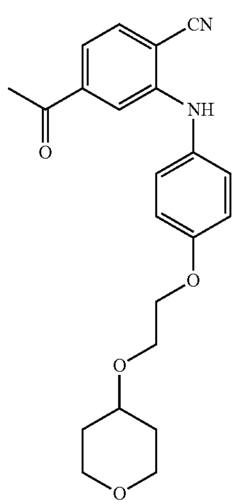 | ¹H-NMR (CDCl₃, 400 MHz) δ : 1.61-1.73 (2H, m), 1.91-2.02 (2H, m), 2.49 (3H, s), 3.41-3.53 (2H, m), 3.58-3.67 (1H, m), 3.83-3.91 (2H, m), 3.93-4.03 (2H, m), 4.11-4.22 (2H, m), 6.30 (1H, s), 6.92-7.02 (2H, m), 7.10-7.20 (2H, m), 7.24-7.29 (1H, m), 7.40-7.44 (1H, m), 7.55 (1H, d, J = 8.0 Hz). MS (ESI) m/z : 379 (M + H)⁺. |

TABLE 1-6-continued

| Ex. No. | structure | data |
| --- | --- | --- |
| Example 24 | (structure) | $^1$H-NMR (CDCl$_3$, 400 MHz) δ : 2.52-2.68 (9H, m), 2.78-2.88 (2H, m), 3.75-3.82 (4H, m), 5.70-6.20 (2H, br), 7.02 (1H, d, J = .7, 8.3 Hz), 7.16-7.24 (4H, m), 7.58 (1H, d, J = 1.7 Hz), 7.85 (1H, d, J = 8.3 Hz), 10.49 (1H, s).<br>MS (ESI) m/z: 368 (M + H)$^+$. |

TABLE 1-7

| Ex. No. | structure | data |
| --- | --- | --- |
| Example 25 | (structure) | $^1$H-NMR (DMSO-d$_6$, 400 MHz) δ : 2.34-2.43 (4H, m), 2.65 (3H, s), 3.08 (2H, d, J = 6.4 Hz), 3.54-3.62 (4H, m), 6.22 (1H, dt, J = 15.8, 6.4 Hz), 6.52 (1H, d, J = 15.8 Hz), 7.18-7.27 (3H, m), 7.42-7.53 (3H, m), 7.69 (1H, d, J = 1.2 Hz), 8.00 (11-1, d, J = 8.3 Hz), 8.02-8.09 (1H, br), 10.35 (1H, s).<br>MS (ESI) m/z: 378 (M + H)$^+$. |
| Example 26 | (structure) | $^1$H-NMR (CDC$_3$, 400 MHz) δ : 1.58-1.72 (2H, m), 1.90-1.98 (2H, m), 2.30-2.40 (1H, br), 3.41-3.50 (2H, m), 3.55-3,65 (1H, m), 3,80-3.86 (2H, m). 3.91-3.99 (2H, m), 4.05-4.12 (2H, m), 4.73 (2H, d, J = 2.9 Hz), 5.50-6.20 (2H, br), 6.77 (1H, g), 6.84-6.90 (2H, m), 7.00-7.06 (2H, m), 7.12 (1H, dd, J = 7.8, 1.4 Hz), 7.16 (1H, d, J = 7.8 Hz), 7.47 (1H, d, J = 1.4 Hz).<br>MS (ESI) m/z : 387 (M + H)$^+$. |

TABLE 1-7-continued
| Ex. No. | structure | data |
|---|---|---|
| Example 27 | 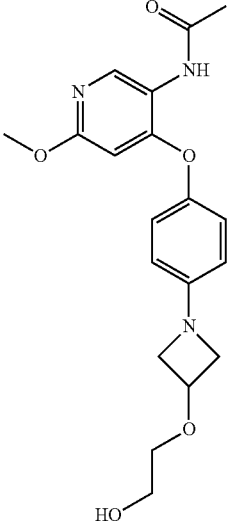 [SMILES: COc1cc(Oc2ccc(N3CC(OCCO)C3)cc2)c(NC(C)=O)cn1] | $^1$H-NMR (DMSO-d$_6$, 400 MHz) δ : 2.06 (3H, s), 3.38-3.43 (2H, m), 3.49-3.56 (2H, m), 3.59-3.66 (2H, m), 3.74 (3H, s), 4.03-4.13 (2H, m), 4.39-4.48 (1H, m), 5.78 (1H, s), 6.49-6.51 (2H, m), 6.97-6.99 (2H, m), 8.36 (1H, s), 9.44 (1H, br).<br>MS (ESI) m/z : 374 (M + H)$^+$). |
| Example 28 | 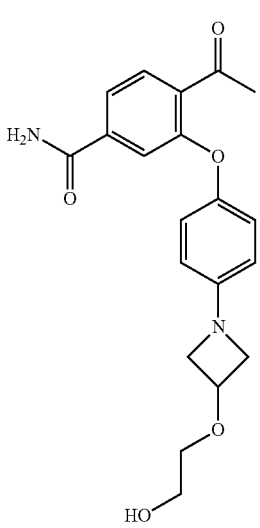 [SMILES: CC(=O)c1ccc(C(N)=O)cc1Oc1ccc(N2CC(OCCO)C2)cc1] | $^1$H-NMR (CDC$_3$, 400 MHz) δ : 2.06-2.17 (1H, br), 2.70 (3H, s), 3.54-3.61 (2H, m), 3.70-3,83 (4H, m), 4.13 (2H, t, J = 6.9 Hz), 4.44-4.52 (1H, m) , 5,60-6.30 (2H, br), 6.45-6.52 (2H, m), 6.90-6.97 (2H, m), 7.23-7.27 (1H, m), 7.37-7.43 (1H, m), 7.82 (1H, d, J = 8.1 Hz).<br>MS (ESI) m/z : 371 (M + H)$^+$). |

TABLE 1-8

| Ex. No. | structure | data |
|---|---|---|
| Example 29 | 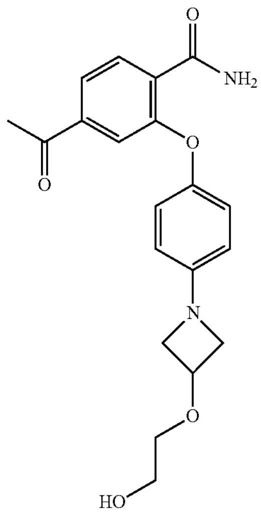 [SMILES: CC(=O)c1ccc(C(N)=O)c(Oc2ccc(N3CC(OCCO)C3)cc2)c1] | ¹H-NMR (CDCl₃, 400 MHz) δ : 1.93 (1H, t, J = 6.1 Hz), 2.52 (3H, s) , 3.56-3.61 (2H, m), 3.75-3.83 (4H, m), 4,15 (2H, t, J = 7.1 Hz), 4.44-4.55 (1H, m), 5,76-5.89 (1H, br), 6.46-6.53 (2H, m), 6.93-6.99 (2H, m), 7.31 (1H, J = 1.5 Hz), 7.64 (1H, J = 8.0, 1.5 Hz), 7.73-7.86 (1H, br), 8.34 (1H, d, J = 8.0 Hz).<br>MS (ESI) m/z : 371 (M + H)⁺. |
| Example 30 | 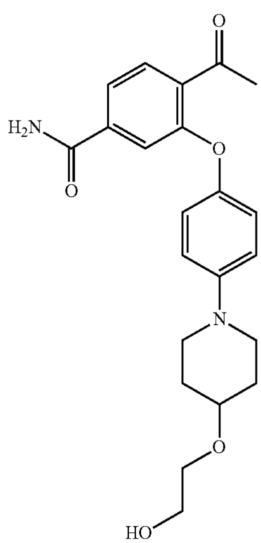 [SMILES: CC(=O)c1ccc(C(N)=O)cc1Oc1ccc(N2CCC(OCCO)CC2)cc1] | ¹H-NMR (CDCl₃, 400 MHz) δ: 1.70-1.84 (2H, m), 1.97-2.03 (2H, m), 2.88-3.02 (2H, m), 2.69 (3H, s), 2.88-3.00 (2H, m), 3.43-3.57 (3H, m), 3.62 (2H, t, J = 4.4 Hz), 3.73-3.79 (2H, m), 6.92-7.00 (4H, m), 7.30 (1H, d, J = 1.2 Hz), 7.42 (1H, dd, J = 8.0, 1.2 Hz), 7.83 (1H, d, J = 8.0 Hz).<br>MS (ESI) m/z : 399(M + H)⁺. |
| Example 31 | 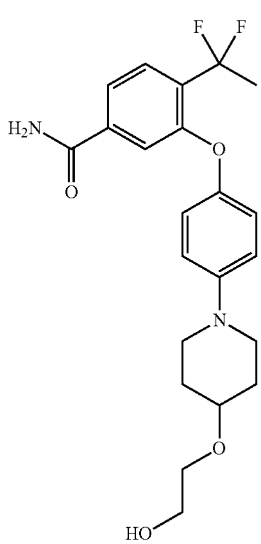 [SMILES: CC(F)(F)c1ccc(C(N)=O)cc1Oc1ccc(N2CCC(OCCO)CC2)cc1] | ¹H-NMR (CDCl₃, 400 MHz) δ : 1.70-1.82 (2H, m), 1.99-2.07 (3H, m), 2.69 (3H, t, J = 18.8 Hz), 2.88-2.98 (2H, m), 3.42-3.56 (3H, m), 3.62 (2H, t, J = 4.4 Hz), 3.73-3.79 (2H, m), 6.91-6.94 (4H, m), 7.24-7.28 (1H, m), 7.41-7.47 (1H, br), 7.41-7.47 (1H, m), 7.66 (1H, d, J = 8.0 Hz).<br>MS (ESI) m/z : 421 (M + H)⁺. |

TABLE 1-8-continued
| Ex. No. | structure | data |
|---|---|---|
| Example 32 | 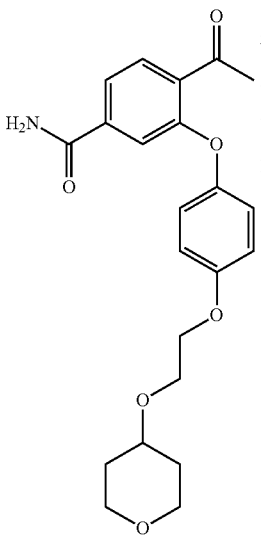 [SMILES: CC(=O)c1ccc(C(N)=O)cc1Oc1ccc(OCCOC2CCOCC2)cc1] | $^1$H-NMR (CDCl$_3$, 400 MHz) δ : 1.61-1.70 (2H, m), 1.90-2.00 (2H, m), 2.70 (3H, s), 3.42-3.51 (2H, m), 3.57-3.67 (1H, m), 3.82-3.88 (2H, m), 3.92-3.89 (2H, m), 4.11-4.18 (2H, m), 5.50-5.80 (1H, br), 5.90-6.13 (1H, br), 6.93-7.02 (4H, m), 7.27-7.30 (1H, m), 7.41-7.46 (1H, m), 7.82-7.86 (1H, m)<br>MS (ESI) m/z : 400 (M + H)$^+$. |
TABLE 1-9
| Ex. No. | structure | data |
|---|---|---|
| Example 33 | 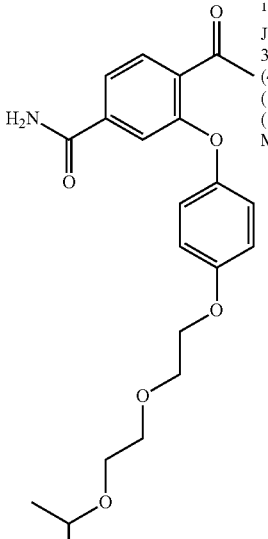 | $^1$H-NMR(DMSO-d$_6$, 400 MHz) δ : 1.06 (6H, d, J = 6.1 Hz), 2.58 (3H, s), 3.45-3.60 (5H, m), 3.70-3.78 (2H, m), 4.05-4.13 (2H, m), 6.96-7.10 (4H, m), 7.28 (1H, d, J = 1.5 Hz), 7.45-7.55 (1H, br), 7.62 (1H, dd, J = 8.0, 1.5 Hz), 7.71 (1H, d, J = 8.0 Hz), 8.00-8.10 (1H, br).<br>MS (ESI) m/z : 400 (M + H)$^+$. |

TABLE 1-9-continued

| Ex. No. | structure | data |
| --- | --- | --- |
| Example 34 | 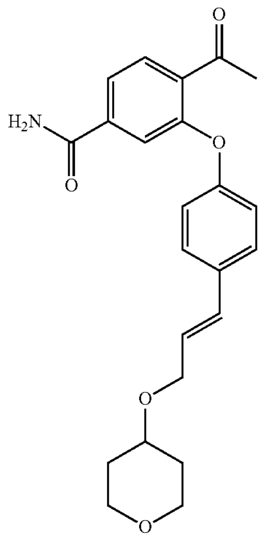 [SMILES: CC(=O)c1ccc(C(N)=O)cc1Oc1ccc(/C=C/COC2CCOCC2)cc1] | ¹H-NMR (CDCl₃, 400 MHz) δ : 1.62-1.71(2H, m), 1.90-1.99 (2H, m), 2,66 (3H, s), 3.42-3.51 (2H, m), 3.56-3.65 (1H, m), 3.94-4.02 (2H, m), 4.18-4.23 (2H, m), 5.60-6.20 (2H, br), 6.25 (1H, dt, J = 16.1, 5,8 Hz), 6.63 (1H, d, J = 16.1 Hz), 6.95-7.01 (2H, m), 7.38 (1H, d, J = 1.5 Hz), 7.38-7.43 (2H, m), 7.49 (1H, dd, J = 8,0, 1.5 Hz), 7.87 (1H, d, J = 8.0 Hz). MS (ESI) m/z : 394 (M + H)⁺. |
| Example 35 | 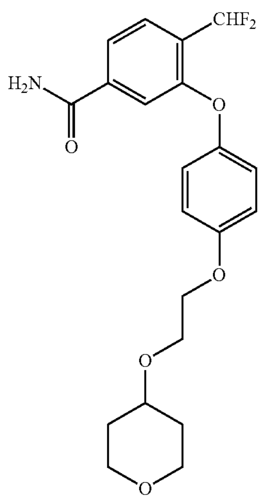 [SMILES: NC(=O)c1ccc(C(F)F)c(Oc2ccc(OCCOC3CCOCC3)cc2)c1] | ¹H-NMR(DMSO-d₆, 400 MHz) δ: 1.34-1.45 (2H, m), 1.81-1.90 (2H, m), 2.99-3.36 (2H, m), 3.52-3.60 (1H, m), 3.72-3.84 (4H, m), 4.07-4.13 (2H, m), 6.98-7.07 (4H, m), 7.11-7.41 (2H, m), 7,48-7.56 (1H, br), 7.64-7.72 (2H, m), 8.03-8.12 (1H, br). MS (ESI) m/z : 408 (M + H)⁺. |
| Example 36 | 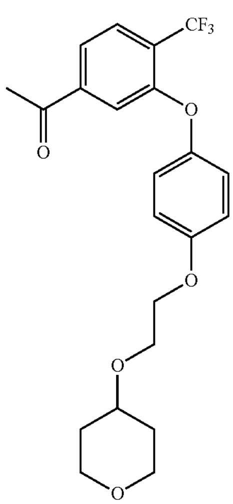 [SMILES: CC(=O)c1ccc(C(F)(F)F)c(Oc2ccc(OCCOC3CCOCC3)cc2)c1] | ¹H-NMR(DMSO-d₆, 400 MHz) δ : 1.36-1.47 (2H, m), 1.83-1,90 (2H, m), 2.55 (3H, s), 3.29-3 .37 (2H, m), 3.52-3.60 (1H, m), 3.75-3.84 (4H, m), 4.09-4.13 (2H, m), 7.01-7.09 (4H, m), 7.27 (1H, s), 7,83 (1H, d, J = 8.3 Hz), 7.93 (1H, d, J = 8.3 Hz). MS (ESI) m/z: 425 (M + H)⁺. |

TABLE 1-10
| Ex. No. | structure | data |
| --- | --- | --- |
| Example 37 | 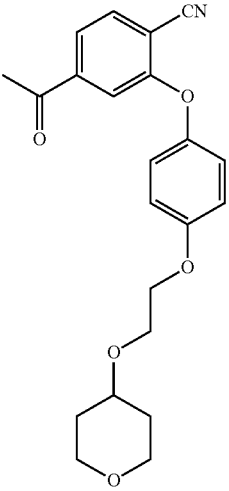 [SMILES: CC(=O)c1ccc(C#N)c(Oc2ccc(OCCOC3CCOCC3)cc2)c1] | $^1$H-NMR(DMSO-d$_6$, 400 MHz) δ: 1.36-1.47 (2H, m), 1.82-1.91 (2H, m), 2.54 (3H, s), 3.28-3.38 (2H, m), 3.52-3.61 (1H, m), 3.74-3.84 (4H, m), 4.09-4.16 (2H, m), 7.02-7.09 (2H, m), 7.12-7.20 (3H, m), 7.77-7.83 (1H, m), 8.06 (1H, d, J = 8.0 Hz).<br>MS (ESI) m/z : 382 (M + H)$^+$. |
| Example 38 | 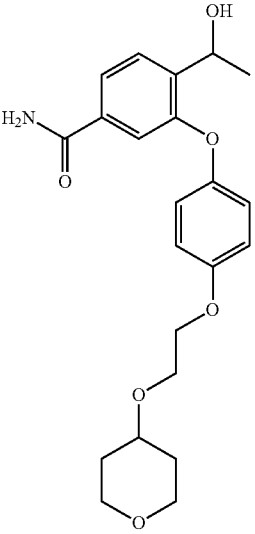 [SMILES: CC(O)c1ccc(C(N)=O)cc1Oc1ccc(OCCOC2CCOCC2)cc1] | $^1$H-NMR(DMSO-d$_6$, 400 MHz) δ : 1.32 (3H, d, J = 6.4 Hz), 1.35-1.46 (2H, m), 1.81-1.90 (2H, m), 3,31-3,37 (2H, m), 3.51-3.60 (1H, m), 3.72-3.85 (4H, m), 4.03-4.11 (2H, m), 5.01-5.10 (1H, m), 5.25 (1H, d, J = 4.4 Hz), 6.90-7.01 (4H, m), 7.16-7.21 (1H, m), 7.27-7.35 (1H, br), 7.57-7.64 (2H, m), 7.87-7.94 (1H, br).<br>MS (ESI) m/z : 402 (M + H)$^+$. |
| Example 39 | 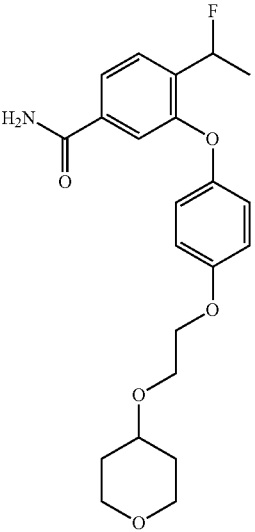 | $^1$H-NMR(DMSO-d$_6$, 400 MHz) δ : 1.34-1,46 (2H, m), 1.62 (3H, dd, J = 24, 6.3 Hz), 1.82-1.91 (2H, m), 8.30-3.37 (2H, m), 3.52-3.60 (1H, m), 3.75 (2H, t, J = 4.4 Hz), 3.77-3.84 (2H, m), 4.08 (2H, t, J = 4.4 Hz), 5.92-6.11 (1H, m), 6.98-7.02 (4H, m), 7,19-7,23 (1H, m), 7.36-7.45 (1H, br), 7,52-7.57 (1H, m), 7.62-7.68 (1H, m), 7.94-8.02 (1H, br).<br>MS (ESI) m/z : 404 (M + H)$^+$. |

TABLE 1-10-continued

| Ex. No. | structure | data |
| --- | --- | --- |
| Example 40 | 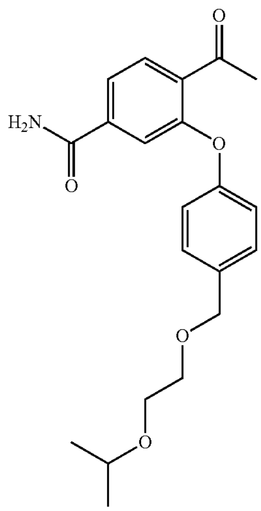 [SMILES: CC(=O)c1ccc(C(N)=O)cc1Oc1ccc(COCCOC(C)C)cc1] | ¹H-NMR (CDCl₃, 400 MHz) δ : 1,18 (6H, d, J = 6.1 Hz), 2.67 (3H, s), 3.60-3.72 (5H, m), 4,57 (2H, s), 5.45-6.25 (2H, br), 6.99-7.01 (2H, m), 7.37-7.39 (3H, m), 7.50 (1H, d, J = 8.0 Hz), 7.87 (1H, d, J = 8.0 Hz). MS (ESI) m/z : 370 (M + H)⁺. |

TABLE 1-11

| Ex. No. | structure | data |
| --- | --- | --- |
| Example 41 | 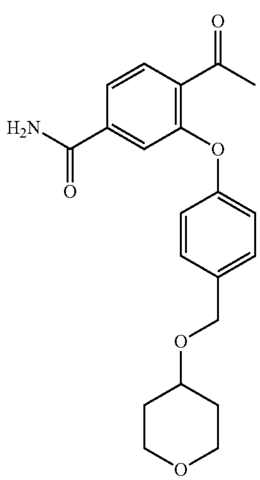 [SMILES: CC(=O)c1ccc(C(N)=O)cc1Oc1ccc(COC2CCOCC2)cc1] | ¹H-NMR (DMSO-d₆, 400 MHz) δ: 1.42-1.55 (2H, m), 1.85-1.95 (2H, m), 2.57 (3H, s), 3.30-3.38 (2H, m), 3.54-3.64 (1H, m), 3.77-3.87 (2H, m), 4.52 (2H, s), 7.03-7.09 (2H, m), 7.35-7.42 (3H, m), 7.55 (1H, s), 7.67-7.74 (1H, m), 7.77 (1H, d, J = 8.0 Hz), 8.10 (1H, s). MS (ESI) m/z: 392 (M + Na)⁺. |
| Example 42 | 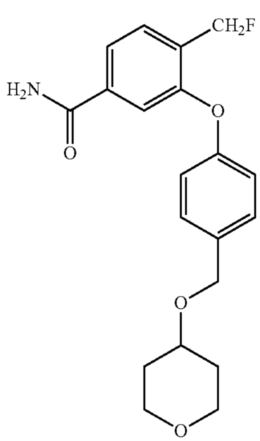 | ¹H-NMR (DMSO-d₆, 400 MHz) δ: 1.39-1.50 (2H, m), 1.82-1.93 (2H, m), 3.29-3.35 (2H, m), 3.52-3.62 (1H, m), 3.75-3.85 (2H, m), 4.50 (2H, s), 5,51 (21-1, d, J = 47 Hz), 6.98-7.00 (2H, m), 7.33-7.38 (3H, m), 7.40-7.46 (1H, br), 7.59 (1H, d, J = 8.0 Hz), 7.68 (1H, d, J = 8.0 Hz), 8.00-8.05 (1H, br). MS (ESI) m/z: 358 (M−H)⁻. |

TABLE 1-11-continued

| Ex. No. | structure | data |
| --- | --- | --- |
| Example 43 | 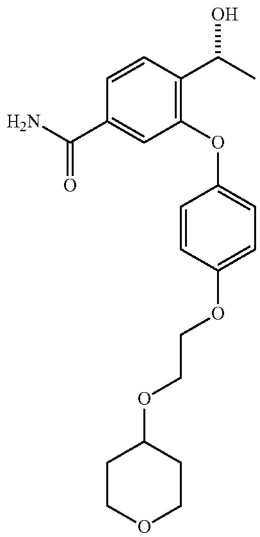 | $^1$H-NMR. (DMSO-$d_6$, 400 MHz) δ: 1.32 (3H, d, J = 6.4 Hz), 1.35-1.46 (2H, m), 1.81-1.90 (2H, m), 3.31-3.37 (2H, m), 3.51-3.60 (1H, m), 3.72-3.85 (4H, m), 4.03-4.11 (2H, m), 5.01-5.10 (1H, m), 5.25 (1H, d, J = 4.4 Hz), 6.90-7.01 (4H, m), 7.16-7.21 (1H, m), 7.27-7.35 (1H, br), 7.57-7.64 (2H, m), 7.87-7.94 (1H, br)<br>MS (ESI) m/z: 402 (M + H)$^+$. |
| Example 44 | 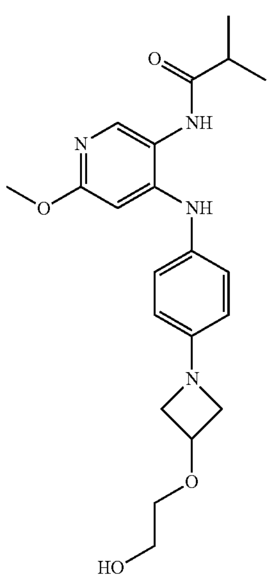 [SMILES: COc1cc(Nc2ccc(N3CC(OCCO)C3)cc2)c(NC(=O)C(C)C)cn1] | $^1$H-NMR (CDCl$_3$) δ: 1.30 (6H, d), 2.57-2.68 (1H, m), 3,55-3.60 (2H, m), 3.70-3.85 (7H, m), 4.08-4.18 (2H, m), 4.42-4.55 (1H, m), 6.05-6.18 (1H, m), 6.35-6.50 (3H, m), 6.97-7.10 (3H, m), 7.75-7.82 (1H, m).<br>MS (ESI) m/z: 401 (M + H)$^+$. |

TABLE 1-12
| Ex. No. | structure | data |
| --- | --- | --- |
| Example 45 | 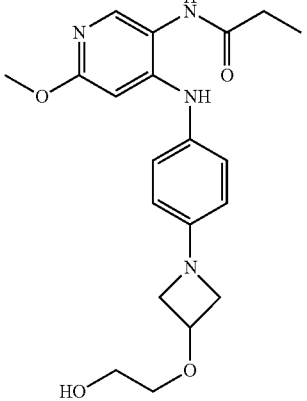 | ¹H-NMR (DMSO-d₆) δ: 1.08 (3H, t, J = 7.6 Hz), 2.36 (2H, q, J = 7.6 Hz), 3.41-3.44 (2H, m), 3.49-3.53 (2H, m), 3.57-3.60 (2H, m), 3.70 (3H, s), 4.04-4.07 (2H, m), 4.40-4.45 (1H, m), 4.65-4.68 (1H, m), 5.90 (1H, s), 6.47 (2H, d, J = 8.5 Hz), 7.00 (2H, d, J = 8.5), 7.51 (1H, s), 7.69 (1H, s), 8.97 (1H, s). MS (ESI) m/z: 387 (M + H)⁺. |
| Example 46 | 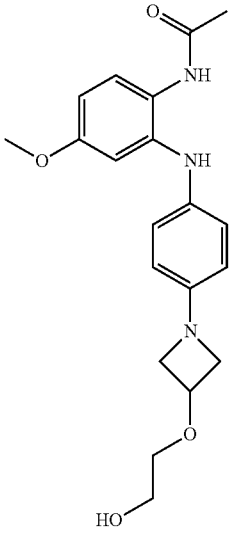 | ¹H-NMR (DMSO-d₆) δ: 2.01 (3H, s), 3.39-3.46 (2H, m), 3.47-3.58 (4H, m), 3.61 (3H, s), 3.95-4.06 (2H, m), 4.36-4.46 (1H, m), 4.62-4,70 (1H, br), 6.28 (1H, d), 6.36-6.48 (3H, m), 6.85-7.00 (3H, m), 7.10 (1H, d, J = 8.4 Hz), 9.11 (1H, s). MS (HSI) m/z: 372 (M + H)⁺. |
| Example 47 | 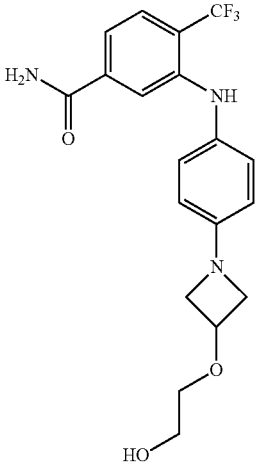 [SMILES: NC(=O)c1ccc(C(F)(F)F)c(Nc2ccc(N3CC(OCCO)C3)cc2)c1] | ¹H-NMR (CDCl₃) δ: 1.63-1.87 (1H, br), 3.55-3.62 (2H, m), 3.73-3.83 (4H, m), 4.11-4.20 (2H, m), 4.45-4.54 (1H, m), 5.53-5.70 (1H, br), 5.86-5.97 (1H, br), 6.01 (1H, s), 6.45-6.54 (2H, m), 7.03-7.14 (3H, m), 7.24-7.31 (1H, m), 7.53 (1H, d, J = 7.2 Hz). MS (ESI) m/z: 396 (M + H)⁺. |

TABLE 1-12-continued

| Ex. No. | structure | data |
|---|---|---|
| Example 48 | (structure) | $^1$H-NMR (DMSO-d$_6$) δ: 2.71 (3H, J = 4.6 Hz), 3.41-3,47 (2H, m), 3.48-3.56 (2H, m), 3.60-3.68 (2H, m), 4.06-4.15 (2H, m), 4.41-4.50 (1H, m), 4.63-4.70 (1H, m), 6.48-6.56 (2H, m), 7.07 (1H, dd, J = 8.8, 1.2 Hz), 7.10-7.18 (2H, m), 7.37 (1H, d, J = 1.2 Hz), 8.13 (1H, d, J = 8.8 Hz), 8.48-8.58 (1H, m), 9.37 (1H, s). MS (BSI) m/z: 387 (M + H)$^+$. |

TABLE 1-13

| Ex. No. | structure | data |
|---|---|---|
| Example 49 | (structure) | $^1$H-NMR (CDCl$_3$) δ: 1.21 (3H, t, J = 7.4 Hz), 1.60-1.70 (2H, m), 1.90-2.02 (2H, m), 2.65 (3H, s), 3.38-3.50 (4H, m), 3.56-3.68 (1H, m), 3.80-3.87 (2H, m), 3.94-3.99 (2H, m), 4.10-4.17 (2H, m), 5.90-6.00 (1H, br), 6.92-6.95 (3H, m), 7.15-7.17 (2H, m), 7.34 (1H, s), 7.82 (1H, d, J = 8.3 Hz), 10.40 (1H, s). MS (ESI) m/z δ: 427 (M + H)$^+$. |
| Example 50 | (structure) | $^1$H-NMR (CDCl$_3$) δ: 1.60-1.71 (2H, m), 1.90-2.00 (2H, m), 3.41-3.52 (2H, m), 3.57-3.67 (1H, m), 3.81-3.89 (2H, m), 3.92-4.00 (2H, m), 4.13-4.20 (2H, m), 5,55-5.78 (1H, br), 5.87-6.08 (1H, br), 6.95-7.03 (3H, m), 7.15-7.22 (2H, m), 7.45 (1H, d, J = 2.0 Hz), 8.25 (1H. d, J = 9.0 Hz), 9.41 (1H, s). MS (ESI) m/z: 402 (M + H)$^+$. |

TABLE 1-13-continued

| Ex. No. | structure | data |
|---|---|---|
| Example 51 | (structure) | ¹H-NMR (CDCl₃) δ: 2.00-2.10 (1H, br), 2.66 (3H, s), 3.94-4.04 (2H, m), 4.07-4.15 (2H, m), 5.44-5.66 (1H, br), 5.84-6.02 (1H, br), 6.91-6.98 (2H, m), 6.99 (1H, dd, J = 8.3, 1.2 Hz), 7.13-7.22 (2H, m), 7.38 (1H, d, J = 1.4 Hz), 7.85 (1H, d, J = 8.3 Hz), 10.39 (1H, s). MS (ESI) m/z: 315 (M + H)⁺. |
| Example 52 | (structure) | ¹H-NMR (CDCl₃) δ: 2.67 (3H, s), 3.65-4.05 (9H, m), 5.40-5.65 (1H, br), 5.80-6.05 (1H, br), 6.92-6.94 (2H, m), 7.00 (1H, dd, J = 8.5, 1.9 Hz), 7.15-7.17 (2H, m), 7.36 (1H, d, J = 1.9 Hz), 7.85 (1H, d, J = 8.5 Hz), 10.39 (1H, s). MS (ESI) m/z: 371 (M + H)⁺. |

TABLE 1-14

| Ex. No. | structure | data |
|---|---|---|
| Example 53 | (structure) | ¹H-NMR (CDCl₃) δ: 1.98-2.08 (2H, m), 2.66 (3H, s), 3.75-3.95 (6H, m), 4.13 (2H, t, J = 4.9 Hz), 4.21-4.27 (1H, m), 5.50-6.20 (2H, br), 6.89-6.96 (2H, m), 7.00 (1H, dd, J = 8.0, 1.7 Hz), 7.12-7.18 (2H, m), 7.36 (1H, d, J = 1.7 Hz), 7.84 (1H, d, J = 8.0 Hz), 10.38 (1H, s). MS (ESI) m/z: 383 (M − H)⁻. |

TABLE 1-14-continued

| Ex. No. | structure | data |
|---|---|---|
| Example 54 | 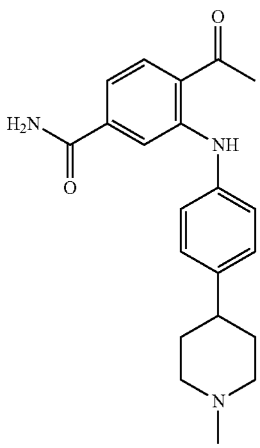 [SMILES: CC(=O)c1ccc(C(N)=O)cc1Nc1ccc(C2CCN(C)CC2)cc1] | $^1$H-NMR (DMSO-d$_6$) δ: 1.60-1.79 (4H, m), 1.92-2.01 (2H, m), 2.19 (3H, s), 2.40-2.49 (1H, m), 2.74-2.86 (2H, m), 2.64 (3H, s), 2.83-2.91 (2H, m), 7.17-7.22 (3H, m), 7.23-7.28 (2H, m), 7.45-7.52 (1H, br), 7.63 (1H, s), 7.97-8.06 (2H, m), 10.36 (1H, s).<br>MS (ESI) m/z: 352 (M + H)$^+$. |
| Example 55 | 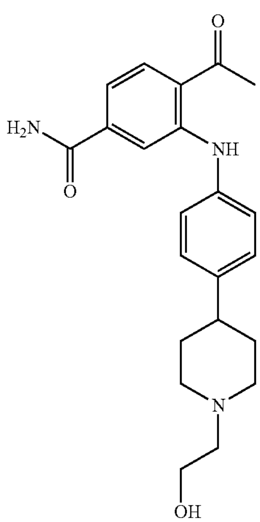 [SMILES: CC(=O)c1ccc(C(N)=O)cc1Nc1ccc(C2CCN(CCO)CC2)cc1] | $^1$H-NMR (DMSO-d$_6$) δ: 1.59-1.79 (4H, m), 2.03-2.13 (2H, m), 2.40-2.54 (3H, m), 2.64 (3H, s), 2.95-3.03 (2H, m), 3.49-3.55 (2H, m), 4.36-4.45 (1H, br), 7.17-7.22 (3H, m), 7.24-7.29 (2H, m), 7.46-7.52 (1H, br), 7.63 (1H, s), 7,97-8.07 (2H, m), 10.35 (1H, s).<br>MS (ESI) m/z: 382 (M + H)$^+$. |
| Example 56 | 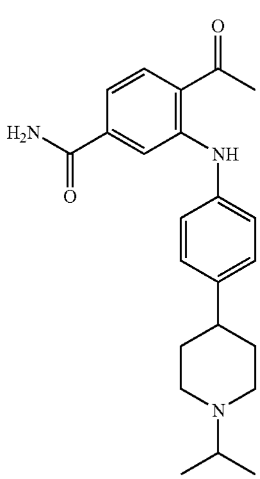 [SMILES: CC(=O)c1ccc(C(N)=O)cc1Nc1ccc(C2CCN(C(C)C)CC2)cc1] | $^1$H-NMR (DMSO-d$_6$) δ: 0.99 (6H, d, J = 6.6 Hz), 1.54-1.66 (4H, m), 1.73-1.82 (4H, m), 2.17-2.26 (2H, m), 2.41-2.50 (1H, m), 2.64 (3H, s), 2.71 (1H, septet, J = 6.6 Hz), 2.84-2.92 (2H, m) 7.16-7.21 (3H, m), 7.23-7,28 (2H, m), 7.44-7.51 (1H, br), 7.63 (1H, s), 7.96-8.07 (2H, m), 10.35 (1H, s).<br>MS (ESI) m/z: 380 (M + H)$^+$. |

TABLE 1-15
| Ex. No. | structure | data |
| --- | --- | --- |
| Example 57 | 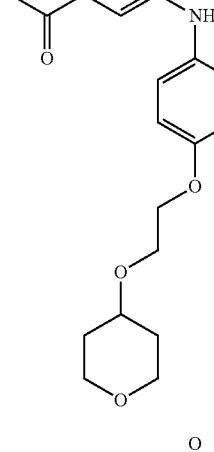 | ¹H-NMR (CDCl₃) δ: 1.61-1.72 (2H, m), 1.91-2.00 (2H, m), 2.48 (3H, s), 3.40-3.52 (2H, m), 3.57-3.67 (1H, m), 3.82-3.90 (2H, m), 3.93-4.02 (2H, m), 4.10-4.20 (2H, m), 5.40-6.30 (2H, br), 6.90-6.98 (2H, m), 7.12-7.17 (2H, m), 7.19 (1H, dd, J = 8.0, 1.4 Hz), 7.50 (1H, d, J = 8.0 Hz), 7.57 (1H, d, J = 1.4 Hz), 9.39 (1H, s).<br>MS (ESI) m/z: 399 (M + H)⁺. |
| Example 58 | 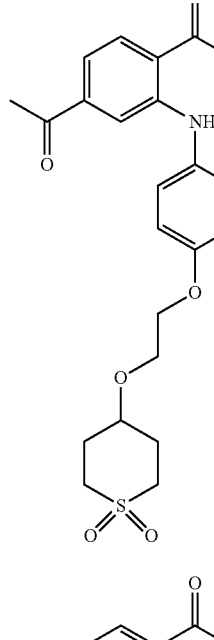 | ¹H-NMR (CDCl₃) δ: 2.17-2.29 (2H, m), 2.32-2.42 (2H, m), 2.49 (3H, s), 2.82-2.93 (2H, m), 3.30-3.43 (2H, m), 3.76-3.81 (1H, m), 3.81-3.87 (2H, m), 4.10-4.18 (2H, m), 5.50-6.10 (2H, br), 6.88-6.94 (2H, m), 7.12-7.18 (2H, m), 7.19 (1H, dd, J = 8.0, 1.4 Hz), 7.50 (1H, d, J = 8.0 Hz), 7.59 (1H, d, J = 1.4 Hz), 9.40 (1H, s).<br>MS (ESI) m/z: 447 (M + H)⁺. |
| Example 59 | 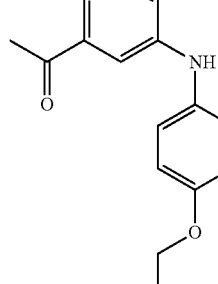 | ¹H-NMR (CDCl₃) δ: 2.16-2.30 (1H, br), 2.48 (3H, s), 3.66-3.73 (2H, m), 3.75-3.82 (2H, m), 3.86-3.93 (2H, m), 4.12-4.20 (2H, m), 5.50-6.20 (2H, br), 6.90-6.97 (2H, m), 7.12-7.18 (2H, m), 7.19 (1H, dd, J = 8.3, 1.4 Hz), 7.49 (1H, d, J = 8.3 Hz), 7.57 (1H, d, J = 1.4 Hz), 9.39 (1H, s).<br>MS (ESI) m/z: 359 (M + H)⁺. |

TABLE 1-15-continued

| Ex. No. | structure | data |
| --- | --- | --- |
| Example 60 | 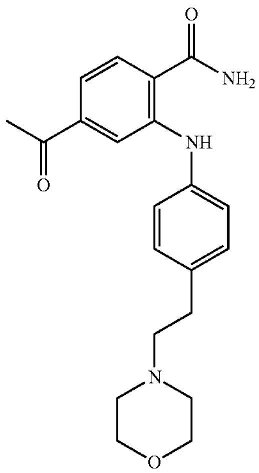 [SMILES: CC(=O)c1ccc(C(N)=O)c(Nc2ccc(CCN3CCOCC3)cc2)c1] | $^1$H-NMR (CDCl$_3$) δ: 2.51 (3H, s), 2.52-2.74 (6H, m), 2.78-2.91 (2H, m), 3.76-3.86 (4H, m), 5.40-6.30 (2H, br), 7.12-7.22 (4H, m), 7.24 (1H, dd, J = 8.3, 1.4 Hz), 7.52 (1H, d, J = 8.3 Hz), 7.80 (1H, d, J = 1.4 Hz), 9.48 (1H, s).<br>MS (ESI) m/z: 368 (M + H)$^+$. |

TABLE 1-16

| Ex. No. | structure | data |
| --- | --- | --- |
| Example 61 | 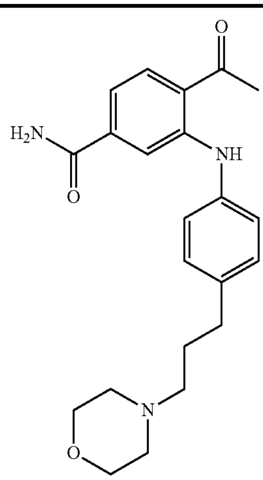 | $^1$H-NMR (CDCl$_3$) δ: 1.77-1.88 (2H, m), 2.33-2.42 (2H, m), 2.42-2.50 (4H, m), 2.62-2.68 (2H, m), 2.67 (3H, s), 3.72 (4H, t, J = 4.6 Hz), 5.40-5.70 (1H, br), 5.80-6.10 (1H, br), 7.02 (1H, dd, J = 8.3, 1.7 Hz), 7.12-7.21 (4H, m), 7.57 (1H, d, J = 1.7 Hz), 7.86 (1H, d, J = 8.3 Hz), 10.50 (1H, s).<br>MS (ESI) m/z: 382 (M + H)$^+$. |
| Example 62 | 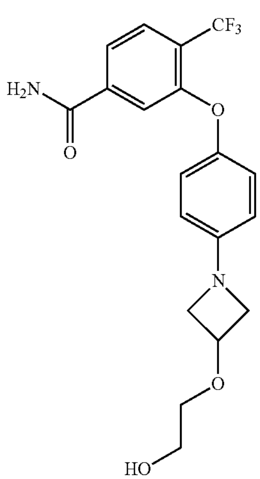 [SMILES: NC(=O)c1ccc(C(F)(F)F)c(Oc2ccc(N3CC(OCCO)C3)cc2)c1] | $^1$H-NMR (DMSO-d$_6$) δ: 3.41-3.45 (2H, m), 3.49-3.54 (2H, m), 3.62 (2H, dd, J = 8.1, 4.4 Hz), 4.07 (2H, dd, J = 8.1, 6.6 Hz), 4.40-4.46 (1H, m), 4.67 (1H, t, J = 5.6 Hz), 6.48-6.53 (2H, m), 6.94-6.99 (2H, m), 7.29 (1H, s), 7.57-7.62 (1H, br), 7.66 (1H, d, J = 8.0 Hz), 7.81 (1H, d, J = 8.0 Hz), 8.12-8.17 (1H, br).<br>MS (ESI) m/z: 397 (M + H)$^+$. |

TABLE 1-16-continued
| Ex. No. | structure | data |
| --- | --- | --- |
| Example 63 | 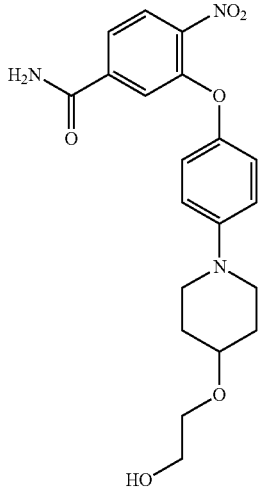 [SMILES: NC(=O)c1ccc([N+](=O)[O-])c(Oc2ccc(N3CCC(OCCO)CC3)cc2)c1] | ¹H-NMR (DMSO-d₆) δ: 1.49-1.60 (2H, m), 1.90-1.98 (2H, m), 3.31-3.38 (2H, m), 3.55-3.63 (1H, m), 2.84-2.92 (2H, m), 3.43-3.53 (7H, m), 4.56 (1H, t, J = 5.1 Hz), 7.01 (4H, s), 7.41 (1H, d, J = 1.7 Hz), 7.65-7.71 (1H, br), 7.70 (1H, dd, J = 8.3, 1.7 Hz), 8.08 (1H, d, J = 8.3 Hz), 8.18-8.23 (1H, br).<br>MS (ESI) m/z: 402 (M + H)⁺. |
| Example 64 | 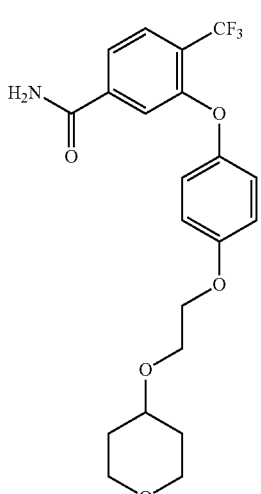 | ¹H-NMR (DMSO-d₆) δ: 1.35-1.46 (2H, m), 1.82-1.90 (2H, m), 3.29-3.37 (2H, m), 3.52-3.60 (1H, m), 3.74-3.84 (4H, m), 4.08-4.12 (2H, m), 7.00-7.07 (4H, m), 7.33 (1H, s), 7.58-7.64 (1H, br), 7.70 (1H, d, J = 8.0 Hz), 7.84 (1H, d, J = 8.0 Hz), 8.13-8.19 (1H, br).<br>MS (ESI) m/z: 426 (M+H)⁺. |

TABLE 1-17

| Ex. No. | structure | data |
| --- | --- | --- |
| Example 65 | 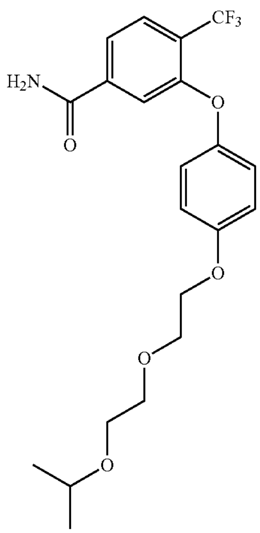 [SMILES: CC(C)OCCOCCOc1ccc(Oc2cc(C(N)=O)ccc2C(F)(F)F)cc1] | $^1$H-NMR (DMSO-d$_6$) δ: 1.06 (6H, d, J = 6.1 Hz), 3.47-3.57 (5H, m), 3.72-3.75 (2H, m), 4.08-4.10 (2H, m), 6.99-7.05 (4H, m), 7.33 (1H, s), 7.55-7.64 (1H, br), 7.69 (1H, d, J = 8.0 Hz), 7.83 (1H, d, J = 8.0 Hz), 8.13-8.20 (1H, br).<br>MS (ESI) m/z: 426 (M − H)$^-$. |
| Example 66 | 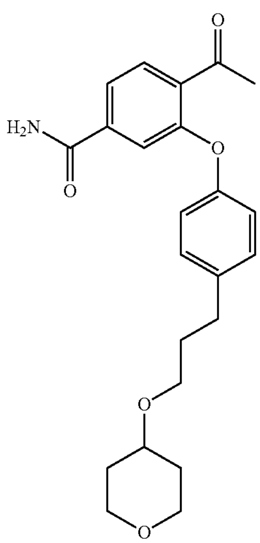 [SMILES: CC(=O)c1ccc(C(N)=O)cc1Oc1ccc(CCCOC2CCOCC2)cc1] | $^1$H-NMR (CDCl$_3$) δ: 1.52-1.69 (2H, m), 1.85-1.95 (4H, m), 2.67 (3H, s), 2.71 (1H, t, J = 7.6 Hz), 3.39-3.52 (5H, m), 3.90-3.98 (2H, m), 5.60-6.30 (2H, br), 6.92-6.98 (2H, m), 7.18-7.23 (2H, m), 7.37 (1H, d, J = 1.5 Hz), 7.46 (1H, dd, J = 8.1, 1.5 Hz), 7.85 (1H, d, J = 7.1 Hz).<br>MS (ESI) m/z: 398 (M + H)$^+$. |
| Example 67 | 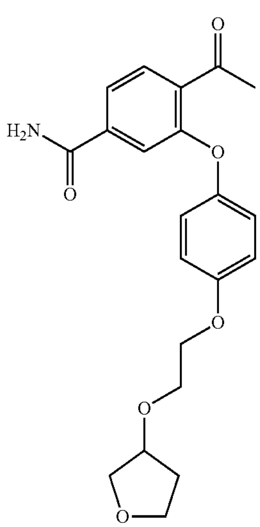 [SMILES: CC(=O)c1ccc(C(N)=O)cc1Oc1ccc(OCCOC2CCOC2)cc1] | $^1$H-NMR (DMSO-d$_6$) δ: 1.85-2.01 (2H, m), 2.60 (3H, s), 3.64-3.77 (6H, m), 4.07-4.12 (2H, m), 4.18-4.23 (1H, m), 7.00-7.03 (2H, m), 7.06-7.08 (2H, m), 7.29 (1H, d, J = 1.2 Hz), 7.50-7.58 (1H, br), 7.63 (1H, d, J = 8.0, 1.2 Hz), 7.73 (1H, d, J = 8.0 Hz), 8.05-8.12 (1H, br).<br>MS (ESI) m/z: 386 (M + H)$^+$. |

TABLE 1-17-continued

| Ex. No. | structure | data |
| --- | --- | --- |
| Example 68 | (structure) | ¹H-NMR (DMSO-d₆) δ: 1.85-2.01 (2H, m), 2.60 (3H, s), 3.63-3.77 (6H, m), 4.06-4.12 (2H, m), 4.17-4.24 (1H, m), 7.00-7.04 (2H, m), 7.05-7.09 (2H, m) 7.27-7.31 (1H, m) 7.50-7.57 (1H, br), 7.61-7.66 (1H, m), 7.71-7.75 (1H, m), 8.05-8.12 (1H, br).<br>MS (ESI) m/z: 386 (M + H)⁺. |

TABLE 1-18

| Ex. No. | structure | data |
| --- | --- | --- |
| Example 69 | (structure) | ¹H-NMR (DMSO-d₆) δ: 1.85-2.01 (2H, m), 2.60 (3H, s), 3.63-3.77 (6H, m), 4.06-4.12 (2H, m), 4.17-4.24 (1H, m), 6.99-7.04 (2H, m), 7.05-7.09 (2H, m), 7.29 (1H, d, J = 1.0 Hz), 7.50-7.57 (1H, br), 7.63 (1H, dd, J = 8.1, 1.0 Hz), 7.72 (1H, d, J = 8.1 Hz), 8,04-8.12 (1H, br).<br>MS (ESI) m/z: 386 (M + H)⁺. |

TABLE 1-18-continued

| Ex. No. | structure | data |
|---|---|---|
| Example 70 | 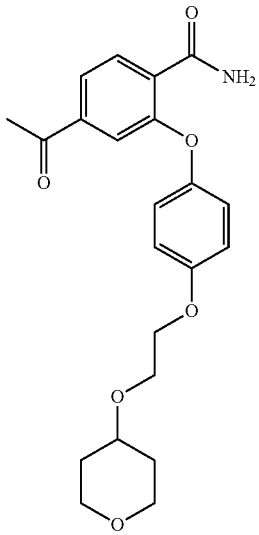 [SMILES: CC(=O)c1ccc(C(N)=O)c(Oc2ccc(OCCOC3CCOCC3)cc2)c1] | ¹H-NMR (CDCl₃) δ: 1.36-1.47 (2H, m), 1.82-1.91 (2H, m), 2.51 (3H, s), 3.30-3.37 (2H, m), 3.52-3.61 (1H, m), 3.74-3.84 (4H, m), 4.07-4.12 (2H, m), 6.98-7.09 (4H, m), 7.18 (1H, d, J = 1.5 Hz), 7.67-7.73 (1H, br), 7,73 (1H, dd, J = 8.0, 1.5 Hz), 7.75-7.82 (1H, br), 7.78 (1H, d, J = 8.0 Hz). MS (ESI) m/z: 400 (M + H)⁺. |
| Example 71 | 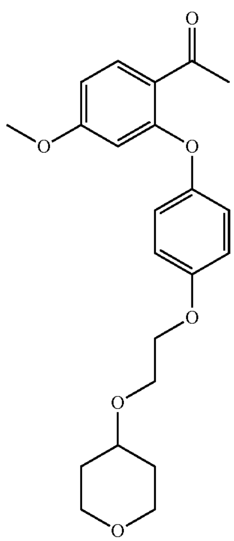 [SMILES: COc1ccc(C(C)=O)c(Oc2ccc(OCCOC3CCOCC3)cc2)c1] | ¹H-NMR (DMSO-d₆) δ: 1.36-1.46 (2H, m), 1.83-1.90 (2H, m), 2.53 (3H, s), 3.30-3.38 (2H, m), 3.53-3.60 (1H, m), 3.71 (3H, s), 3.74-3.83 (4H, m), 4.06-4.11 (2H, m), 6.24 (1H, d, J = 2.2 Hz), 6.77 (1H, dd, J = 9.0, 2.2 Hz), 6.98-7.07 (4H, m), 7.77 (1H, d, J = 9.0 Hz). Ms (ESI) m/z: 387 (M + H)⁺. |
| Example 72 | 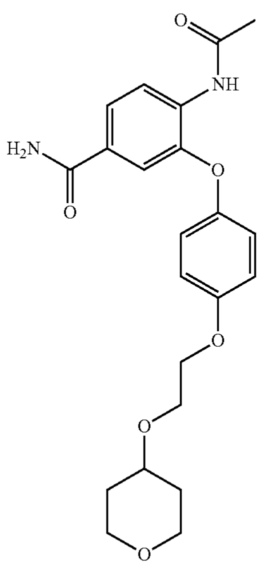 [SMILES: CC(=O)Nc1ccc(C(N)=O)cc1Oc1ccc(OCCOC2CCOCC2)cc1] | ¹H-NMR (DMSO-d₆) δ: 1.35-1.46 (2H, m), 1.81-1.92 (2H, m), 2.11 (3H, s), 3.29-3.37 (2H, m), 3.51-3.61 (1H, m), 3.72-3.85 (4H, m), 4.09 (2H, t, J = 4.6 Hz), 6.97-7.04 (4H, m), 7.21-7.31 (1H, br), 7.23 (1H, d, J = 1.2 Hz), 7.56 (1H, dd, J = 8.8, 1.2 Hz), 7.84-7.93 (1H, br), 8.15 (1H, d, J = 8.8 Hz), 9.62-9.69 (1H, br). MS (ESI) m/z: 415 (M + H)⁺. |

TABLE 1-19

| Ex. No. | structure | data |
| --- | --- | --- |
| Example 73 | 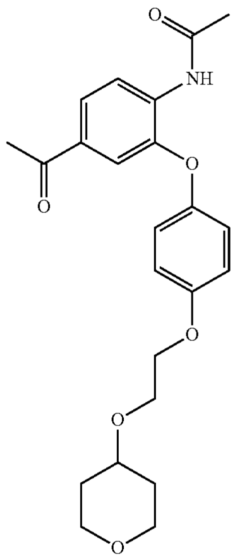 [SMILES: CC(=O)Nc1ccc(C(C)=O)cc1Oc1ccc(OCCOC2CCOCC2)cc1] | $^1$H-NMR (DMSO-$d_6$) δ: 1.35-1.46 (2H, m), 1.83-1.92 (2H, m), 2.15 (3H, s), 2.45 (3H, s), 3.30-3.38 (2H, m), 3.52-3.62 (1H, m), 3.74-3.85 (4H, m), 3.80 (2H, dt, J = 11.5, 4.4 Hz), 4.09 (2H, t, J = 4.7 Hz), 6.98-7.08 (4H, m), 7.17 (1H, d, J = 1.7 Hz), 7.70 (1H, dd, j = 8.5, 1.7 Hz), 8.30 (1H, d, J = 8.5 Hz), 9.76 (1H, s).<br>MS (ESI) m/z: 414 (M + H)$^+$. |
| Example 74 | 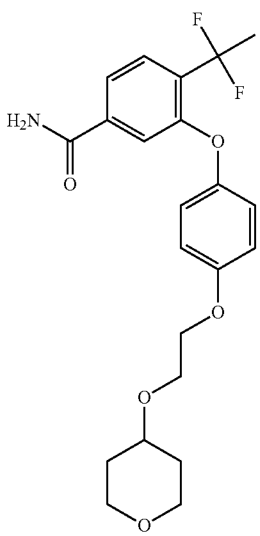 [SMILES: CC(F)(F)c1ccc(C(N)=O)cc1Oc1ccc(OCCOC2CCOCC2)cc1] | $^1$H-NMR (DMSO-$d_6$) δ: 1.34-1.47 (2H, m), 1.82-1.90 (2H, m), 2.06 (3H, t, J = 19.0 Hz), 3.30-3.37 (2H, m), 3.52-3.61 (1H, m), 3.76 (2H, t, J = 4.4 Hz), 3.77-3.84 (2H, m), 4.09 (2H, t, J = 4.4 Hz), 6.98-7.03 (4H, m), 7.27-7.31 (1H, m), 7.45-7.53 (1H, br), 7.61-7.68 (2H, m), 8.02-8.11 (1H, br).<br>MS (ESI) m/z: 422 (M + H)$^+$. |
| Example 75 | 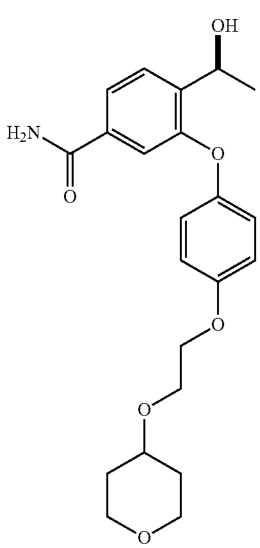 | $^1$H-NMR (DMSO-$d_6$) δ: 1.32 (3H, d, J = 6.4 Hz), 1.35-1.46 (2H, m), 1.81-1.90 (2H, m), 3.31-3.37 (2H, m), 3.51-3.60 (1H, m), 332-3.85 (4H, m), 4.03-4.11 (2H, m), 5.01-5.10 (1H, m), 5.25 (1H, d, J = 4.4 Hz), 6.90-7.01 (4H, m), 7.16-7.21 (1H, m), 7.27-7.35 (1H, br), 7.57-7.64 (2H, m), 7.87-7.94 (1H, br).<br>MS (ESI) m/z: 402 (M + H)$^+$. |

TABLE 1-19-continued

| Ex. No. | structure | data |
| --- | --- | --- |
| Example 76 | 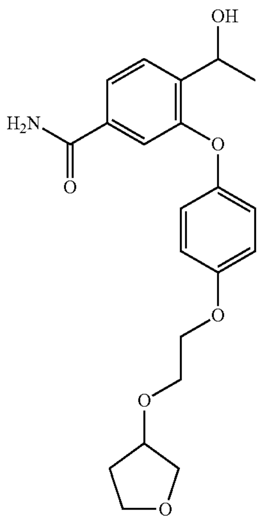 [SMILES: CC(O)c1ccc(C(N)=O)cc1Oc1ccc(OCCOC2CCOC2)cc1] | $^1$H-NMR (DMSO-$d_6$) δ: 1.32 (3H, d, J = 6.4 Hz), 1.85-2.00 (2H, m), 3.60-3.75 (6H, m), 4.05-4.10 (2H, m), 4.15-4.25 (1H, m), 5.01-5.10 (1H, m), 5.23 (1H, d, J = 3.9 Hz), 6.91-6.97 (1H, m), 7.18 (1H, s), 7.25-7.35 (1H, br), 7.57-7.63 (2H, m), 7.85-7.95 (1H, br).<br>MS (ESI) m/z: 388 (M + H)$^+$. |

TABLE 1-20

| Ex. No. | structure | data |
| --- | --- | --- |
| Example 77 | 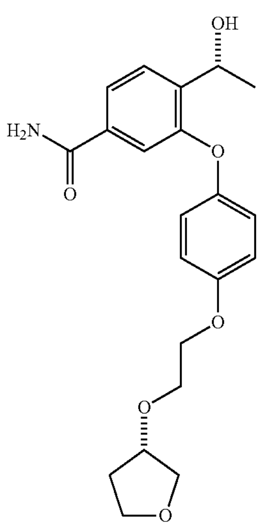 | $^1$H-NMR (DMSO-$d_6$) δ: 1.32 (3H, d, J = 6.3 Hz), 1.99-2.07 (2H, m), 3.61-3.75 (6H, m), 4.05 (2H, t, J = 4.6 Hz), 4.15-4.21 (1H, m), 5.00-5.09 (1H, m), 5.23 (1H, d, J = 4.2 Hz), 6.88-6.99 (4H, m), 7.18 (1H, s), 7.25-7.34 (1H, br), 7.56-7.64 (2H, m), 7.83-7.93 (1H, br).<br>MS (ESI) m/z: 388 (M + H)$^+$. |

TABLE 1-20-continued
| Ex. No. | structure | data |
| --- | --- | --- |
| Example 78 | 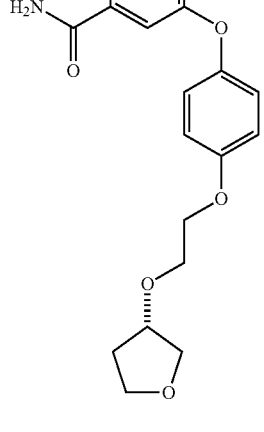 | $^1$H-NMR (DMSO-$d_6$) δ: 1.32 (3H, d, J = 6.3 Hz), 1.84-2.00 (2H, m), 3.61-3.75 (6H, m), 4.04 (2H, t, J = 4.6 Hz), 4.15-4.21 (1H, m), 5.00-5.09 (1H, m), 5.23 (1H, d, J = 4.2 Hz), 6.88-6.99 (4H, m), 7.18 (1H, s), 7.25-7.34 (1H, br), 7.56-7.64 (2H, m), 7.83-7.93 (1H, br).<br>MS (ESI) m/z: 388 (M + H)$^+$. |
| Example 79 | 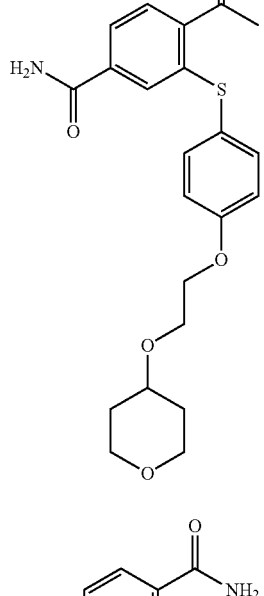 | $^1$H-NMR (DMSO-$d_6$) δ: 1.36-1.48 (2H, m), 1.83-1.93 (2H, m), 2.64 (3H, s), 3.30-3.38 (2H, m), 3.52-3.63 (1H, m), 3.76-3.85 (4H, m), 4.12-4.20 (2H, m), 7.03-7.10 (2H, m), 7.31 (1H, d, J = 1.4 Hz), 7.39-7.47 (3H, m), 7.64 (1H, dd, J = 8.0, 1.4 Hz), 7.99 (1H, s), 8.03 (1H, d, J = 8.0 Hz).<br>MS (ESI) m/z: 416 (M + H)$^+$. |
| Example 80 | 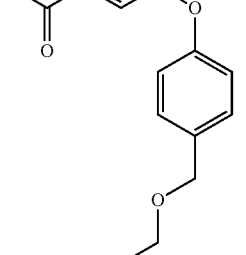 | $^1$H-NMR (CDCl$_3$) δ: 1.18 (6H, d, J = 6.1 Hz), 2.53 (3H, s), 3.58-3.69 (5H, m), 4.59 (2H, s), 5.85-5.95 (1H, br), 7.00-7.08 (2H, m), 7.37-7.44 (3H, m), 7.55-7.65 (1H, br), 7.71 (1H, dd, J = 8.2, 1.4 Hz), 8.35 (1H, d, J = 8.2 Hz).<br>MS (ESI) m/z: 394 (M + Na)$^+$. |

TABLE 1-21

| Ex. No. | structure | data |
| --- | --- | --- |
| Example 81 | (4-nitro-3-{[4-({(tetrahydro-2H-pyran-4-yl)oxy}methyl)phenyl]oxy}benzamide structure) | ¹H-NMR (DMSO-d₆) δ: 1.41-1.52 (2H, 1H), 1.86-1.93 (2H, m), 3.31-3.38 (2H, m), 3.55-3.63 (1H, m), 3.82 (2H, dt, J = 11.7, 4.2 Hz), 4.53 (2H, s), 7.07-7.12 (2H, m), 7.38-7.43 (2H, m), 7.53 (1H, d, J = 1.7 Hz), 7.69-7.75 (1H, br), 7.79 (1H, dd, J = 8.6, 1.7 Hz), 8.14 (1H, d, J = 8.6), 8.21-8.26 (1H, br). MS (ESI) m/z: 395 (M + Na)⁺. |
| Example 82 | (4-CF₂ structure) | ¹H-NMR (DMSO-d₆) δ: 1.41-1.52 (2H, m), 1.86-1.94 (2H, m), 3.32-3.39 (2H, m), 3.56-3.63 (1H, m), 3.82 (2H, dt, J = 11.7, 4.4 Hz), 4.53 (2H, s), 7.04-7.08 (2H, m), 7.38-7.43 (2H, m), 7.44 (1H, s), 7.59-7.65 (1H, br), 7.77 (1H, d, J = 8.0 Hz), 7.88 (1H, d, J = 8.0 Hz), 8.14-8.20 (1H, br). MS (ESI) m/z: 394 (M − H)⁻. |
| Example 83 | (4-CF₂H structure) | ¹H-NMR (DMSO-d₆) δ: 1.41-1.52 (2H, m), 1.86-1.94 (2H, m), 3.32-3.38 (2H, m), 3.55-3.63 (1H, m), 3.82 (2H, dt, J = 11.7, 4.4 Hz), 4.53 (2H, s), 7.03-7.08 (2H, m), 7.24 (1H, t, J = 54.4 Hz), 7.35 (1H, s), 7.37-7.42 (2H, m), 7.50-7.56 (1H, br), 7.74 (2H, s), 8.06-8.13 (1H, br). MS (ESI) m/z: 376 (M − H)⁻. |

TABLE 1-21-continued
| Ex. No. | structure | data |
|---|---|---|
| Example 84 | 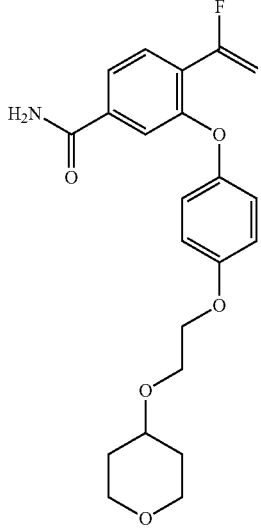 [SMILES: C=C(F)c1ccc(C(N)=O)cc1Oc1ccc(OCCOC2CCOCC2)cc1] | ¹H-NMR (DMSO-d₆) δ: 1.35-1.45 (2H, m), 1.80-1.90 (2H, m), 3.26-3.35 (2H, m), 3.48-3.58 (1H, m), 3.72-3.84 (4H, m), 4.02-4.12 (2H, m), 5.20 (1H, dd, J = 20.7, 2.9 Hz), 5.46 (1H, dd, J = 53.4, 2.9 Hz), 6.99 (4H, s), 7.30 (1H, s), 7.42-7.51 (1H, br), 7.60-7.69 (2H, m), 8.00-8.09 (1H, br).<br>MS (ESI) m/z: 402 (M + H)⁺. |
TABLE 1-22
| Ex. No. | structure | data |
|---|---|---|
| Example 85 | 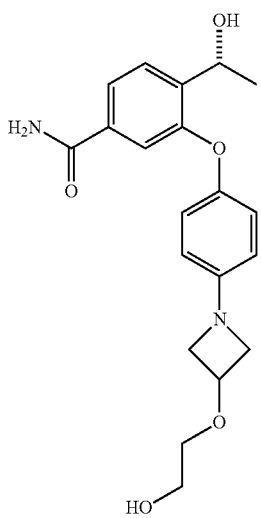 [SMILES: C[C@@H](O)c1ccc(C(N)=O)cc1Oc1ccc(N2CC(OCCO)C2)cc1] | 1H-NMR (DMSO-d₆) δ: 1.32 (3H, d, J = 6.4 Hz), 3.41 (2H, t, J = 4.9 Hz), 3.47-3.53 (2H, m), 3.55-3.61 (2H, m), 4.00-4.07 (2H, m), 4.36-4.46 (1H, m), 4.65 (1H, t, J = 5.4 Hz), 5.03-5.10 (1H, m), 5.21 (1H, d, J = 4.6 Hz), 6.43-6.4 (2H, m) 6.82-6.88 (2H, m), 7.12 (1H, s), 7.21-7.31 (1H, br), 7.56 (2H, s), 7.81-7.91 (1H, br).<br>MS (ESI) m/z: 373 (M + H)⁺. |

TABLE 1-22-continued
| Ex. No. | structure | data |
|---|---|---|
| Example 86 | 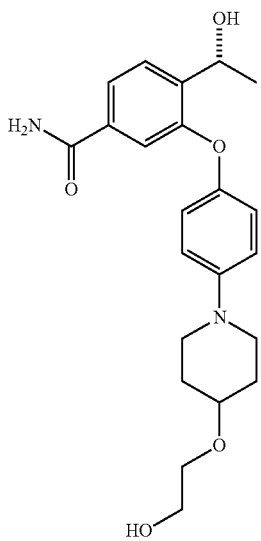 | $^1$H-NMR (DMSO-$d_6$) δ: 1.33 (3H, d, J = 6.4 Hz), 1.49-1.60 (2H, m), 1.90-1.98 (2H, m), 2.78-2.87 (2H, m), 3.40-3.53 (7H, m), 4.52-4.58 (1H, m), 5.02-5.09 (1H, m), 5.21 (1H, d, J = 4.2 Hz), 6.83-6.87 (2H, m), 6.94-6.98 (2H, m), 7.18-7.20 (1H, d, J = 1.7 Hz), 7.24-7.31 (1H, br), 7.58-7.62 (2H, m), 7.84-7.91 (1H, br).<br>MS (ESI) m/z: 401 (M + H)$^+$. |
| Example 87 | 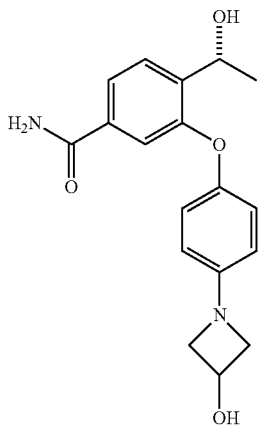 [SMILES: C[C@@H](O)c1ccc(C(N)=O)cc1Oc1ccc(N2CC(O)C2)cc1] | $^1$H-NMR (DMSO-$d_6$) δ: 1.34 (3H, d, J = 6.3 Hz), 3.45-3.52 (2H, m), 4.03-4.08 (2H, m), 4.49-4.58 (1H, m), 5.04-5.11 (1H, m), 5.18 (1H, d, J = 4.4 Hz), 5.53 (1H, d, J = 6.8 Hz), 6.43-6.48 (2H, m), 6.82-6.87 (2H, m), 7.11-7.13 (1H, m), 7.21-7.28 (1H, m), 7.54-7.59 (2H, br), 7.82-7.88 (1H, m).<br>Ms (ESI) m/z: 329 (M + H)$^+$. |
| Example 88 | 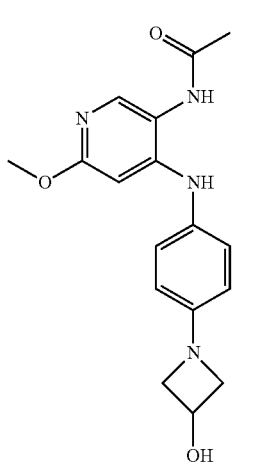 [SMILES: COc1cc(Nc2ccc(N3CC(O)C3)cc2)c(NC(C)=O)cn1] | $^1$H-NMR (DMSO-$d_6$) δ: 2.04 (3H, s), 3.46-3.55 (2H, m), 3.70 (3H, s), 4.02-4.12 (2H, m), 4.50-4.61 (1H, m), 5.54-5.62 (1H, m), 5.89 (1H, s), 6.41-6.52 (2H, m), 6.94-7.05 (2H, m), 7.54 (1H, s), 7.67 (1H, s), 9.01-9.12 (1H, br).<br>MS (ESI) m/z: 329 (M + H)$^+$. |

TABLE 1-23

| Ex. No. | structure | data |
|---|---|---|
| Example 89 | 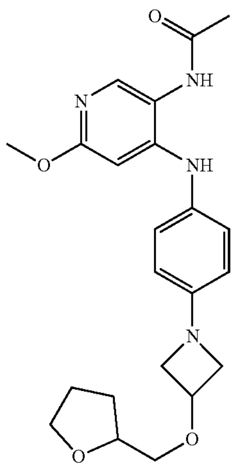 [SMILES: COc1cc(Nc2ccc(N3CC(OCC4CCCO4)C3)cc2)c(NC(C)=O)cn1] | ¹H-NMR (CDCl₃) δ: 1.55-1.70 (1H, m), 1.85-2.02 (3H, m), 3.43 (1H, dd, J = 10.1, 6.3 Hz), 3.50 (1H, dd, J = 10.1, 3.6 Hz), 3.74-3.82 (3H, m), 3.87-3.93 (1H, m), 3.90 (3H, s), 4.01-4.18 (3H, m), 4.47-4.55 (1H, m), 6.01 (1H, s), 6.44-6.52 (2H, m), 7.02-7.11 (2H, m), 9.02 (1H, s), 9.26 (1H, s).<br>MS (ESI) m/z: 413 (M + H)⁺. |
| Example 90 | 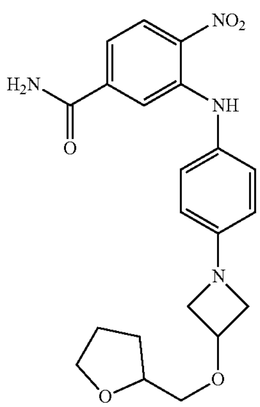 [SMILES: NC(=O)c1ccc([N+](=O)[O-])c(Nc2ccc(N3CC(OCC4CCCO4)C3)cc2)c1] | ¹H-NMR (CDCl₃) δ: 1.57-2.05 (4H, m), 3.40-3.54 (2H, m), 3.74-3.83 (3H, m), 3.86-3.94 (1H, m), 4.02-4.11 (1H, m), 4.12-4.20 (2H, m), 4.46-4.56 (1H, m), 5.57-5.77 (1H, br), 5.88-6.07 (1H, br), 6.46-6,54 (2H, m), 6.99 (1H, dd, J = 8.7, 1.9 Hz), 7.06-7.13 (2H, m), 7.38 (1H, d, J = 1.9 Hz), 8.23 (1H, d, J = 8.7 Hz), 9.40 (1H, s).<br>MS (ESI) m/z: 413 (M + H)⁺ |
| Example 91 | 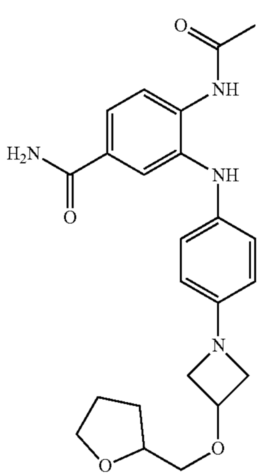 [SMILES: CC(=O)Nc1ccc(C(N)=O)cc1Nc1ccc(N2CC(OCC3CCCO3)C2)cc1] | ¹H-NMR (DM50-d₆) δ: 1.48-1.96 (4H, m), 2.07 (3H, s), 3.29-3.42 (2H, m), 3.49-3.57 (2H, m), 3.59-3.67 (1H, m), 3.70-3.78 (1H, m), 3.89-3.97 (1H, m), 3.99-4.05 (2H, m), 4.37-4.45 (1H, m), 6.40-6.48 (2H, m), 6.86-6.94 (2H, m), 6.98 (1H, s), 7.15 (1H, s), 7.23 (1H, d, J = 8.3 Hz), 7.44 (1H, s), 7.48 (1H, d, J = 8.3 Hz), 7.76 (1H, s), 9.31 (1H, s).<br>MS (ESI) m/z: 425 (M + H)⁺ |

TABLE 1-23-continued

| Ex. No. | structure | data |
|---|---|---|
| Example 92 | 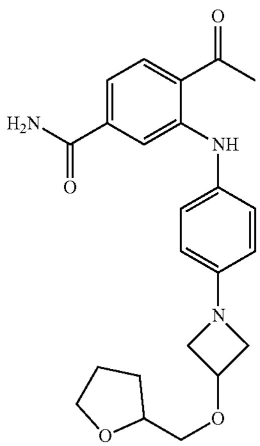 [SMILES: CC(=O)c1ccc(C(N)=O)cc1Nc1ccc(N2CC(OCC3CCCO3)C2)cc1] | $^1$H-NMR (CDCl$_3$) δ: 1.57-2.04 (4H, m), 2.65 (3H, s), 3.43 (1H, dd, J = 10.0, 6.6 Hz), 3.49 (1H, dd, J = 10.0, 3.8 Hz), 3,68-3.83 (3H, m), 3.85-3.94 (1H, m), 4.01-4.18 (3H, m), 4.45-4.55 (1H, m), 5.47-5.70 (1H, br), 5.83-6.05 (1H, br), 6.43-6.53 (2H, m), 6.99 (1H, dd, J = 8.2, 1.4 Hz), 7.04-7.12 (2H, m), 7.27 (1H, d, J = 1.4 Hz), 7.82 (1H, d, J = 8.2 Hz), 10.3 (1H, s). MS (ESI) m/z: 410 (M + H)$^+$ |

TABLE 1-24

| Ex. No. | structure | data |
|---|---|---|
| Example 93 | 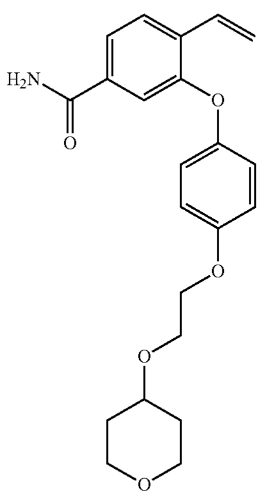 [SMILES: C=Cc1ccc(C(N)=O)cc1Oc1ccc(OCCOC2CCOCC2)cc1] | $^1$H-NMR (DMSO-d$_6$) δ: 1.36-1.48 (2H, m), 1.82-1.92 (2H, m), 3.28-3.34 (2H, m), 3.52-3.58 (1H, m), 3.71-3.84 (4H, m), 4.03-4.08 (2H, m), 5.40 (1H, d, J = 11.2 Hz), 6.00 (1H, d, J = 17.8 Hz), 6.90-7.02 (5H, m), 6.90-7.02 (1H, d, J = 1.7 Hz), 7.36-7.42 (1H, br), 7.62 (1H, dd, J = 8.3, 1.7 Hz), 7.74 (1H, d, J = 8.3 Hz), 7.94-8.01 (1H, br). MS (ESI) m/z: 384 (M + H)$^+$ |
| Example 94 | 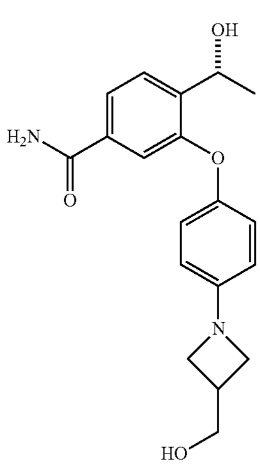 [SMILES: C[C@@H](O)c1ccc(C(N)=O)cc1Oc1ccc(N2CC(CO)C2)cc1] | $^1$H-NMR (DMSO-d$_6$) δ: 1.34 (3H, d, J = 6.4 Hz), 2.70-2.83 (1H, m), 3.48-3.56 (2H, m), 3.57-3.63 (2H, m), 3.81 (2H, t, J = 5.1 Hz), 4.73 (2H, t, J = 5.1 Hz), 5.04-5.11 (1H, m), 5.21 (1H, d, J = 4.4 Hz), 6.40-6.46 (2H, m), 6.83-6.87 (2H, m), 7.11-7.14 (1H, m), 7.24-7.31 (1H, br), 7.54-7.59 (2H, m), 7.84-7.91 (1H, br). MS (ESI) m/z: 343 (M + H)$^+$. |

TABLE 1-24-continued

| Ex. No. | structure | data |
| --- | --- | --- |
| Example 95 | 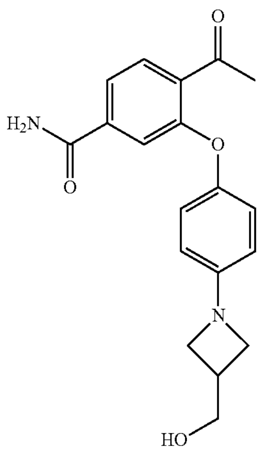 [SMILES: CC(=O)c1ccc(C(N)=O)cc1Oc1ccc(N2CC(CO)C2)cc1] | $^1$H-NMR (CDCl$_3$) δ: 1.65-1.78 (1H, br), 2.71 (3H, s), 2.89-2.97 (1H, m), 3.87-4.00 (4H, m), 5.55-5.75 (1H, br), 5.92-6.11 (1H, br), 6.44-6.50 (2H, m), 6.90-6.97 (2H, m), 7.25 (1H, d, J = 1.7 Hz), 7.39 (1H, dd, J = 8.0, 1.7 Hz), 7.82 (1H, d, J = 8.0 Hz).<br>MS (ESI) m/z: 341 (M + H)$^+$. |
| Example 96 | 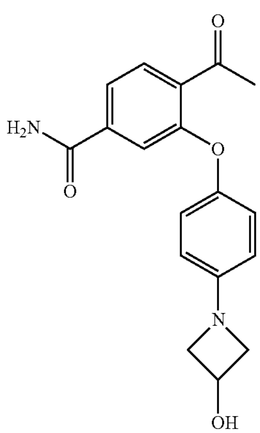 [SMILES: CC(=O)c1ccc(C(N)=O)cc1Oc1ccc(N2CC(O)C2)cc1] | $^1$H-NMR (DMSO-d$_6$) δ: 2.60 (3H, s), 3.50 (2H, dd, J = 7.4, 5.0 Hz), 4.04-4.09 (2H, m), 4.50-4.60 (1H, m), 5.57 (1H, d, J = 6.6 Hz), 6.46-6.51 (2H, m), 6.95-7.00 (2H, m), 7.23-7.25 (1H, m), 7.45-7.52 (1H, br), 7.56-7.60 (1H, m), 7.69 (1H, d, J = 7.8 Hz), 8.01-8.08 (1H, br).<br>MS (ESI) m/z: 327 (M + H)$^+$. |

TABLE 1-25

| Ex. No. | structure | data |
| --- | --- | --- |
| Example 97 | 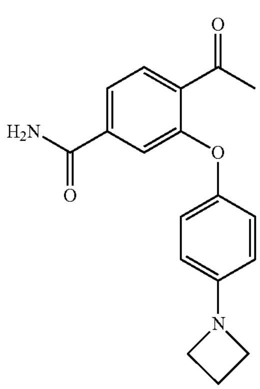 [SMILES: CC(=O)c1ccc(C(N)=O)cc1Oc1ccc(N2CCC2)cc1] | $^1$H-NMR (DMSO-d$_6$) δ: 2.29 (2H, quintet, J = 7.3 Hz), 2.60 (3H, s), 3.80 (4H, t, J = 7.3 Hz), 6.44-6.49 (2H, m), 6.95-7.00 (2H, m), 7.24 (1H, d, J = 1.2 Hz), 7.45-7.55 (1H, br), 7.57 (1H, dd, J = 8.1, 1.2 Hz), 7.69 (1H, d, J = 8.1 Hz), 8.00-8.10 (1H, br).<br>MS (ESI) m/z: 311 (M + H)$^+$. |

TABLE 1-25-continued

| Ex. No. | structure | data |
| --- | --- | --- |
| Example 98 | 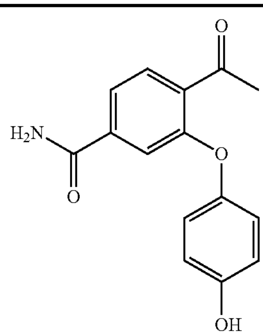 | $^1$H-NMR (DMSO-$d_6$) δ: 2.60 (3H, s), 6.79-6.87 (2H, m), 6.94-7.00 (2H, m), 7.27 (1H, d, J =1.4 Hz), 7.45-7.56 (1H, br), 7.61 (1H, dd, J = 1.4, 8.1 Hz), 7.70 (1H, d, J = 8.1 Hz), 8.02-8.11 (1H, br), 9.45 (1H, s). MS (ESI) m/z: 272 (M + H)$^+$ |
| Example 99 | 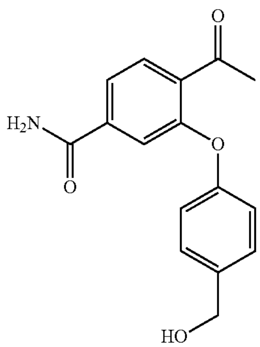 [SMILES: CC(=O)c1ccc(C(N)=O)cc1Oc1ccc(CO)cc1] | $^1$H-NMR (DMSO-$d_6$) δ: 2.58 (3H, s), 4.50 (2H, d, J = 5.6 Hz), 5.20 (1H, t, J = 5.6 Hz), 7.03-7.08 (2H, m), 7.35-7.42 (2H, m), 7.50-7.60 (1H, br), 7.69 (1H, dd, J = 8.2, 1.6 Hz), 7.76 (1H, d, J = 8.2 Hz), 8.06-8.15 (1H, br). MS (ESI) m/z: 308 (M + Na)$^+$. |

Experimental Example 1

The CDK8 and CDK19 inhibitory activity of compound (I) of the present invention was evaluated by the following method.

The test compound (compound (I)) dissolved in DMSO was diluted with an assay buffer (QSS Assist STK ELISA Kit (CDK8/CycC), Carna Bioscience) to give a primary dilution solution with a DMSO concentration of 40%. The above-mentioned primary dilution solution (10 μL) was dispensed in a streptavidin-coated 96 well plate, and an assay buffer mixture (10 μL) containing 500 nM substrate (Carna Bioscience), 10 mM $MgCl_2$ (Carna Bioscience) and 100 μM ATP (Carna Bioscience) was added. After the above-mentioned addition, 10 μL of a kinase solution was added (1 ng/μL CDK8/CycC (Carna Bioscience) diluted with assay buffer is used for measurement of CDK8 inhibitory activity and for 5 ng/μL CDCl2 L6/CycC (Carna Bioscience) diluted with assay buffer is used for measurement of CDK19 inhibitory activity). After the above-mentioned addition, the mixture was stood in an incubator at 24-26° C. for 30 min. After completion of the reaction, the solution in the well was discarded and the well was immediately washed 5 times with 150 μL per well of a wash buffer (50 mM Tris-HCl (pH 7.5), 150 mM NaCl, 0.02% Tween-20). A blocking buffer (0.1% BSA-containing assay buffer) (100 μL) was added to each well and the mixture was stood at room temperature for 30 min. The solution in the well was discarded, a primary antibody solution (Carna Bioscience) (50 μL) was added to each well and the mixture was stood at room temperature for 30 min. The solution in the well was discarded, and the well was immediately washed 5 times with 150 μL per well of a wash buffer. HRP-labeled secondary antibody solution (Carna Bioscience) (50 μL) was added to each well and the mixture was stood at room temperature for 30 min. The solution in the well was discarded and the well was immediately washed 5 times with 150 μL per well of a wash buffer. A color development reagent (ELISA POD substrate TMB kit (HYPER), Nacalai Tesque) (100 μL) was added to each well and the mixture was reacted at room temperature for 5 min. The reaction was quenched by adding a color developing reaction termination drug (Nacalai Tesque) (100 μL) to each well, and the absorbance (450 nm) was measured by a plate reader.

Using the absorbance of the test compound non-addition well as a control and the absorbance of the enzyme non-addition well as a blank, the CDK8 and CDK19 inhibitory rate was determined at 1 μM of each test compound.

The compounds 5, 13, 22, 28, 29, 32, 33, 43, 48, 50, 64, 65, 67 and 84 showed a CDK8 inhibitory rate of not less than 90% at 1 M.

The compounds 32 and 43 showed a CDK19 inhibitory rate of not less than 90% at 1 μM.

Experimental Example 2

The action of compound (I) of the present invention on serine/threonine kinase activity was examined by Off-chip Mobility Shift Assay (MSA). The method is shown below.

The action of a test compound (1 μM) on 39 kinds of serine/threonine kinase activity was examined. A solution of 4-fold concentration of compound 32 (5 μL) prepared by using an assay buffer (20 mM HEPES, 0.01% Triton X-100, 2 mM DTT, pH 7.5), a substrate/ATP/metal solution (5 μL) and a kinase 25 solution (10 μL) were mixed in a well of a polypropylene 384 well plate and the mixture was reacted at room temperature for 1 or 5 hr. The reaction was discontinued by adding 70 μL of Termination Buffer (Carna Biosciences). The substrate peptide and phosphorylated peptide in the reaction solution were separated and quantified by LabChip System (Perkin Elmer).

The kinase reaction was evaluated based on a resultant product ratio (P/(P+S)) calculated from substrate peptide peak height (S) and phosphorylated peptide peak height (P).

Compound 32 did not affect 39 kinds of serine/threonine kinase (AKT1, AMPKα1/β1/γ1, AurA, CaMK4, CDCl$_2$/CycB1, CDK2/Cyc2, CDK2/CycE1, CDK3/CycE1, CDK4/CycD3, CDK5/p25, CDK6/CycD3, CDK7/CycH/MAT1, CDK9/CycT1, CHK1, CK1ε, DAPK1, DYRK1B, Erk2, GSK3β, HGK, IKKβ, IRAK4, JNK2, MAP4K2, MAPKAPK2, MST1, NEK2, p38α, p70S6K, PAK2, PBK, PDK1, PIM1, PKACα, PKCα, PKD2, ROCK1, SGK and TSSK1) activity.

Experimental Example 3

The human acute myeloid leukemia MV4; 11 cell proliferation inhibitory activity of compound (I) of the present invention was evaluated by the following method.

A cell suspension (100 μL, 10,000 cells/well) of human acute myeloid leukemia MV4; 11 (purchased from American Type Culture Collection) was seeded on a 96 well plate and cultured in a 5% carbon dioxide gas incubator at 37° C. for one day. After the above-mentioned culture, each test compound (compound (I)) was added to a concentration of 1 μM and the mixture was further cultured for 3 days. After the above-mentioned culture, 40 μL of CellTiter 96 (registered trade mark) Aqueous One Solution Cell Proliferation Assay (Promega KK) was added to the 96 well-plate, the mixture was reacted for 3 hr, and the absorbance (490 nm) was measured by a plate reader.

Using the absorbance of the test compound non-addition well as a control and the absorbance of the cell non-seeded well as a blank, the cell proliferation inhibitory rate was determined at 1 μM of each test compound.

The compounds 5, 28, 32, 33, 48, 50, 64, 67 and 84 showed a cell proliferation inhibitory rate of not less than 50% at 1 μM.

From the above results, it was found that compound (I) of the present invention has a superior inhibitory activity against cyclin-dependent kinase (CDK) 8 and 19, and has a high cell proliferation inhibitory activity against human acute myeloid leukemia cells.

| Formulation Example 1 (production of capsule) | |
|---|---|
| 1) Example compound (compound (I)) | 10 mg |
| 2) fine powder cellulose | 10 mg |
| 3) lactose | 19 mg |
| 4) magnesium stearate | 1 mg |
| total | 40 mg |

1), 2), 3) and 4) are mixed and filled in a gelatin capsule.

| Formulation Example 2 (production of tablet) | |
|---|---|
| 1) Example compound (compound (I)) | 10 g |
| 2) lactose | 50 g |
| 3) cornstarch | 15 g |
| 4) carboxymethylcellulose calcium | 44 g |
| 5) magnesium stearate | 1 g |
| 1000 tablets total | 120 g |

The total amount of 1), 2), 3) and 30 g of 4) are kneaded with water, vacuum dried and sieved. The sieved powder is mixed with 14 g of 4) and 1 g of 5), and the mixture is punched with a tableting machine. In this way, 1000 tablets containing 10 mg of the Example compound per tablet are obtained.

INDUSTRIAL APPLICABILITY

The compound (I) of the present invention has a superior inhibitory activity against cyclin-dependent kinase (CDK) 8 and 19. According to the present invention, therefore, a superior CDK8 and/or CDK19 inhibitor can be provided. According to the present invention, moreover, a medicament useful as an agent for preventing and/or treating diseases associated with CDK8 and/or CDK19, particularly, cell proliferative diseases such as cancer and the like can also be provided.

This application is based on a patent application No. 2017-073969 filed in Japan, the contents of which are so incorporated in full herein.

The invention claimed is:
1. A method of inhibiting cyclin-dependent kinase 8 and/or 19 comprising administering to a subject containing the same an effective amount of a compound represented by the formula (I):

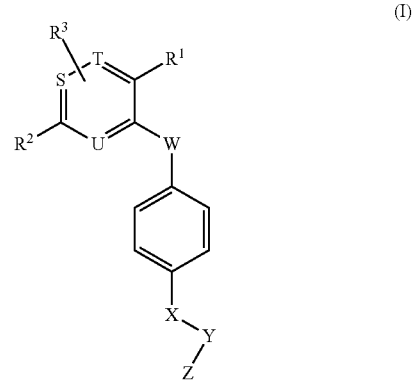

wherein
R$^1$ is a cyano group, a C$_{1-6}$ alkylcarbonyl group, a C$_{1-6}$ alkylcarbonylamino group, a nitro group, a halogeno C$_{1-6}$ alkyl group, a C$_{2-6}$ alkenyl group, a halogeno C$_{2-6}$ alkenyl group, a carbamoyl group, or a hydroxy C$_{1-6}$ alkyl group, R$^2$ is a C$_{1-6}$ alkoxy group, a carbamoyl group, a C$_{1-6}$ alkylaminocarbonyl group or a C$_{1-6}$ alkylcarbonyl group, R$^3$ is a hydrogen atom or a halogen atom, either one of S, T and U is =N— and others of S, T and U are =CH— (=C— when substituted by $R^3$) or each of S, T and U is =CH— (=C— when substituted by $R^3$), W is —NH—, —O— or —S—, X is a single bond, -saturated heterocyclyl-, —$CH_2$—$(CH_2)_n$—, —O—$(CH_2)_n$—, —$(CH_2)_n$—O— or —CH=CH—$(CH_2)_n$—, n is any one integer selected from 1-4, Y is a single bond, —O— or —CO—, Z is a hydrogen atom, a saturated heterocyclic group optionally substituted by any group selected from substituent group u or a $C_{1-6}$ alkyl group optionally substituted by any group selected from substituent group α, substituent group α is a saturated heterocyclic group, a hydroxy $C_{1-6}$ alkyl group, an aminosulfonylamino group, a carboxy group, a hydroxy group, a $C_{1-6}$ alkoxy group, or a $C_{1-6}$ alkyl group, or a pharmaceutically acceptable salt thereof.

2. The method according to claim 1, wherein $R^1$ is a cyano group, an acetyl group, an acetylamino group, a nitro group, a trifluoromethyl group, a 1,1-difluoroethyl group, a 1-fluoroethyl group, a difluoromethyl group, a carbamoyl group or a 1-hydroxyethyl group.

3. The method according to claim 1, wherein $R^2$ is a methoxy group, a carbamoyl group, a methylaminocarbonyl group or an acetyl group.

4. The method according to claim 1, wherein each of S, T and U is =CH—.

5. The method according to claim 1, wherein X is -saturated heterocyclyl- or —O—$(CH_2)_n$— and n is 2.

6. The method according to claim 1, wherein Y is a single bond or —O—.

7. The method according to claim 1, wherein Z is a $C_{1-6}$ alkyl group substituted by a hydroxy group, a tetrahydrofuranyl group, a tetrahydropyranyl group, a piperazinyl group or a morpholinyl group.

8. The method according to claim 1, wherein $R^1$ is a cyano group, an acetyl group, an acetylamino group, a nitro group, a trifluoromethyl group, a 1,1-difluoroethyl group, a 1-fluoroethyl group, a difluoromethyl group, a carbamoyl group or a 1-hydroxyethyl group, $R^2$ is a methoxy group, a carbamoyl group, a methylaminocarbonyl group or an acetyl group, each of S, T and U is =CH—, X is -saturated heterocyclyl- or —O—$(CH_2)_n$—, n is 2, Y is a single bond or —O—, and Z is a $C_{1-6}$ alkyl group substituted by a hydroxy group, a tetrahydrofuranyl group, a tetrahydropyranyl group, a piperazinyl group or a morpholinyl group.

9. The method according to claim 1, wherein the compound represented by the formula (I) is (1)    3-{4-[3-(2-hydroxyethoxy)azetidin-1-yl]phenylamino}-N-methyl-4-nitrobenzamide

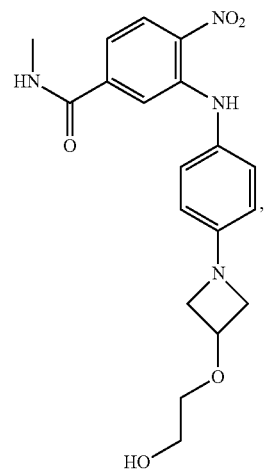 [SMILES: CNC(=O)c1ccc([N+](=O)[O-])c(Nc2ccc(N3CC(OCCO)C3)cc2)c1]

(2)    3-{4-[3-(2-hydroxyethoxy)azetidin-1-yl]phenylamino}-4-nitrobenzamide

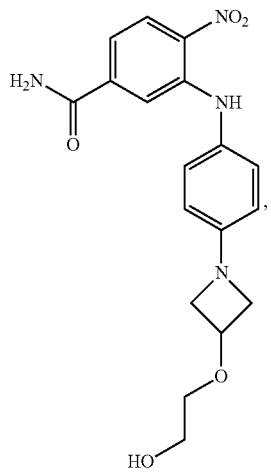 [SMILES: NC(=O)c1ccc([N+](=O)[O-])c(Nc2ccc(N3CC(OCCO)C3)cc2)c1]

(3) 4-acetyl-3-{4-[2-(tetrahydropyran-4-yloxy)ethoxy]phenoxy}benzamide
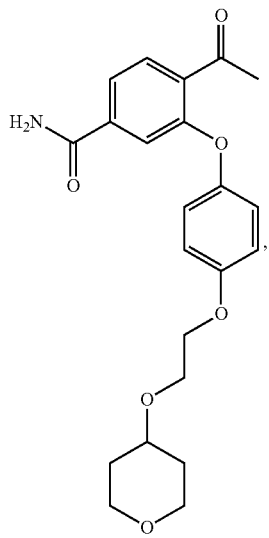 [SMILES: CC(=O)c1ccc(C(N)=O)cc1Oc1ccc(OCCOC2CCOCC2)cc1]
(4) 4-acetyl-3-{4-[2-(2-isopropoxyethoxy)ethoxy]phenoxy}benzamide
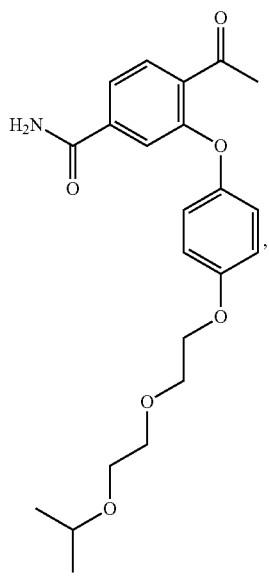
(5) 4-nitro-3-{4-[2-(tetrahydropyran-4-yloxy)ethoxy]phenylamino}benzamide
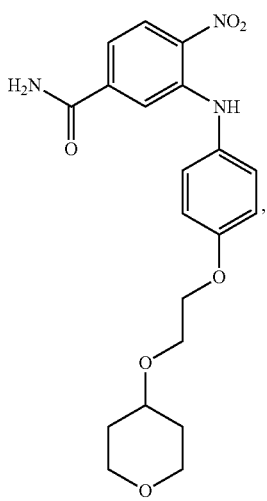 [SMILES: NC(=O)c1ccc([N+](=O)[O-])c(Nc2ccc(OCCOC3CCOCC3)cc2)c1]
(6) 4-acetyl-3-{4-[2-(tetrahydrofuran-3-yloxy)ethoxy]phenoxy}benzamide
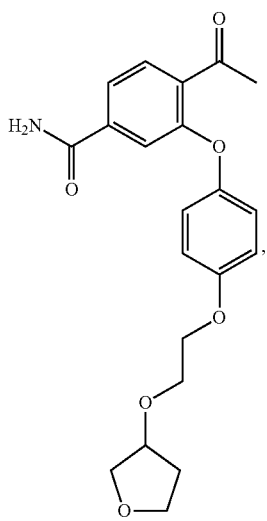 [SMILES: CC(=O)c1ccc(C(N)=O)cc1Oc1ccc(OCCOC2CCOC2)cc1]

(7) 4-acetyl-3-{4-[3-(2-hydroxyethoxy)azetidin-1-yl]phenoxy}benzamide

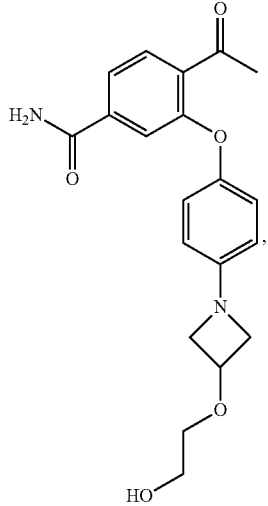 [SMILES: CC(=O)c1ccc(C(N)=O)cc1Oc1ccc(N2CC(OCCO)C2)cc1]

(8) 3-{4-[2-(tetrahydropyran-4-yloxy)ethoxy]phenoxy}-4-trifluoromethylbenzamide

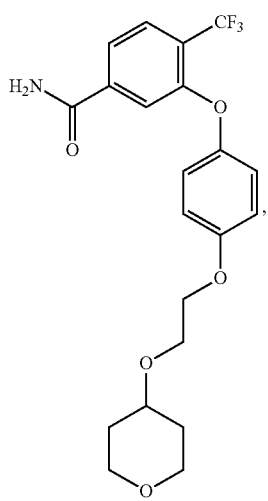 [SMILES: NC(=O)c1ccc(C(F)(F)F)c(Oc2ccc(OCCOC3CCOCC3)cc2)c1]

or (9) 4-(1-fluorovinyl)-3-{4-[2-(tetrahydropyran-4-yloxy)ethoxy]phenoxy}benzamide

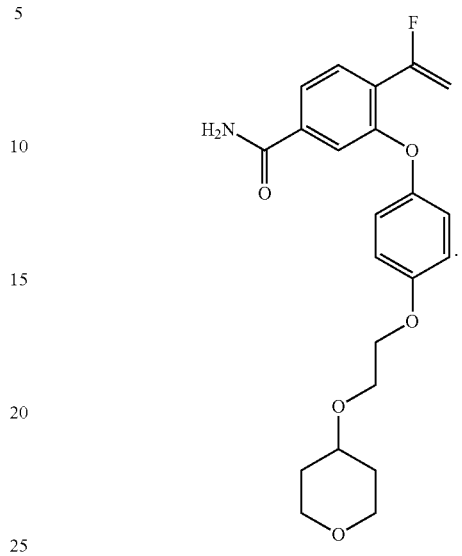

10. A method of preventing or treating cancer in a subject comprising administering to the subject an effective amount of the compound described in claim 1.

11. The method according to claim 10, wherein the aforementioned cancer is at least one kind selected from the group consisting of breast cancer, pancreatic cancer, bladder cancer, prostate cancer, esophageal cancer, stomach cancer, uterine cancer, ovarian cancer, brain tumor, colorectal cancer, hematologic cancer, liver cancer, skin cancer, lung cancer and thyroid cancer.

12. The method according to claim 10 further comprising administering at least one kind selected from the group consisting of a chemotherapeutic agent, a hormonal therapeutic agent, a molecular targeting agent, an anti-inflammatory agent, an immunosuppressant and an immunotherapeutic agent.

13. The method according to claim 11 further comprising administering at least one kind selected from the group consisting of a chemotherapeutic agent, a hormonal therapeutic agent, a molecular targeting agent, an anti-inflammatory agent, an immunosuppressant and an immunotherapeutic agent.

* * * * *